United States Patent
Chen et al.

(10) Patent No.: US 11,517,588 B2
(45) Date of Patent: Dec. 6, 2022

(54) NANOPARTICLE, PREPARATION PROCESS AND USES THEREOF

(71) Applicant: National Tsing Hua University, Hsinchu (TW)

(72) Inventors: Yun-Ching Chen, Hsinchu (TW); Tsai-Te Lu, Hsinchu (TW); Yun-Chieh Sung, Hsinchu (TW)

(73) Assignee: NATIONAL TSING HUA UNIVERSITY, Hsinchu (TW)

(*) Notice: Subject to any disclaimer, the term of this patent is extended or adjusted under 35 U.S.C. 154(b) by 10 days.

(21) Appl. No.: 16/909,134

(22) Filed: Jun. 23, 2020

(65) Prior Publication Data
US 2021/0106615 A1  Apr. 15, 2021

Related U.S. Application Data

(60) Provisional application No. 62/912,852, filed on Oct. 9, 2019.

(51) Int. Cl.
| | | |
|---|---|---|
| *A61K 33/26* | (2006.01) | |
| *A61K 9/107* | (2006.01) | |
| *A61P 35/00* | (2006.01) | |
| *A61K 31/704* | (2006.01) | |
| *A61K 47/34* | (2017.01) | |

(52) U.S. Cl.
CPC ............. *A61K 33/26* (2013.01); *A61K 9/107* (2013.01); *A61K 31/704* (2013.01); *A61K 47/34* (2013.01); *A61P 35/00* (2018.01)

(58) Field of Classification Search
CPC ................ A61K 33/26; A61P 35/00
See application file for complete search history.

(56) References Cited

U.S. PATENT DOCUMENTS

| | | | |
|---|---|---|---|
| 2013/0209566 A1* | 8/2013 | Jablonski | A61K 38/385 424/490 |
| 2014/0234217 A1* | 8/2014 | Rogers | A61P 35/00 424/9.1 |
| 2018/0208616 A1* | 7/2018 | Lu | C07F 15/025 |
| 2020/0330655 A1* | 10/2020 | Thaxton | A61P 9/12 |

OTHER PUBLICATIONS

Liu, S. et al. "Inhibition of orthotopic secondary hepatic carcinoma in mice by doxorubicin-loaded electrospun polylactide nanofibers" J. Mater. Chem. B, 2013, 1, 101-109 (Year: 2013).*

Yun-Chieh Sung et al., "Delivery of nitric oxide with a nanocarrier promotes tumour vessel normalization and potentiates anti-cancer therapies", Nature Nanotechnology, published online: Nov. 18, 2019.

Yunching Chen et al., "New Cancer Treatment Developed at NTHU", Business Wire, Feb. 26, 2020.

* cited by examiner

*Primary Examiner* — Andrew S Rosenthal
(74) *Attorney, Agent, or Firm* — WPAT, PC

(57) ABSTRACT

The present disclosure provides a nanoparticle, a preparation process thereof, a method for treating cancer, a method for enhancing effect of a liver cancer drug, a method for ameliorating tumor hypoxia, and a method for enhancing effect of a liver cancer vaccine by using the nanoparticle.

14 Claims, 39 Drawing Sheets
Specification includes a Sequence Listing.

SEQUENCE LISTING

<160> NUMBER OF SEQ ID NOS: 88

<210> SEQ ID NO 1
<211> LENGTH: 20
<212> TYPE: DNA
<213> ORGANISM: Artificial Sequence
<220> FEATURE:
<223> OTHER INFORMATION: synthetic primer

<400> SEQUENCE: 1
caaccagctc tgggaatctg          20

<210> SEQ ID NO 2
<211> LENGTH: 20
<212> TYPE: DNA
<213> ORGANISM: Artificial Sequence
<220> FEATURE:
<223> OTHER INFORMATION: synthetic primer

```
<400> SEQUENCE: 2
aatcggcctt ttcttccttc                                                      20

<210> SEQ ID NO 3
<211> LENGTH: 20
<212> TYPE: DNA
<213> ORGANISM: Artificial Sequence
<220> FEATURE:
<223> OTHER INFORMATION: synthetic primer

<400> SEQUENCE: 3
tgcttctggg gacttttctg                                                      20

<210> SEQ ID NO 4
<211> LENGTH: 20
<212> TYPE: DNA
<213> ORGANISM: Artificial Sequence
<220> FEATURE:
<223> OTHER INFORMATION: synthetic primer

<400> SEQUENCE: 4
tggccttctt cacatgtttg                                                      20

<210> SEQ ID NO 5
<211> LENGTH: 20
<212> TYPE: DNA
<213> ORGANISM: Artificial Sequence
<220> FEATURE:
<223> OTHER INFORMATION: synthetic primer

<400> SEQUENCE: 5
gtccttcttg ctgtggcaat                                                      20

<210> SEQ ID NO 6
<211> LENGTH: 20
<212> TYPE: DNA
<213> ORGANISM: Artificial Sequence
<220> FEATURE:
<223> OTHER INFORMATION: synthetic primer

<400> SEQUENCE: 6
acggttatca aaacaacgcc                                                      20

<210> SEQ ID NO 7
<211> LENGTH: 19
<212> TYPE: DNA
<213> ORGANISM: Artificial Sequence
<220> FEATURE:
<223> OTHER INFORMATION: synthetic primer

<400> SEQUENCE: 7
ccagagccac atgctccta                                                       19

<210> SEQ ID NO 8
<211> LENGTH: 20
<212> TYPE: DNA
<213> ORGANISM: Artificial Sequence
<220> FEATURE:
<223> OTHER INFORMATION: synthetic primer

<400> SEQUENCE: 8
aggggagaaa tcgatgacag                                                      20

<210> SEQ ID NO 9
```

```
<211> LENGTH: 20
<212> TYPE: DNA
<213> ORGANISM: Artificial Sequence
<220> FEATURE:
<223> OTHER INFORMATION: synthetic primer

<400> SEQUENCE: 9
cctgaacagc aacttgacca                                                     20

<210> SEQ ID NO 10
<211> LENGTH: 20
<212> TYPE: DNA
<213> ORGANISM: Artificial Sequence
<220> FEATURE:
<223> OTHER INFORMATION: synthetic primer

<400> SEQUENCE: 10
gcaatggcca tagaaaggaa                                                     20

<210> SEQ ID NO 11
<211> LENGTH: 20
<212> TYPE: DNA
<213> ORGANISM: Artificial Sequence
<220> FEATURE:
<223> OTHER INFORMATION: synthetic primer

<400> SEQUENCE: 11
agtgtggagt tcgaggaacc                                                     20

<210> SEQ ID NO 12
<211> LENGTH: 19
<212> TYPE: DNA
<213> ORGANISM: Artificial Sequence
<220> FEATURE:
<223> OTHER INFORMATION: synthetic primer

<400> SEQUENCE: 12
gagtccggat ctaggcagg                                                      19

<210> SEQ ID NO 13
<211> LENGTH: 20
<212> TYPE: DNA
<213> ORGANISM: Artificial Sequence
<220> FEATURE:
<223> OTHER INFORMATION: synthetic primer

<400> SEQUENCE: 13
tgccaccttt tgacagtgat                                                     20

<210> SEQ ID NO 14
<211> LENGTH: 20
<212> TYPE: DNA
<213> ORGANISM: Artificial Sequence
<220> FEATURE:
<223> OTHER INFORMATION: synthetic primer

<400> SEQUENCE: 14
tgtcctcatc ctggaaggtc                                                     20

<210> SEQ ID NO 15
<211> LENGTH: 19
<212> TYPE: DNA
<213> ORGANISM: Artificial Sequence
<220> FEATURE:
<223> OTHER INFORMATION: synthetic primer

<400> SEQUENCE: 15
```

-continued ccgatgggtt gtaccttgt         19

<210> SEQ ID NO 16
<211> LENGTH: 20
<212> TYPE: DNA
<213> ORGANISM: Artificial Sequence
<220> FEATURE:
<223> OTHER INFORMATION: synthetic primer

<400> SEQUENCE: 16
cggactccgc aaagtctaag         20

<210> SEQ ID NO 17
<211> LENGTH: 20
<212> TYPE: DNA
<213> ORGANISM: Artificial Sequence
<220> FEATURE:
<223> OTHER INFORMATION: synthetic primer

<400> SEQUENCE: 17
agctgctcaa ggcttcctta         20

<210> SEQ ID NO 18
<211> LENGTH: 25
<212> TYPE: DNA
<213> ORGANISM: Artificial Sequence
<220> FEATURE:
<223> OTHER INFORMATION: synthetic primer

<400> SEQUENCE: 18
agtaacaatc acttcaactt tgtcg         25

<210> SEQ ID NO 19
<211> LENGTH: 20
<212> TYPE: DNA
<213> ORGANISM: Artificial Sequence
<220> FEATURE:
<223> OTHER INFORMATION: synthetic primer

<400> SEQUENCE: 19
ccacctctat caggaagaaa         20

<210> SEQ ID NO 20
<211> LENGTH: 20
<212> TYPE: DNA
<213> ORGANISM: Artificial Sequence
<220> FEATURE:
<223> OTHER INFORMATION: synthetic primer

<400> SEQUENCE: 20
ctgcaccgaa gatatcttca         20

<210> SEQ ID NO 21
<211> LENGTH: 20
<212> TYPE: DNA
<213> ORGANISM: Artificial Sequence
<220> FEATURE:
<223> OTHER INFORMATION: synthetic primer

<400> SEQUENCE: 21
gttgtacggg cctgacattt         20

<210> SEQ ID NO 22
<211> LENGTH: 19
<212> TYPE: DNA

```
<213> ORGANISM: Artificial Sequence
<220> FEATURE:
<223> OTHER INFORMATION: synthetic primer

<400> SEQUENCE: 22
ggtcctgtgc atggatgag                                               19

<210> SEQ ID NO 23
<211> LENGTH: 19
<212> TYPE: DNA
<213> ORGANISM: Artificial Sequence
<220> FEATURE:
<223> OTHER INFORMATION: synthetic primer

<400> SEQUENCE: 23
cacacgctgc cttgtgtct                                               19

<210> SEQ ID NO 24
<211> LENGTH: 19
<212> TYPE: DNA
<213> ORGANISM: Artificial Sequence
<220> FEATURE:
<223> OTHER INFORMATION: synthetic primer

<400> SEQUENCE: 24
ggtcagcaaa agcacggtt                                               19

<210> SEQ ID NO 25
<211> LENGTH: 23
<212> TYPE: DNA
<213> ORGANISM: Artificial Sequence
<220> FEATURE:
<223> OTHER INFORMATION: synthetic primer

<400> SEQUENCE: 25
tggtcaagaa acatttcaac gcc                                          23

<210> SEQ ID NO 26
<211> LENGTH: 23
<212> TYPE: DNA
<213> ORGANISM: Artificial Sequence
<220> FEATURE:
<223> OTHER INFORMATION: synthetic primer

<400> SEQUENCE: 26
ggtgaggatc tctggttttg gta                                          23

<210> SEQ ID NO 27
<211> LENGTH: 21
<212> TYPE: DNA
<213> ORGANISM: Artificial Sequence
<220> FEATURE:
<223> OTHER INFORMATION: synthetic primer

<400> SEQUENCE: 27
actgcaagaa acggttttcc c                                            21

<210> SEQ ID NO 28
<211> LENGTH: 20
<212> TYPE: DNA
<213> ORGANISM: Artificial Sequence
<220> FEATURE:
<223> OTHER INFORMATION: synthetic primer

<400> SEQUENCE: 28
ggcgaggaac actgagatgt                                              20
```

<210> SEQ ID NO 29
<211> LENGTH: 23
<212> TYPE: DNA
<213> ORGANISM: Artificial Sequence
<220> FEATURE:
<223> OTHER INFORMATION: synthetic primer

<400> SEQUENCE: 29
attgcacatc agactttgag gaa                                            23

<210> SEQ ID NO 30
<211> LENGTH: 20
<212> TYPE: DNA
<213> ORGANISM: Artificial Sequence
<220> FEATURE:
<223> OTHER INFORMATION: synthetic primer

<400> SEQUENCE: 30
ataatggccg tgtcgcttcg                                                20

<210> SEQ ID NO 31
<211> LENGTH: 20
<212> TYPE: DNA
<213> ORGANISM: Artificial Sequence
<220> FEATURE:
<223> OTHER INFORMATION: synthetic primer

<400> SEQUENCE: 31
agcgggtgaa atacaccaag                                                20

<210> SEQ ID NO 32
<211> LENGTH: 20
<212> TYPE: DNA
<213> ORGANISM: Artificial Sequence
<220> FEATURE:
<223> OTHER INFORMATION: synthetic primer

<400> SEQUENCE: 32
tcgctctcca tctcgagtct                                                20

<210> SEQ ID NO 33
<211> LENGTH: 19
<212> TYPE: DNA
<213> ORGANISM: Artificial Sequence
<220> FEATURE:
<223> OTHER INFORMATION: synthetic primer

<400> SEQUENCE: 33
tgtgaccagc aacacggtg                                                 19

<210> SEQ ID NO 34
<211> LENGTH: 20
<212> TYPE: DNA
<213> ORGANISM: Artificial Sequence
<220> FEATURE:
<223> OTHER INFORMATION: synthetic primer

<400> SEQUENCE: 34
acaacaggag agtagggcgc                                                20

<210> SEQ ID NO 35
<211> LENGTH: 22
<212> TYPE: DNA
<213> ORGANISM: Artificial Sequence
<220> FEATURE:

<223> OTHER INFORMATION: synthetic primer

<400> SEQUENCE: 35
cttgaacgga aagtggaatc ct                                    22

<210> SEQ ID NO 36
<211> LENGTH: 19
<212> TYPE: DNA
<213> ORGANISM: Artificial Sequence
<220> FEATURE:
<223> OTHER INFORMATION: synthetic primer

<400> SEQUENCE: 36
gtcaggcttg gaaacgtcc                                        19

<210> SEQ ID NO 37
<211> LENGTH: 25
<212> TYPE: DNA
<213> ORGANISM: Artificial Sequence
<220> FEATURE:
<223> OTHER INFORMATION: synthetic primer

<400> SEQUENCE: 37
cagtcatagg gagctgtcta ccaaa                                 25

<210> SEQ ID NO 38
<211> LENGTH: 20
<212> TYPE: DNA
<213> ORGANISM: Artificial Sequence
<220> FEATURE:
<223> OTHER INFORMATION: synthetic primer

<400> SEQUENCE: 38
gggtacacgc tgggaaacat                                       20

<210> SEQ ID NO 39
<211> LENGTH: 20
<212> TYPE: DNA
<213> ORGANISM: Artificial Sequence
<220> FEATURE:
<223> OTHER INFORMATION: synthetic primer

<400> SEQUENCE: 39
ggaattgtct cagaatggtc                                       20

<210> SEQ ID NO 40
<211> LENGTH: 21
<212> TYPE: DNA
<213> ORGANISM: Artificial Sequence
<220> FEATURE:
<223> OTHER INFORMATION: synthetic primer

<400> SEQUENCE: 40
gtagttgctt ctaggaagga g                                     21

<210> SEQ ID NO 41
<211> LENGTH: 20
<212> TYPE: DNA
<213> ORGANISM: Artificial Sequence
<220> FEATURE:
<223> OTHER INFORMATION: synthetic primer

<400> SEQUENCE: 41
tgagagggaa atcgtgcgtg                                       20

<210> SEQ ID NO 42
<211> LENGTH: 21
<212> TYPE: DNA
<213> ORGANISM: Artificial Sequence
<220> FEATURE:
<223> OTHER INFORMATION: synthetic primer

<400> SEQUENCE: 42
ttgctgatcc acatctgctg g                                    21

<210> SEQ ID NO 43
<211> LENGTH: 20
<212> TYPE: DNA
<213> ORGANISM: Artificial Sequence
<220> FEATURE:
<223> OTHER INFORMATION: synthetic primer

<400> SEQUENCE: 43
ctgccaccca gaagactgtg                                      20

<210> SEQ ID NO 44
<211> LENGTH: 20
<212> TYPE: DNA
<213> ORGANISM: Artificial Sequence
<220> FEATURE:
<223> OTHER INFORMATION: synthetic primer

<400> SEQUENCE: 44
ggtcctcagt gtagcccaag                                      20

<210> SEQ ID NO 45
<211> LENGTH: 20
<212> TYPE: DNA
<213> ORGANISM: Artificial Sequence
<220> FEATURE:
<223> OTHER INFORMATION: synthetic primer

<400> SEQUENCE: 45
cagcaaatcg gacaattcct                                      20

<210> SEQ ID NO 46
<211> LENGTH: 20
<212> TYPE: DNA
<213> ORGANISM: Artificial Sequence
<220> FEATURE:
<223> OTHER INFORMATION: synthetic primer

<400> SEQUENCE: 46
gccagcgacc aagtaaagag                                      20

<210> SEQ ID NO 47
<211> LENGTH: 19
<212> TYPE: DNA
<213> ORGANISM: Artificial Sequence
<220> FEATURE:
<223> OTHER INFORMATION: synthetic primer

<400> SEQUENCE: 47
gatgtcaatg ggggaggtt                                       19

<210> SEQ ID NO 48
<211> LENGTH: 24
<212> TYPE: DNA
<213> ORGANISM: Artificial Sequence
<220> FEATURE:
<223> OTHER INFORMATION: synthetic primer

```
<400> SEQUENCE: 48
ctctgactgg taatggcaaa aata                                            24

<210> SEQ ID NO 49
<211> LENGTH: 20
<212> TYPE: DNA
<213> ORGANISM: Artificial Sequence
<220> FEATURE:
<223> OTHER INFORMATION: synthetic primer

<400> SEQUENCE: 49
aataagcagc atcagccaac                                                 20

<210> SEQ ID NO 50
<211> LENGTH: 20
<212> TYPE: DNA
<213> ORGANISM: Artificial Sequence
<220> FEATURE:
<223> OTHER INFORMATION: synthetic primer

<400> SEQUENCE: 50
tcaagttgga aggaccacat                                                 20

<210> SEQ ID NO 51
<211> LENGTH: 23
<212> TYPE: DNA
<213> ORGANISM: Artificial Sequence
<220> FEATURE:
<223> OTHER INFORMATION: synthetic primer

<400> SEQUENCE: 51
ggccgagttg gacctgaaca tga                                             23

<210> SEQ ID NO 52
<211> LENGTH: 23
<212> TYPE: DNA
<213> ORGANISM: Artificial Sequence
<220> FEATURE:
<223> OTHER INFORMATION: synthetic primer

<400> SEQUENCE: 52
gaagttggcg ttggtgcggt cta                                             23

<210> SEQ ID NO 53
<211> LENGTH: 20
<212> TYPE: DNA
<213> ORGANISM: Artificial Sequence
<220> FEATURE:
<223> OTHER INFORMATION: synthetic primer

<400> SEQUENCE: 53
tcttcaagcc atcctgtgtg                                                 20

<210> SEQ ID NO 54
<211> LENGTH: 20
<212> TYPE: DNA
<213> ORGANISM: Artificial Sequence
<220> FEATURE:
<223> OTHER INFORMATION: synthetic primer

<400> SEQUENCE: 54
atccgcataa tctgcatggt                                                 20

<210> SEQ ID NO 55
<211> LENGTH: 21
```

```
<212> TYPE: DNA
<213> ORGANISM: Artificial Sequence
<220> FEATURE:
<223> OTHER INFORMATION: synthetic primer

<400> SEQUENCE: 55
cttgtcatgc tgctcctcct g                                                 21

<210> SEQ ID NO 56
<211> LENGTH: 21
<212> TYPE: DNA
<213> ORGANISM: Artificial Sequence
<220> FEATURE:
<223> OTHER INFORMATION: synthetic primer

<400> SEQUENCE: 56
tgcgactcct cacatctctg c                                                 21

<210> SEQ ID NO 57
<211> LENGTH: 20
<212> TYPE: DNA
<213> ORGANISM: Artificial Sequence
<220> FEATURE:
<223> OTHER INFORMATION: synthetic primer

<400> SEQUENCE: 57
cctggggtaa aagcagtgaa                                                   20

<210> SEQ ID NO 58
<211> LENGTH: 20
<212> TYPE: DNA
<213> ORGANISM: Artificial Sequence
<220> FEATURE:
<223> OTHER INFORMATION: synthetic primer

<400> SEQUENCE: 58
tgggatttag gcatcgttgt                                                   20

<210> SEQ ID NO 59
<211> LENGTH: 20
<212> TYPE: DNA
<213> ORGANISM: Artificial Sequence
<220> FEATURE:
<223> OTHER INFORMATION: synthetic primer

<400> SEQUENCE: 59
gttctcaagg cacaggtctc                                                   20

<210> SEQ ID NO 60
<211> LENGTH: 23
<212> TYPE: DNA
<213> ORGANISM: Artificial Sequence
<220> FEATURE:
<223> OTHER INFORMATION: synthetic primer

<400> SEQUENCE: 60
gcaggtcact tatgtcactt atc                                               23

<210> SEQ ID NO 61
<211> LENGTH: 23
<212> TYPE: DNA
<213> ORGANISM: Artificial Sequence
<220> FEATURE:
<223> OTHER INFORMATION: synthetic primer

<400> SEQUENCE: 61
```
aatctgtacc tgtcctgcgt gtt                                              23

<210> SEQ ID NO 62
<211> LENGTH: 26
<212> TYPE: DNA
<213> ORGANISM: Artificial Sequence
<220> FEATURE:
<223> OTHER INFORMATION: synthetic primer

<400> SEQUENCE: 62
tgggtaattt ttgggatcta cactct                                           26

<210> SEQ ID NO 63
<211> LENGTH: 22
<212> TYPE: DNA
<213> ORGANISM: Artificial Sequence
<220> FEATURE:
<223> OTHER INFORMATION: synthetic primer

<400> SEQUENCE: 63
cccagggacc tctctctaat ca                                               22

<210> SEQ ID NO 64
<211> LENGTH: 19
<212> TYPE: DNA
<213> ORGANISM: Artificial Sequence
<220> FEATURE:
<223> OTHER INFORMATION: synthetic primer

<400> SEQUENCE: 64
agctgcccct cagcttgag                                                   19

<210> SEQ ID NO 65
<211> LENGTH: 21
<212> TYPE: DNA
<213> ORGANISM: Artificial Sequence
<220> FEATURE:
<223> OTHER INFORMATION: synthetic primer

<400> SEQUENCE: 65
ccagtagtga gaaagggtcg c                                                21

<210> SEQ ID NO 66
<211> LENGTH: 20
<212> TYPE: DNA
<213> ORGANISM: Artificial Sequence
<220> FEATURE:
<223> OTHER INFORMATION: synthetic primer

<400> SEQUENCE: 66
agggcttggg gcaaattgtt                                                  20

<210> SEQ ID NO 67
<211> LENGTH: 21
<212> TYPE: DNA
<213> ORGANISM: Artificial Sequence
<220> FEATURE:
<223> OTHER INFORMATION: synthetic primer

<400> SEQUENCE: 67
ggtacatcct cgacggcatc t                                                21

<210> SEQ ID NO 68
<211> LENGTH: 21
<212> TYPE: DNA
<213> ORGANISM: Artificial Sequence

```
<220> FEATURE:
<223> OTHER INFORMATION: synthetic primer

<400> SEQUENCE: 68
gtgcctcttt gctgctttca c                                              21

<210> SEQ ID NO 69
<211> LENGTH: 20
<212> TYPE: DNA
<213> ORGANISM: Artificial Sequence
<220> FEATURE:
<223> OTHER INFORMATION: synthetic primer

<400> SEQUENCE: 69
attacgtccg ttaccgtctg                                                20

<210> SEQ ID NO 70
<211> LENGTH: 20
<212> TYPE: DNA
<213> ORGANISM: Artificial Sequence
<220> FEATURE:
<223> OTHER INFORMATION: synthetic primer

<400> SEQUENCE: 70
taggctcttc attggctcag                                                20

<210> SEQ ID NO 71
<211> LENGTH: 20
<212> TYPE: DNA
<213> ORGANISM: Artificial Sequence
<220> FEATURE:
<223> OTHER INFORMATION: synthetic primer

<400> SEQUENCE: 71
cttctctgca gcacatccac                                                20

<210> SEQ ID NO 72
<211> LENGTH: 20
<212> TYPE: DNA
<213> ORGANISM: Artificial Sequence
<220> FEATURE:
<223> OTHER INFORMATION: synthetic primer

<400> SEQUENCE: 72
agtactccag gcagcactcc                                                20

<210> SEQ ID NO 73
<211> LENGTH: 23
<212> TYPE: DNA
<213> ORGANISM: Artificial Sequence
<220> FEATURE:
<223> OTHER INFORMATION: synthetic primer

<400> SEQUENCE: 73
gactttaagg gttacctggg ttg                                            23

<210> SEQ ID NO 74
<211> LENGTH: 21
<212> TYPE: DNA
<213> ORGANISM: Artificial Sequence
<220> FEATURE:
<223> OTHER INFORMATION: synthetic primer

<400> SEQUENCE: 74
tcacatgcgc cttgatgtct g                                              21
```

<210> SEQ ID NO 75
<211> LENGTH: 20
<212> TYPE: DNA
<213> ORGANISM: Artificial Sequence
<220> FEATURE:
<223> OTHER INFORMATION: synthetic primer

<400> SEQUENCE: 75
ggcggtgacc tcacaagtat                                              20

<210> SEQ ID NO 76
<211> LENGTH: 20
<212> TYPE: DNA
<213> ORGANISM: Artificial Sequence
<220> FEATURE:
<223> OTHER INFORMATION: synthetic primer

<400> SEQUENCE: 76
acgaagccat ttggtaaacg                                              20

<210> SEQ ID NO 77
<211> LENGTH: 21
<212> TYPE: DNA
<213> ORGANISM: Artificial Sequence
<220> FEATURE:
<223> OTHER INFORMATION: synthetic primer

<400> SEQUENCE: 77
tggacagact aggaattggc a                                            21

<210> SEQ ID NO 78
<211> LENGTH: 22
<212> TYPE: DNA
<213> ORGANISM: Artificial Sequence
<220> FEATURE:
<223> OTHER INFORMATION: synthetic primer

<400> SEQUENCE: 78
ccagtccgtc aacatcaaaa ct                                           22

<210> SEQ ID NO 79
<211> LENGTH: 18
<212> TYPE: DNA
<213> ORGANISM: Artificial Sequence
<220> FEATURE:
<223> OTHER INFORMATION: synthetic primer

<400> SEQUENCE: 79
cgtggccgca gatttgaa                                                18

<210> SEQ ID NO 80
<211> LENGTH: 22
<212> TYPE: DNA
<213> ORGANISM: Artificial Sequence
<220> FEATURE:
<223> OTHER INFORMATION: synthetic primer

<400> SEQUENCE: 80
cttccattac ggagagatcc ac                                           22

<210> SEQ ID NO 81
<211> LENGTH: 19
<212> TYPE: DNA
<213> ORGANISM: Artificial Sequence
<220> FEATURE:
<223> OTHER INFORMATION: synthetic primer

<400> SEQUENCE: 81
cccagcatct gcaaagctc                                                    19

<210> SEQ ID NO 82
<211> LENGTH: 20
<212> TYPE: DNA
<213> ORGANISM: Artificial Sequence
<220> FEATURE:
<223> OTHER INFORMATION: synthetic primer

<400> SEQUENCE: 82
gtcaatgtac agctgccgca                                                   20

<210> SEQ ID NO 83
<211> LENGTH: 21
<212> TYPE: DNA
<213> ORGANISM: Artificial Sequence
<220> FEATURE:
<223> OTHER INFORMATION: synthetic primer

<400> SEQUENCE: 83
catgtacgtt gctatccagg c                                                 21

<210> SEQ ID NO 84
<211> LENGTH: 21
<212> TYPE: DNA
<213> ORGANISM: Artificial Sequence
<220> FEATURE:
<223> OTHER INFORMATION: synthetic primer

<400> SEQUENCE: 84
ctccttaatg tcacgcacga t                                                 21

<210> SEQ ID NO 85
<211> LENGTH: 20
<212> TYPE: DNA
<213> ORGANISM: Artificial Sequence
<220> FEATURE:
<223> OTHER INFORMATION: synthetic primer

<400> SEQUENCE: 85
aatcccatca ccatcttcca                                                   20

<210> SEQ ID NO 86
<211> LENGTH: 20
<212> TYPE: DNA
<213> ORGANISM: Artificial Sequence
<220> FEATURE:
<223> OTHER INFORMATION: synthetic primer

<400> SEQUENCE: 86
tggactccac gacgtactca                                                   20

<210> SEQ ID NO 87
<211> LENGTH: 38
<212> TYPE: DNA
<213> ORGANISM: Artificial Sequence
<220> FEATURE:
<223> OTHER INFORMATION: synthetic primer

<400> SEQUENCE: 87
aaaaaagcag gctcgagcca ccatggtgag caagggcc                               38

<210> SEQ ID NO 88

```
<211> LENGTH: 34
<212> TYPE: DNA
<213> ORGANISM: Artificial Sequence
<220> FEATURE:
<223> OTHER INFORMATION: synthetic primer

<400> SEQUENCE: 88
agaaagctgg gtctagaatt acgccagaat gcgt                              34
```

NANOPARTICLE, PREPARATION PROCESS AND USES THEREOF

CROSS-REFERENCE TO RELATED APPLICATION

This application claims priority of U.S. provisional patent application No. 62/912,852, filed on Oct. 9, 2019, the content of which is incorporated herein in its entirety by reference.

BACKGROUND OF THE INVENTION

1. Field of the Invention

The present invention relates to a nanoparticle, a preparation process thereof, a method for treating cancer, a method for enhancing effect of a liver cancer drug, a method for ameliorating tumor hypoxia, and a method for enhancing effect of a liver cancer vaccine by using the nanoparticle.

2. The Prior Art

According to the American Cancer Society, liver cancer is the second leading cause of death in men. According to the National Cancer Institute, the 5-year survival rate of liver cancer from 2007 to 2013 was only 17.6% in the United States. In Taiwan, there were 11,358 new cases of liver cancer in 2014 and 8,179 deaths from liver cancer. Due to the high incidence and low survival rate of liver cancer, it is necessary to develop a strategy for the effective treatment of liver cancer.

A well-established aspect of the tumor microenvironment (TME) is the formation of blood vessels, which sustain tumor growth; however, an imbalance between pro-angiogenic and anti-angiogenic signalling leads to vascular abnormalities. The TME composed of abnormal neovessels contributes to multiple aspects of malignant progression, such as metastasis and immunosuppression, and drives resistance to chemotherapy and cancer immunotherapy. Modulation of the TME by normalizing the tumor vascular function is emerging as a therapeutic strategy to improve anti-cancer efficacy when combined with cytotoxic therapeutics.

Anti-angiogenic therapy targeting neovessel formation holds promise for treating cancer. However, it only initially reduces tumor vessels and provides a modest survival benefit. The treatment is also associated with significant adverse effects, including the induction of tumor hypoxia, recruitment of pro-angiogenic and pro-inflammatory stromal cells and a reduction in the penetration of chemotherapeutic drugs. As an alternative to simply reducing tumor vessels, several anti-angiogenic agents, such as bevacizumab, sorafenib and sunitinib, were also demonstrated to act as potential vessel normalizing agents. Treatment with anti-angiogenic drugs at low doses can transiently normalize tumor vessels, leading to improved vessel functionality and synergistically suppressing cancer progression when combined with chemotherapy. However, the dosage and dosing period of anti-angiogenic agents must be adjusted to achieve a delicate balance of angiogenic and anti-angiogenic properties for vessel normalization to occur. The application of the vessel normalization approach using anti-angiogenic agents in a clinical setting remains challenging due to their narrow normalization window. Therefore, there is an urgent need to identify new therapeutic agents for modulating tumor vessels.

Nitric oxide (NO), which is a multifunctional signalling molecule, plays a crucial role in mediating cancer formation and progression. High concentrations of NO generated upon chemotherapy directly induce cytotoxicity in various tumors. NO synthesized in endothelial cells not only mediates angiogenesis but also maintains vascular homeostasis and endothelial function. Creation of perivascular NO gradients may normalize tumor vessels, resulting in improved response to anti-cancer treatment. Despite the potential of this therapy for cancer treatment, developing a pharmacological NO-based therapy that has clinical utility to treat cancer remains a major challenge. Various organic (nitrate/nitrite and S-nitrosothiols) and inorganic (metal nitrosyl) compounds were synthesized as NO-delivery agents. However, the short half-life, low bioavailability and poor tumor targeting of most NO-delivery agents limit their efficacy in vivo. Therefore, researchers in the art are actively developing novel nitric oxide delivery agents for the treatment of cancer.

Nanoparticles (NPs) can be used clinically to deliver drugs (such as anticancer drugs) to target sites, and thus are considered to have high potential in the field of nanotechnology and medicine. In addition, the application of nanoparticles includes drug/gene delivery, photodynamic therapy, and MRI. The benefits of nanoparticles include tumor targeting ligands modifiability, low toxicity, and better pharmacokinetics compared to general drugs. However, conventional nanoparticles often suffer from poor biocompatibility, poor stability, and damage to normal tissues, and degradation before reaching the target site.

In order to solve the above problems, it is necessary to develop a novel nanoparticle which is excellent in biocompatibility and stability, does not cause damage to normal tissues, can treat cancer (e.g., hepatocellular carcinoma, HCC), enhance effect of a liver cancer drug, enhance effect of a liver cancer vaccine, and alleviate tumor hypoxia, so that it will bring about considerable breakthroughs in the technology of the field for the benefit of a large group of people in need thereof.

SUMMARY OF THE INVENTION

A primary objective of the present invention is to provide a nanoparticle, comprising a core comprising at least one nitric oxide donor, and the core is encapsulated in a polymer and a lipid through an oil-in-water single emulsion to form the nanoparticle.

Another objective of the present invention is to provide a method for preparing the aforementioned nanoparticle, comprising the steps of: (a) dissolving a core, a polymer and a lipid in an organic phase; (b) adding the organic phase to deionized water and performing ultrasonication, and then obtaining an emulsion through an oil-in-water single emulsion; and (c) subjecting the emulsion to a centrifugation and collecting a precipitate, followed by suspending the precipitate in a buffer to obtain the nanoparticle; wherein the core comprises at least one nitric oxide donor, and the core is encapsulated in the polymer and the lipid through the oil-in-water single emulsion.

According to an embodiment of the present invention, the nanoparticle has a particle diameter ranging from 107 nm to 131 nm.

According to an embodiment of the present invention, the at least one nitric oxide donor is a dinitrosyl iron complex (DNIC).

According to an embodiment of the present invention, the polymer is poly D,L-lactide-co-glycolic acid (PLGA).

According to an embodiment of the present invention, the lipid is an emulsifier or a stabilizer.

According to an embodiment of the present invention, the emulsifier is D-α-tocopherol polyethylene glycol 1000 succinate (TPGS); and the stabilizer is selected from the group consisting of 1,2-distearoyl-sn-glycero-3-phosphoethanolamine-N-[methoxy(polyethylene glycol)-2000] (DSPE-PEG2000), cholesterol, 1,2-dioleoyl-sn-glycero-3-phosphocholine (DOPC), and any combination thereof.

Another objective of the present invention is to provide a method for treating cancer, comprising administering to a subject in need thereof a pharmaceutical composition comprising an effective amount of the aforementioned nanoparticle.

According to an embodiment of the present invention, the cancer is a hepatocellular carcinoma (HCC).

According to an embodiment of the present invention, the nanoparticle continuously releases nitric oxide.

According to an embodiment of the present invention, the effective amount of the nanoparticle is at least 0.1 mg/kg.

Another objective of the present invention is to provide a method for enhancing effect of a liver cancer drug, comprising administering to a subject in need thereof an agonist comprising an effective amount of the aforementioned nanoparticle.

According to an embodiment of the present invention, the liver cancer drug is doxorubicin or a tumor necrosis factor-related apoptosis-inducing ligand (TRAIL).

Another objective of the present invention is to provide a method for ameliorating tumor hypoxia, comprising administering to a subject in need thereof a pharmaceutical composition comprising an effective amount of the aforementioned nanoparticle.

Another objective of the present invention is to provide a method for enhancing effect of a liver cancer vaccine, comprising administering to a subject in need thereof an agonist comprising an effective amount of the aforementioned nanoparticle.

In summary, the nanoparticles of the present invention have the effect on good biocompatibility and stability, no damage to normal tissues, treating cancer (e.g., hepatocellular carcinoma, HCC), enhancing effect of the liver cancer drug, enhancing effect of the liver cancer vaccine, and alleviation of tumor hypoxia. In addition, the nanoparticle of the present invention greatly improves the rapid half-life of a nitric oxide donor in organisms, and can continuously release nitric oxide for a long time. The nanoparticle of the present invention can be used as anti-cancer therapeutic agents, and is useful for suppressing tumors. The outstanding effects make it an adjuvant for cancer, improve the tumor microenvironment, and can greatly increase the efficacy of chemotherapy, immunotherapy and large molecular protein therapy. The nanoparticle of the present invention can also be loaded with different chemotherapeutics at the same time for common delivery.

BRIEF DESCRIPTION OF THE DRAWINGS

The following drawings form part of the present specification and are included here to further demonstrate some aspects of the present invention, which can be better understood by reference to one or more of these drawings, in combination with the detailed description of the embodiments presented herein.

DETAILED DESCRIPTION OF THE PREFERRED EMBODIMENT

Figure 1:
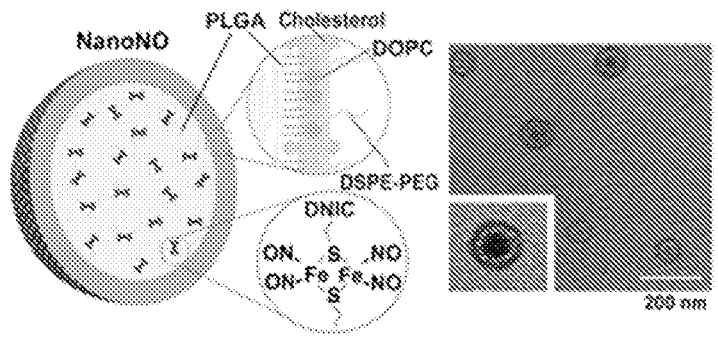
FIG. 1 is a schematic diagram and a transmission electron microscope image of a nanoparticle according to the present invention (i.e., NanoNO).

In the following detailed description of the embodiments of the present invention, reference is made to the accompanying drawings, which are shown to illustrate the specific embodiments in which the present disclosure may be practiced. These embodiments are provided to enable those skilled in the art to practice the present disclosure. It is understood that other embodiments may be used and that changes can be made to the embodiments without departing from the scope of the present invention. The following description is therefore not to be considered as limiting the scope of the present invention.

Definition

As used herein, the data provided represent experimental values that can vary within a range of ±20%, preferably within ±10%, and most preferably within ±5%.

As used herein, the term "nanoparticle" refers to a particle having a particle diameter less than 1 µm. Preferably, the nanoparticle of the present invention has a particle diameter between 107 nm and 131 nm.

As used herein, the term "agonist" refers to a molecule that directly, indirectly or substantially induces, promotes or enhances the biological activity or receptor activation of another molecule.

As used herein, the term "tumor hypoxia" refers to a physiological difference between the normal and the tumor tissue at the oxygen level, wherein the partial pressure of oxygen in the tumor tissue is reduced compared with that of the normal tissue.

According to the present invention, the pharmaceutical composition can be made into a dosage form suitable for parenteral or oral administration using techniques well known to those skilled in the art, including, but not limited to, injection (e.g., sterile aqueous solution or dispersion), sterile powder, tablet, troche, pill, capsule, and the like.

According to the present invention, the pharmaceutical composition can be administered by a parenteral route selected from the group consisting of: intraperitoneal injection, subcutaneous injection, intramuscular injection, intravenous injection, sublingual administration, and transdermal administration.

According to the present invention, the pharmaceutical composition may further comprise a pharmaceutically acceptable carrier widely used in pharmaceutically manufacturing techniques. For example, the pharmaceutically acceptable carrier can comprise one or more reagents selected from the group consisting of solvent, buffer, emulsifier, suspending agent, decomposer, disintegrating agent, dispersing agent, binding agent, excipient, stabilizing agent, chelating agent, diluent, gelling agent, preservative, wetting agent, lubricant, absorption delaying agent, liposome, and the like. The selection and quantity of these reagents falls within the professional literacy and routine technology of those skilled in the art.

According to the present invention, the pharmaceutically acceptable carrier comprises a solvent selected from the group consisting of water, normal saline, phosphate buffered saline (PBS), aqueous solution containing alcohol, and combinations thereof.

According to the present invention, statistical analyses were performed using GraphPad Prism 6. Student's t-tests or Mann-Whitney U tests were used to compare between two groups according to data distribution. One-way ANOVA followed by Tukey post hoc test was used to compare between 3 or more groups. Values were normally distributed, and the variance was similar between compared groups. A p-value of less than 0.05 was considered statistically significant.

The murine hepatocellular carcinoma (HCC) cell line HCA-1 and the human HCC cell lines JHH-7, Hep3B and human lung fibroblasts (HLF) were provided by Dr. Dan Duda (Massachusetts General Hospital, Boston). The human HCC cell line Mahlavu was provided by Dr. Han-Chung Wu (Academia Sinica, Taiwan). The human monocyte cell line THP-1 (ATCC® TIB-202™) was purchased from ATCC. HUVECs (BCRC H-UV001) were obtained from the Bioresource Collection and Research Center, Food Industry Research and Development Institute (Hsinchu, Taiwan). Cell lines were authenticated and tested for mycoplasma. HCA-1 and Mahlavu cells were cultured in high-glucose Dulbecco's modified Eagle's medium (DMEM); JHH-7 and HLF cells were cultured in DMEM/F12 medium; Hep3B cells were cultured in Minimum Essential Medium Alpha (MEMα) (Sigma-Aldrich, St. Louis, Mo.); THP-1 cells were maintained in RPMI-1640 (Corning, N.Y.). All media were supplemented with 10% fetal bovine serum (FBS) and 1% antibiotics (penicillin and streptomycin, HyClone, Logan, Utah). The HUVECs were cultured in Medium 199 (Sigma-Aldrich, St. Louis, Mo.) containing 20% FBS, ECGS (30 µg/mL), heparin (25 U/mL) and L-glutamine (2 mM). THP-1 cells were differentiated into macrophages by 72 h incubation with 20 ng/mL phorbol 12-myristate 13-acetate (PMA, Sigma-Aldrich, St. Louis, Mo.).

According to the present invention, poly D, L-lactide-co-glycolide (PLGA, 50/50, inherent viscosity: 0.17 dl/g) was purchased from Green Square Materials Incorporation (Taoyuan, Taiwan), and 1,2-distearoyl-sn-glycero-3-phosphoethanolamine-N-[methoxy(polyethylene glycol)-2000] (DSPE-PEG), cholesterol and 1,2-dioleoyl-sn-glycero-3-phosphocholine (DOPC) were purchased from Avanti Polar Lipids (Alabama, USA). D-α-tocopherol polyethylene glycol 1000 succinate (TPGS) and dimethyl sulfoxide (DMSO) were purchased from Sigma-Aldrich (St. Louis, Mo.).

Example 1

Preparation and Characteristics of Nanoparticles of Present Invention

Dinitrosyl iron complexes (DNICs)[Fe(µ-Set)$_2$(NO)$_4$](a DNIC encapsulated in the nanoparticles, which is a nitric oxide donor) and Fe(µ-SCH$_2$CH$_2$OH)$_2$(NO)$_4$ (free-form DNIC) were synthesized according to the methods described in Lu, T. T. et al. Anionic Roussin's red esters (RREs) syn-/anti-[Fe(mu-SEt)(NO)$_2$]$_2$(−): the critical role of thiolate ligands in regulating the transformation of RREs into dinitrosyl iron complexes and the anionic RREs. *Inorg. Chem.* 47, 6040-6050 (2008). Poly D, L-lactide-co-glycolide (PLGA, 50/50, inherent viscosity: 0.17 dl/g) was purchased from Green Square Materials Incorporation (Taoyuan, Taiwan), and 1,2-distearoyl-sn-glycero-3-phosphoethanolamine-N-[methoxy(polyethylene glycol)-2000] (DSPE-PEG), cholesterol and 1,2-dioleoyl-sn-glycero-3-phosphocholine (DOPC) were purchased from Avanti Polar Lipids (Alabama, USA). D-α-tocopherol polyethylene glycol 1000 succinate (TPGS) and dimethyl sulfoxide (DMSO) were purchased from Sigma-Aldrich (St. Louis, Mo.). NBD-DNIC [(NBD-NHCH$_2$CH$_2$S)Fe(NO)$_2$]$_2$ was synthesized according to the following procedure. Fe(NO)$_2$(tetramethylethylenediamine) (1 mmol) was added into the flask containing (NBD-NHCH$_2$CH$_2$SH) (1 mmol). The mixture solution was stirred for 60 minutes and the solvent was removed under reduced pressure. The resulting dark brown solid was purified by recrystallization from THF/Hexane. Yield: 0.292 g, 91.4%. FTIR (THF) 1812(w), 1779(vs), 1752(s) cm$^{-1}$ ($v_{NO}$).

The nanoparticle (i.e., NanoNO) formulation was prepared and characterized according to the following procedure. NanoNO was prepared through an oil-in-water single emulsion. PLGA (0.75 mg), DSPE-PEG (0.0807 mg), D-α-tocopherol polyethylene glycol 1000 succinate (TPGS) (0.375 mg), cholesterol (0.0375 mg), 1,2-dioleoyl-sn-glycero-3-phosphocholine (DOPC) (0.0375 mg) and DNIC (0.15 mg) were dissolved in 63 µL organic phase. The organic phase was added into 441 µL deionized water dropwise (volume ratio of oil and water=1/7). NanoNO was formed with 20 cycles of sonication for a total of 1 min 40 sec on ice. Each cycle included 5 sec of sonication pulse followed by a pulse off period of 5 sec (power 40 W) by a Q125 sonicator (Qsonica, Newtown, Conn., USA). To obtain NanoNO, the emulsion was centrifuged at 25,001 rcf for 20 min at 25° C. The resulting pellet of NanoNO was resuspended in PBS for further study. The nanoparticle size and surface charge were determined by a Zetasizer (300HS, Malvern Instruments Ltd., Worcestershire, UK). Transmission electron microscopy (H-7500, Hitachi High-Tech, Tokyo, Japan) was used to examine the size and morphology of NanoNO.

FIG. 1 is a schematic diagram and a transmission electron microscope image of NanoNO. Scale bar, 200 nm. Sizes, polydispersity index, zeta potentials (Zeta) and encapsulation efficacies of NanoNO. Data show the mean±s.e.m. from 5 experiments. PDI: polydispersity index; EE: encapsulation efficacies; Zeta: zeta potentials.

TABLE 1

| NanoNO | |
|---|---|
| Size (nm) | 119 ± 12 |
| PDI | 0.146 ± 0.030 |
| Zeta (mV) | −23 ± 3 |
| EE (%) | 80 ± 5 |

As shown in FIG. 1 and Table 1, NanoNO was assembled by the encapsulation of a DNIC [Fe(μ-SEt)$_2$(NO)$_4$] into lipid-PLGA nanoparticles (NPs) (FIG. 1). Transmission electron microscope and dynamic light scattering analyses showed that NanoNO comprised well-dispersed spheres, with average diameters of 119±12 nm, and a polydispersity index (PDI) of 0.146±0.030 (FIG. 1). The encapsulation efficacy (EE) of DNIC was approximately 80±5%.

Example 2

Stability of Free DNIC and DNIC Loaded in NanoNO

Free DNIC and NanoNO were suspended with PBS buffer or acetic buffer (pH 4.0 or 5.5) and then incubated at 37° C. in a 200 rpm Orbital Shaker. At different time points, the solution was harvested, dissolved in DMSO and analysed by a UV spectrophotometer at 360 nm.

Figure 2A:
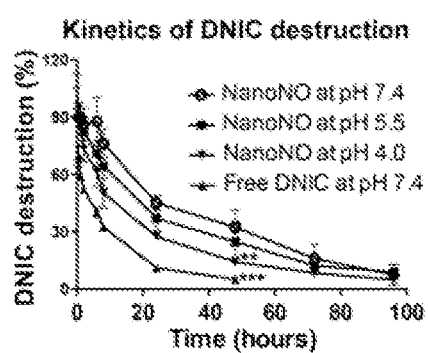
FIG. 2A is a kinetic profile of DNIC destruction from free-form DNIC and the nanoparticle of the present invention (i.e., NanoNO) under different pH conditions.

The kinetic profile for the decomposition of DNIC and the concomitant release of NO from NanoNO were evaluated under physiological and acidic pH conditions at 37° C. FIG. 2A is a kinetic profile of DNIC destruction from free-form DNIC and the nanoparticle of the present invention (i.e., NanoNO) under different pH conditions. Free-form DNIC and NanoNO were incubated in a PBS buffer or acetic buffer at a pH of 4.0-7.4, and DNIC destruction was measured using a UV spectrophotometer at 360 nm (n=5 independent samples). The results are expressed as percentage of the initial DNIC. P=0.0094 and *P=0.0004 compared to NanoNO at a pH of 7.4.

Figure 2B:
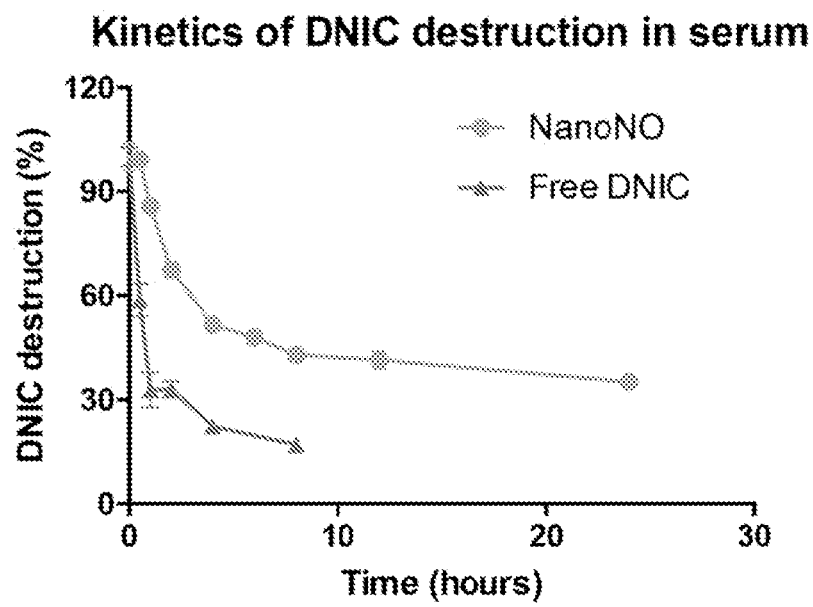
FIG. 2B is a kinetic profile of DNIC destruction from free-form DNIC and NanoNO in serum.

FIG. 2B is a kinetic profile of DNIC destruction from free-form DNIC and NanoNO in serum (pH 7.4). Free-form DNIC and NanoNO were incubated in PBS containing 10% fetal bovine serum at 37° C. DNIC destruction was measured using a UV spectrophotometer at 360 nm. The results are expressed as the percentage of the initial DNIC (n=3 samples). All data are shown as the mean value± the s.e.m. As shown in FIGS. 2A and 2B, the encapsulation of DNIC into NanoNO improved its stability, with an extended half-life of 24.4±2.5 h, compared to the 3.9±1.5 h exhibited by free-form DNIC under physiological conditions (pH of 7.4). Furthermore, the decomposition rate of DNIC in the form of NanoNO under physiological conditions was slower than that observed under acidic conditions (pH of 4.0) (FIG. 2A). This difference may be attributed to the different degradation rates of PLGA and the stabilities of DNIC loaded in NanoNO under different pH conditions. This pH-dependent decomposition of NanoNO signifies the efficient release of NO from NanoNO in acidic endosomes/lysosomes while also penetrating the tumor microenvironment (TME) or entering cancer cells.

Example 3

Evaluation of Effect of NanoNO on Cumulative Release of Nitric Oxide (NO)

The cumulative release of NO from NanoNO over time was assessed using an NO-specific 4,5-diamino-N,N,N',N'-tetraethylrhodamine (DAR-1) fluorescence probe.

The release profile of NO from free DNIC or NanoNO was investigated at pH 7.4 at 37° C. Briefly, free DNIC and NanoNO were suspended with PBS buffer. DAR-1 at a final concentration of 20 μM was added to the solution and then incubated at 37° C. on a 200 rpm orbital shaker. At different time points, the solution was harvested, and the fluorescence intensity (excitation at 560 nm, emission at 595 nm) was measured using a microplate reader (Spark 10M, Tecan, Germany).

Figure 3:
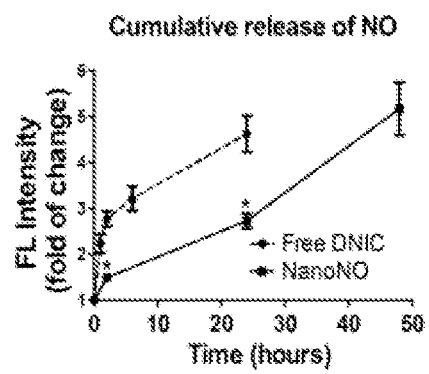
FIG. 3 is a data diagram of the effect of NanoNO on the cumulative release of nitric oxide.

FIG. 3 is a data diagram of the effect of NanoNO on the cumulative release of nitric oxide. NO release from free-form DNIC and NanoNO under physiological conditions (pH of 7.4). Free-form DNIC and NanoNO were incubated in PBS buffer at pH 7.4, and the release of NO was measured as the fluorescence intensity (excitation at 560 nm and emission at 595 nm) of the NO-specific probe DAR-1. The results are expressed as a fold change compared to time 0 (free DNIC, n=5; NanoNO; n=4 independent samples). *P=0.0159 compared to free DNIC. FL: fluorescence intensity.

As shown in FIG. 3, in contrast to the in vitro release of NO from free DNIC, which proceeded at a rapid rate during the first two hours, the steady release of NO from NanoNO occurred for a period of 2-48 h.

The above characteristics suggested that NanoNO may be ideal for the sustained delivery and controlled release of NO into tumors.

Example 4

Evaluation of Anti-Cancer Effect of NanoNO
4.1 In Vitro Experiment

Survival analysis was performed on the patients. NOS2 and NOS3 mRNA profiles in 319 HCC patients were derived from the Cancer Genome Atlas. The mRNA expression data and disease-free survival data were downloaded from the cBio portal. A patient's risk score was calculated as the sum of the mRNA expression levels of NOS2 and NOS3. Patients were classified in a high-expression or a low-expression group, with the median of the risk score as the threshold value. Survival curves for a high-expression and low-expression group were obtained using the Kaplan-Meier method and compared using the log-rank test (two-sided).

Figure 4A:
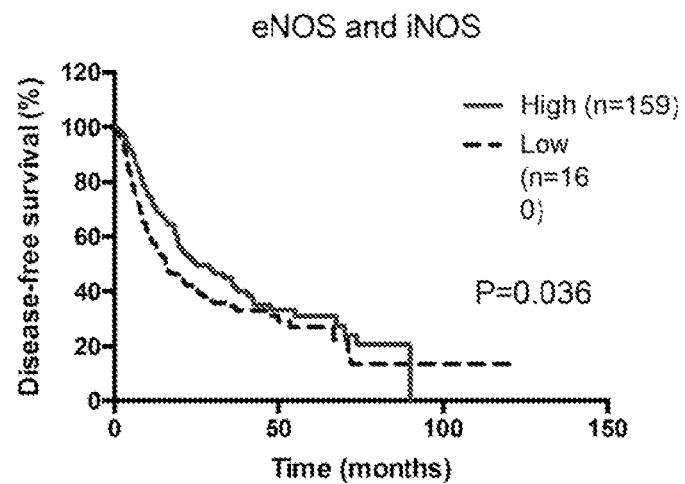
FIG. 4A is a data diagram of the effect of NanoNO on anticancer.
Figure 4B:
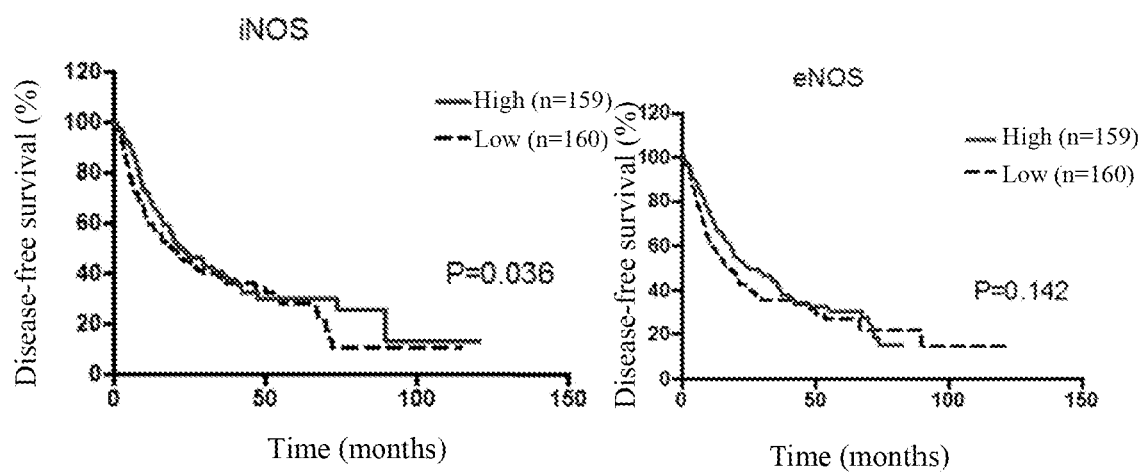
FIG. 4B is another data diagram of the effect of NanoNO on anticancer.

NO derived from inducible nitric oxide synthase (iNOS) and endothelial nitric oxide synthase (eNOS) in HCC may serve as an important modulator for tumor progression and angiogenesis. The analysis of the Cancer Genome Atlas database identifies a positive correlation between the eNOS and iNOS expressions and better disease-free survival (also named as relapse-free survival) (p=0.036) for HCC. It indicates the possible therapeutic benefit of NO delivery into HCC (FIGS. 4A and 4B, and Table 2 and Table 3, wherein FIGS. 4A and 4B show that the overall expression level of the gene is higher or lower). In FIG. 4B, although not significant, eNOS or iNOS expression was associated with increased disease-free survival (DFS) (P=0.142, P=0.169, respectively) for HCC. The comparison of survival curves was performed using a log-rank Mantel-Cox test (two-sided).

The procedure of reverse transcription quantitative real time PCR was as follows. Total RNA was extracted from HUVECs or flow-sorted tumor-associated macrophages using the RNeasy Mini Kit (Qiagen, Calif., USA). cDNAs were synthesized using the High-Capicity cDNA Reverse Transcription Kit (Applied Biosystems, Calif., USA). Primers specific for Arignase-1, CCL17, CCL22, IL10, MRC1, CXCL9, IL-1β, TNF-α, CXCL-11, NOS2, NOS3, Snail, Slug, Zeb1, Zeb2, Trim28, Fibronectin, Vimentin, E-cadherin, PD-L1, S1PR1, ANGPT1, PDGF-B, VEGFA, ANGPT2, EGF, IL-6, PPARγ, TGFβ, GAPDH and β-actin were used (Table 2), and relative gene expression was determined using Real-Time SYBR Green PCR Master Mix (Applied Biosystems, Calif., USA) on a QPCR System. The comparative threshold cycle method was used to calculate fold change in gene expression, which was normalized to β-actin.

TABLE 2

| Name | Sequence |
| --- | --- |
| mArg 1 | For: 5' CAACCAGCTCTGGGAATCTG 3' (SEQ ID NO: 1)<br>Rev: 5' AATCGGCCTTTTCTTCCTTC 3' (SEQ ID NO: 2) |
| mCCL17 | For: 5' TGCTTCTGGGGACTTTTCTG 3' (SEQ ID NO: 3)<br>Rev: 5' TGGCCTTCTTCACATGTTTG 3' (SEQ ID NO: 4) |
| mCCL22 | For: 5' GTCCTTCTTGCTGTGGCAAT 3' (SEQ ID NO: 5)<br>Rev: 5' ACGGTTATCAAAACAACGCC 3' (SEQ ID NO: 6) |
| mIL-10 | For: 5' CCAGAGCCACATGCTCCTA 3' (SEQ ID NO: 7)<br>Rev: 5' AGGGGAGAAATCGATGACAG 3' (SEQ ID NO: 8) |
| mMRC-1 | For: 5' CCTGAACAGCAACTTGACCA 3' (SEQ ID NO: 9)<br>Rev: 5' GCAATGGCCATAGAAAGGAA 3' (SEQ ID NO: 10) |
| mCXCL-9 | For: 5 AGTGTGGAGTTCGAGGAACC 3' (SEQ ID NO: 11)<br>Rev: 5' GAGTCCGGATCTAGGCAGG 3' (SEQ ID NO: 12) |
| mIL-1β | For: 5' TGCCACCTTTTGACAGTGAT 3' (SEQ ID NO: 13)<br>Rev: 5' TGTCCTCATCCTGGAAGGTC 3' (SEQ ID NO: 14) |
| mTNFα | For: 5' CCGATGGGTTGTACCTTGT 3' (SEQ ID NO: 15)<br>Rev: 5' CGGACTCCGCAAAGTCTAAG 3' (SEQ ID NO: 16) |
| mCXCL-11 | For: 5' AGCTGCTCAAGGCTTCCTTA 3' (SEQ ID NO: 17)<br>Rev: 5' AGTAACAATCACTTCAACTTTGTCG 3' (SEQ ID NO: 18) |
| mNOS2 | For: 5' CCACCTCTATCAGGAAGAAA 3' (SEQ ID NO: 19)<br>Rev: 5' CTGCACCGAAGATATCTTCA 3' (SEQ ID NO: 20) |
| mNOS3 | For: 5' GTTGTACGGGCCTGACATTT 3' (SEQ ID NO: 21)<br>Rev: 5' GGTCCTGTGCATGGATGAG 3' (SEQ ID NO: 22) |
| mSnail | For: 5' CACACGCTGCCTTGTGTCT 3' (SEQ ID NO: 23)<br>Rev: 5' GGTCAGCAAAAGCACGGTT 3' (SEQ ID NO: 24) |
| mSlug | For: 5' TGGTCAAGAAACATTTCAACGCC 3' (SEQ ID NO: 25)<br>Rev: 5' GGTGAGGATCTCTGGTTTTGGTA 3' (SEQ ID NO: 26) |

TABLE 2-continued

| Name | Sequence |
| --- | --- |
| mZeb1 | For: 5' ACTGCAAGAAACGGTTTTCCC 3' (SEQ ID NO: 27)<br>Rev: 5' GGCGAGGAACACTGAGATGT 3' (SEQ ID NO: 28) |
| mZeb2 | For: 5' ATTGCACATCAGACTTTGAGGAA 3' (SEQ ID NO: 29)<br>Rev: 5' ATAATGGCCGTGTCGCTTCG 3' (SEQ ID NO: 30) |
| mTrim28 | For: 5' AGCGGGTGAAATACACCAAG 3' (SEQ ID NO: 31)<br>Rev: 5' TCGCTCTCCATCTCGAGTCT 3' (SEQ ID NO: 32) |
| mFibronectin | For: 5' TGTGACCAGCAACACGGTG 3' (SEQ ID NO: 33)<br>Rev: 5' ACAACAGGAGAGTAGGGCGC 3' (SEQ ID NO: 34) |
| mVimentin | For: 5' CTTGAACGGAAAGTGGAATCCT 3' (SEQ ID NO: 35)<br>Rev: 5' GTCAGGCTTGGAAACGTCC 3' (SEQ ID NO: 36) |
| mE-cadherin | For: 5' CAGTCATAGGGAGCTGTCTACCAAA 3' (SEQ ID NO: 37)<br>Rev: 5' GGGTACACGCTGGGAAACAT 3' (SEQ ID NO: 38) |
| mPD-L1 | For: 5' GGAATTGTCTCAGAATGGTC 3' (SEQ ID NO: 39)<br>Rev: 5' GTAGTTGCTTCTAGGAAGGAG 3' (SEQ ID NO: 40) |
| mβ-actin | For: 5 TGAGAGGGAAATCGTGCGTG 3' (SEQ ID NO: 41)<br>Rev: 5' TTGCTGATCCACATCTGCTGG 3' (SEQ ID NO: 42) |
| mGAPDH | For: 5' CTGCCACCCAGAAGACTGTG 3' (SEQ ID NO: 43)<br>Rev: 5' GGTCCTCAGTGTAGCCCAAG 3' (SEQ ID NO: 44) |
| hS1PR1 | For: 5' CAGCAAATCGGACAATTCCT 3' (SEQ ID NO: 45)<br>Rev: 5' GCCAGCGACCAAGTAAAGAG 3' (SEQ ID NO: 46) |
| hANGPT1 | For: 5' GATGTCAATGGGGAGGTT 3' (SEQ ID NO: 47)<br>Rev: 5' CTCTGACTGGTAATGGCAAAAATA 3' (SEQ ID NO: 48) |
| hANGPT2 | For: 5' AATAAGCAGCATCAGCCAAC 3' (SEQ ID NO: 49)<br>Rev: 5' TCAAGTTGGAAGGACCACAT 3' (SEQ ID NO: 50) |
| hPDGF-B | For: 5' GGCCGAGTTGGACCTGAACATGA 3' (SEQ ID NO: 51)<br>Rev: 5' GAAGTTGGCGTTGGTGCGGTCTA 3' (SEQ ID NO: 52) |
| hVEGF-A | For: 5' TCTTCAAGCCATCCTGTGTG 3' (SEQ ID NO: 53)<br>Rev: 5' ATCCGCATAATCTGCATGGT 3' (SEQ ID NO: 54) |
| hEGF | For: 5' CTTGTCATGCTGCTCCTCCTG 3' (SEQ ID NO: 55)<br>Rev: 5' TGCGACTCCTCACATCTCTGC 3' (SEQ ID NO: 56) |

TABLE 2-continued

| Name | Sequence |
| --- | --- |
| hCXCL-11 | For: 5' CCTGGGGTAAAAGCAGTGAA 3' (SEQ ID NO: 57)<br>Rev: 5' TGGGATTTAGGCATCGTTGT 3' (SEQ ID NO: 58) |
| hNOS2 | For: 5' GTTCTCAAGGCACAGGTCTC 3' (SEQ ID NO: 59)<br>Rev: 5' GCAGGTCACTTATGTCACTTATC 3' (SEQ ID NO: 60) |
| hIL-1β | For: 5' AATCTGTACCTGTCCTGCGTGTT 3' (SEQ ID NO: 61)<br>Rev: 5' TGGGTAATTTTTGGGATCTACAC TCT 3' (SEQ ID NO: 62) |
| hTNF-α | For: 5' CCCAGGGACCTCTCTCTAATCA 3' (SEQ ID NO: 63)<br>Rev: 5' AGCTGCCCCTCAGCTTGAG 3' (SEQ ID NO: 64) |
| hCXCL-9 | For: 5' CCAGTAGTGAGAAAGGGTCGC 3' (SEQ ID NO: 65)<br>Rev: 5' AGGGCTTGGGGCAAATTGTT 3' (SEQ ID NO: 66) |
| hIL-6 | For: 5' GGTACATCCTCGACGGCATCT 3' (SEQ ID NO: 67)<br>Rev: 5' GTGCCTCTTTGCTGCTTTCAC 3' (SEQ ID NO: 68) |
| hCCL-22 | For: 5' ATTACGTCCGTTACCGTCTG 3' (SEQ ID NO: 69)<br>Rev: 5' TAGGCTCTTCATTGGCTCAG 3' (SEQ ID NO: 70) |
| hCCL-17 | For: 5' CTTCTCTGCAGCACATCCAC 3' (SEQ ID NO: 71)<br>Rev: 5' AGTACTCCAGGCAGCACTCC 3' (SEQ ID NO: 72) |
| hIL-10 | For: 5' GACTTTAAGGGTTACCTGGGTTG 3' (SEQ ID NO: 73)<br>Rev: 5' TCACATGCGCCTTGATGTCTG 3' (SEQ ID NO: 74) |
| hMRC-1 | For: 5' GGCGGTGACCTCACAAGTAT 3' (SEQ ID NO: 75)<br>Rev: 5' ACGAAGCCATTTGGTAAACG 3' (SEQ ID NO: 76) |
| hArginase-1 | For: 5' TGGACAGACTAGGAATTGGCA 3' (SEQ ID NO: 77)<br>Rev: 5' CCAGTCCGTCAACATCAAAACT 3' (SEQ ID NO: 78) |
| hPPAR-γ | For: 5' CGTGGCCGCAGATTTGAA 3' (SEQ ID NO: 79)<br>Rev: 5' CTTCCATTACGGAGAGATCCAC 3' (SEQ ID NO: 80) |
| hTGF-β | For: 5' CCCAGCATCTGCAAAGCTC 3' (SEQ ID NO: 81)<br>Rev: 5' GTCAATGTACAGCTGCCGCA 3' (SEQ ID NO: 82) |
| hβ-actin | For: 5' CATGTACGTTGCTATCCAGGC 3' (SEQ ID NO: 83)<br>Rev: 5' CTCCTTAATGTCACGCACGAT 3' (SEQ ID NO: 84) |
| hGAPDH | For: 5' AATCCCATCACCATCTTCCA 3' (SEQ ID NO: 85)<br>Rev: 5' TGGACTCCACGACGTACTCA 3' (SEQ ID NO: 86) |

In Table 3, iNOS was expressed at lower levels in HCA-1 mouse liver cancer cells, and at higher levels in normal FL83B hepatocytes (obtained from the Bioresource Collection and Research Center, Food Industry Research and Development Institute (BCRC 60325)). iNOS and eNOS mRNA expression levels in HCA-1 cells and FL83B hepatocytes were determined by quantitative PCR (n=4 biologically independent samples). All data are shown as the mean value± the s.e.m. Analysis was performed using two-tailed Mann-Whitney U test. *P=0.0286.

TABLE 3

| Gene | FL83B | HCA-1 |
| --- | --- | --- |
| iNOS | 1.71 ± 0.92 | 0.05 ± 0.01* |
| eNOS | Not determined | Not determined |

In Table 4, both iNOS and eNOS were expressed at lower levels in tumor tissues than in healthy liver tissues. Tissues were dissected from orthotopic HCA-1 HCC models. iNOS and eNOS mRNA expression levels were determined by quantitative PCR (n=5 mice). All data are shown as the mean value± the s.e.m. Analysis was performed using two-tailed Mann-Whitney U test. *P=0.0286, **P=0.0079.

TABLE 4

| Gene | Liver | Tumor |
| --- | --- | --- |
| iNOS | 1.58 ± 0.73 | 0.05 ± 0.02** |
| eNOS | 1.03 ± 0.14 | 0.06 ± 0.01* |

Subsequently, free DNIC and NanoNO cytotoxicity was measured. HCC cells and HUVECs were exposed to the free DNIC or NanoNO for 48 h in serum-free medium. After the treatment, 15 μL of 5 mg/mL 3-[4,5-Dimethylthiazol-2-yl]-2,5-diphenyltetrazolium bromide (MTT) reagent was added and incubated at 37° C. for 3 h. The medium was aspirated, and 50 μL of DMSO was added. The absorbance was measured at 570 nm using a UV-Vis scanner (Multiskan GO, Thermo, USA).

Figure 4C:
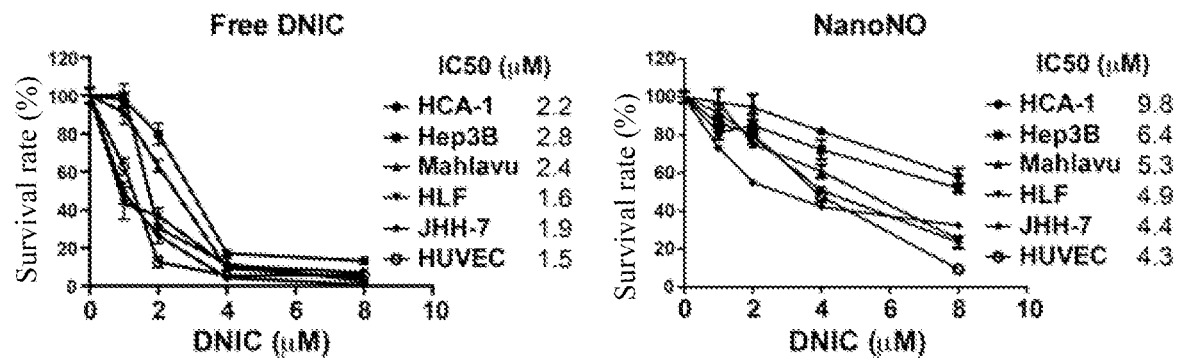
FIG. 4C is another data diagram of the effect of NanoNO on anticancer.

The cytotoxicity of free DNIC and its nanoscale formulation NanoNO were measured against HCC cell lines and human umbilical vein endothelial cells (HUVECs)—an endothelial cell model to study angiogenesis. Free DNIC showed cytotoxic activity in human HCC (Mahlavu, Hep3B, JHH-7 and HLF) and murine HCC (HCA-1) cell lines and HUVECs (FIG. 4C). In FIG. 4C, free-form DNIC and NanoNO exhibit cytotoxicity in HCC cells and HUVECs (n=5 biologically independent samples).

The cytotoxicity of NanoNO was found to exhibit $IC_{50}$ values that were twice as high as those of the free NO donor in most in vitro HCC cells. The reduced cytotoxicity in vitro may be due to the slow release of NO from NanoNO. Although limited direct cytotoxicity was observed in vitro with NanoNO, the inventors further investigated its potential for in vivo applications, where it can effectively deliver and undergo the sustained release of NO into HCC alongside other treatments to produce a synergistic anti-cancer effect.

4.2 In Vivo Experiment

The pharmacokinetics and biodistribution of NanoNO in orthotopic murine HCC models generated using HCA-1 were evaluated. C3H/HeNCrNarl male mice and nude male mice were purchased from the National Laboratory Animal Center (Taipei, Taiwan). Murine HCC HCA-1 cells were orthotopically implanted in the liver of 6-8-week-old male C3H mice as previously described. Human HCC JHH-7 cells were orthotopically implanted in the liver of 6-8-week-old male nude mice. All animals received humane care in compliance with the "Guide for the Care and Use of Laboratory Animals" published by the National Academy of Sciences, and all study procedures and protocols were approved by the Animal Research Committee of National Tsing-Hua University (Hsinchu, Taiwan).

The procedure of pharmacokinetic and tissue distribution study was as follows. C3H/HeNCrNarl male mice with orthotopic implants of HCA-1 cells were injected intravenously with free DNIC (10 mg/kg) or NanoNO (7.5 mg/kg). At different time points, 200 μL of blood was collected from the orbital sinus and mixed with 50 μL of 1000 U/mL heparin (Sigma, USA). For evaluation of tissue distribution, four hours after administration, the mice were sacrificed. The tissues were collected and homogenized in lysis buffer (10 mM Tris-HCl, 1% Triton X-100, 0.1% SDS, 0.1% SDC and 140 mM NaCl). The tissue lysates were kept on ice for 30 min and centrifuged at 25,001 rcf at 4° C. for 30 min, and the supernatants were collected. The DNIC signal was measured by electron paramagnetic resonance (EPR plus, Bruker, Germany). $HSCH_2CH_2OH$ (1 mM) was added to the serum or tissue lysates to transform all the DNICs into the EPR-active form for analysis. The DNIC concentration was calculated according to a standard curve obtained by the amounts of DNIC or NanoNO.

Figure 4D:
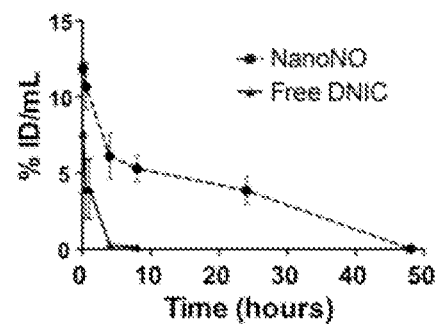
FIG. 4D is another data diagram of the effect of NanoNO on anticancer, in which ID/mL represents injected dose per mL.

FIG. 4D is another data diagram of the effect of NanoNO on anticancer, in which ID/mL represents injected dose per mL. FIG. 4D shows serum concentration profiles of DNIC in different formulations (free DNIC, n=5 mice; NanoNO, n=6 mice). As shown in FIG. 4D, NanoNO significantly prolonged the circulation of DNIC compared to free DNIC after intravenous administration.

Table 5 shows comparison of pharmacokinetic parameters of DNIC in different formulations (free DNIC and NanoNO) in C3H mice with orthotopic HCA-1 tumors. Non-compartmental analysis was employed for the pharmacokinetic parameter analysis. AUC, area under the curve; CL, clearance; h, hour; $t_{1/2}$, half-life; $V_{ss}$, steady state volume of distribution. The half-lives ($t_{1/2}$) of DNIC loaded NanoNO increased 25-fold compared with that of the free DNIC (Table 5).

TABLE 5

| | $t_{1/2}$ (h) | AUC (h × μg/ml) | CL (ml/h/kg) | $V_{ss}$ (ml/kg) |
|---|---|---|---|---|
| Free DNIC | 1.27 | 26.9 | 27.6 | 32.7 |
| NanoNO | 31.16 | 336.9 | 1.3 | 55.8 |

Figure 4E:
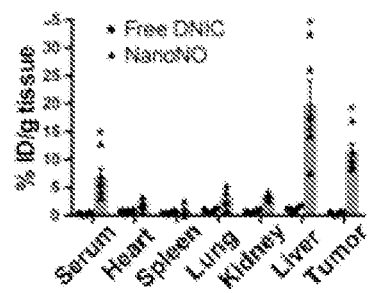
FIG. 4E is another data diagram of the effect of NanoNO on anticancer.

FIG. 4E shows tissue distribution of DNIC in different formulations (free DNIC, n=4 mice; NanoNO, n=5 mice). ID/g, injected dose per gram. *P=0.0159 compared to Free DNIC. Increased liver uptake of DNIC loaded in NanoNO was observed compared to free DNIC four hours after intravenous administration. More significantly, the use of NanoNO resulted in the high accumulation of DNIC in HCC tumors (FIG. 4E), whereas free-form DNIC was poorly delivered and accumulated in the tumor (FIG. 4E). These results suggest that NanoNO had significantly better tumor-targeting capabilities than free-form DNIC, but did not show obvious targeting capabilities for other organs (such as heart, spleen, lung and kidney).

Figure 4F:
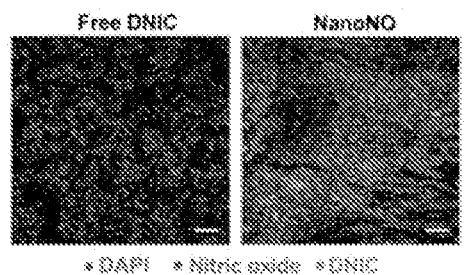
FIG. 4F is another data diagram of the effect of NanoNO on anticancer.

Next, NBD-labeled DNIC was used to track the intracellular delivery of free DNIC and NanoNO, and the NO-specific fluorescence probe DAR-1 was used to assess the penetration of NO released from free DNIC and NanoNO in HCC. In FIG. 4F, microphotographs of HCC tumors show DNIC uptake (green) and NO release (red) four hours after intravenous administration of NBD-DNIC loaded in NanoNO or free-form NBD-DNIC (7.5 mg/kg) to mice. 4',6-diamidino-2-phenylindole (DAPI, a fluorescent dye capable of binding strongly to DNA), blue. Scale bar, 50 μm. The experiments were repeated twice independently. As shown in FIG. 4F, the enhanced tumor uptake of NanoNO led to the increased penetration of NBD-labeled DNIC and release of NO in HCC tumors compared with free DNIC.

Figure 4G:
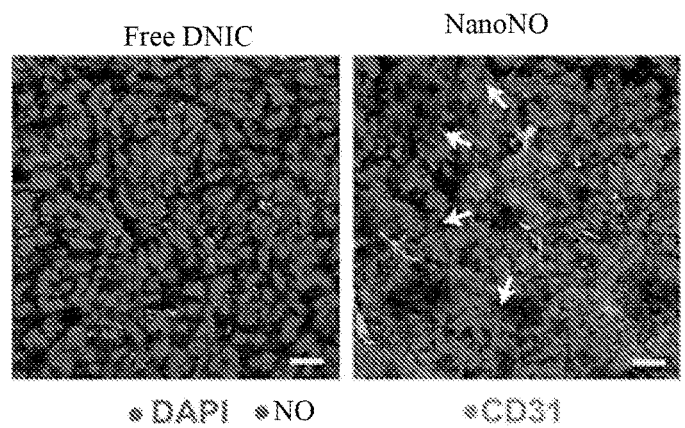
FIG. 4G is another data diagram of the effect of NanoNO on anticancer.

In FIG. 4G, NO released from NanoNO was localized in perivascular regions. NO release (red) was detected using DAR-1 in tumors four hours after intravenous administration of NanoNO or free-form DNIC (10 mg/kg) in mice. The arrowheads indicate perivascular NO gradients. Scale bar, 20 μm. The release of NO was imaged and quantified with a Zeiss LSM 780 confocal microscope (n=7 section images from four mice). The experiments were repeated twice independently.

As shown in FIGS. 4F and 4G, NO released from NBD-labeled DNIC/NanoNO was not only concentrated and partly colocalized with NBD-labeled DNIC/NanoNO in perivascular regions (adjacent to CD31 positive cells) but also penetrated into tumor tissues, resulting elevation in perivascular NO gradients.

Figure 4H:
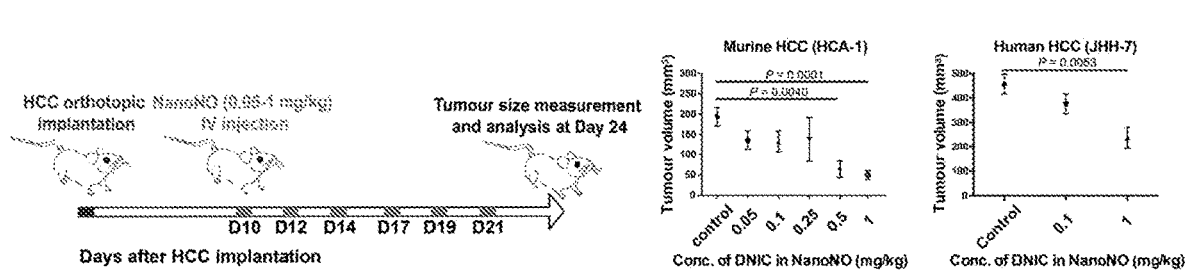
FIG. 4H is another data diagram of the effect of NanoNO on anticancer.
Figure 4I:
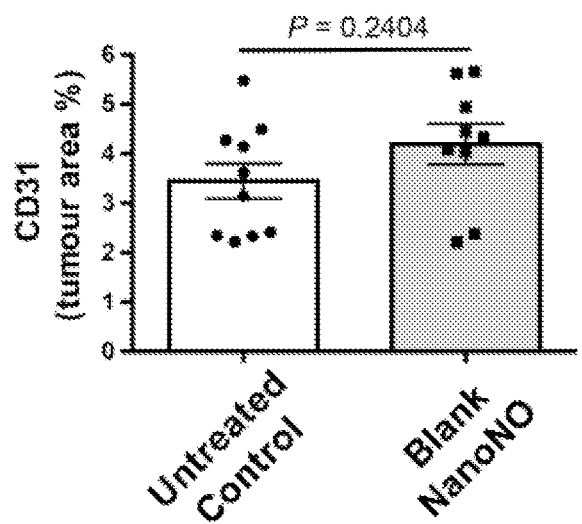
FIGS. 4Ia-4If are data diagrams of the effect of NanoNO on anticancer.
Figure 4I:
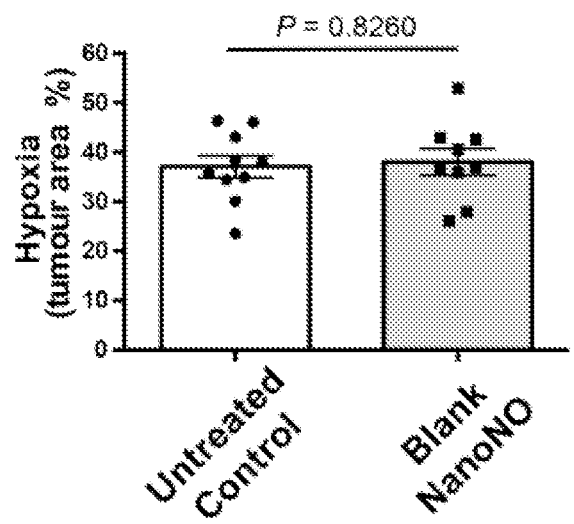
Figure 4I:
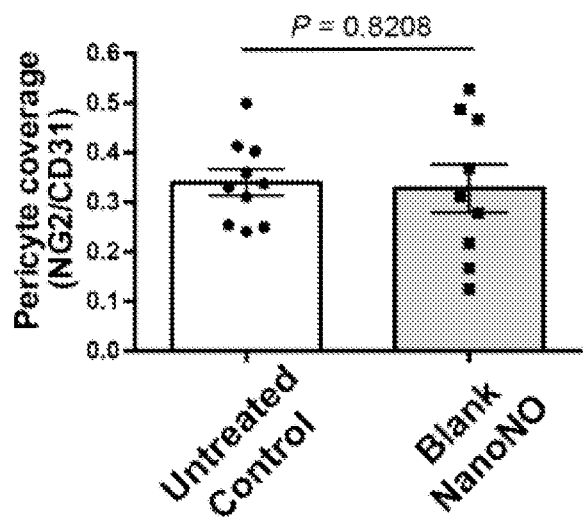
Figure 4I:
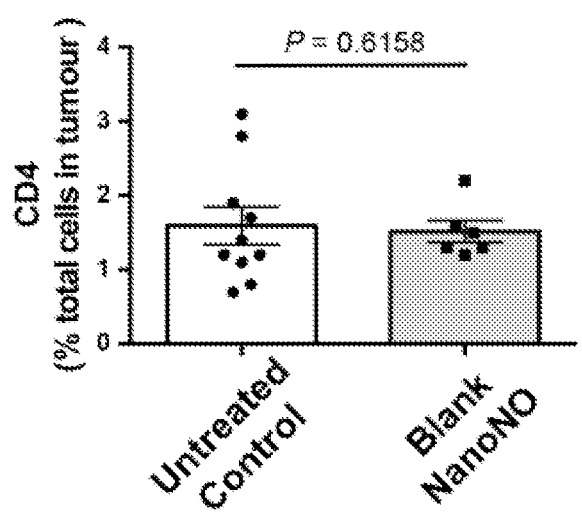
Figure 4I:
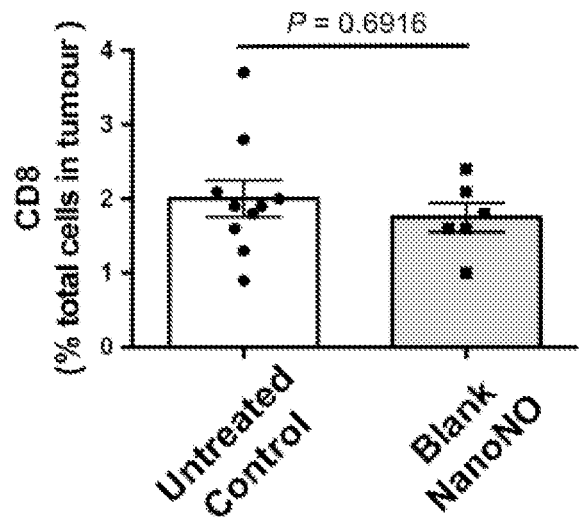
Figure 4I:
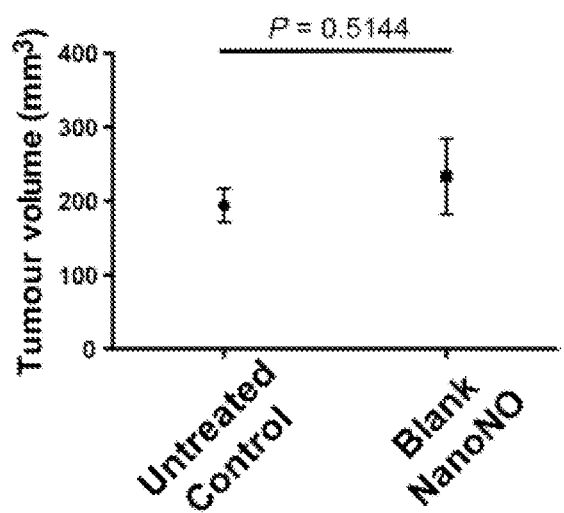

The inventors then evaluated whether the enhanced NO accumulation achieved by NanoNO resulted in tumor growth inhibition in orthotopic murine (HCA-1) and human (JHH-7) HCC models. FIG. 4H is a schematic illustration of the treatment protocol for NanoNO. In FIG. 4H, ten days after the implantation of HCC cells, mice were treated with various doses of NanoNO on days 10, 12, 14, 17, 19 and 21, and tumor size was measured on day 24 (control, n=15 mice; 1 mg/kg NanoNO, n=15 mice; 0.05 and 0.1 mg/kg NanoNO, n=10 mice; 0.25 mg/kg NanoNO, n=4 mice; 0.5 mg/kg NanoNO, n=7 mice). All data are shown as the mean value± the s.e.m. FIGS. 4Ia-4If show effect of blank-NanoNO on the tumor microenvironment and tumor growth. FIGS. 4Ia-4Ic show systemic injections of blank-NanoNO (NanoNO without encapsulation of DNIC) did not change the MVD. FIG. 4Ia, tumor hypoxia; FIG. 4Ib, the proportion of functional vessels that were double-stained with anti-NG2/anti-CD31; FIG. 4Ic, pericyte coverage double-stained with anti-NG2/anti-CD31 in orthotopic HCA-1 tumors compared with untreated controls (Untreated control, n=10; blank-NanoNO; n=9); FIGS. 4Id-4Ie, infiltration of CD4 (4Id) and CD8 (4Ie) T cells in HCA-1 tumor tissues remained unchanged after treatment with blank-NanoNO (Untreated control, n=10 mice; blank-NanoNO; n=6 mice); FIG. 4If, tumor sizes in the orthotopic HCA-1 HCC models treated with blank-NanoNO (Untreated control, n=15 mice; blank-NanoNO; n=4 mice). All values are expressed as mean±s.e.m. Analysis was performed using two-tailed Mann-Whitney U test.

As shown in FIGS. 4H and 4Ia-4If, high doses of NanoNO treatment (DNIC: 0.5-1 mg/kg) significantly suppressed HCC growth in both the HCA-1 and JHH-7 models, wherein FIGS. 4Ia to 4If show that the NanoNO carrier alone would not have the therapeutic effect. The effects are all due to the NanoNO carrier loaded with DNIC.

Figure 4J:
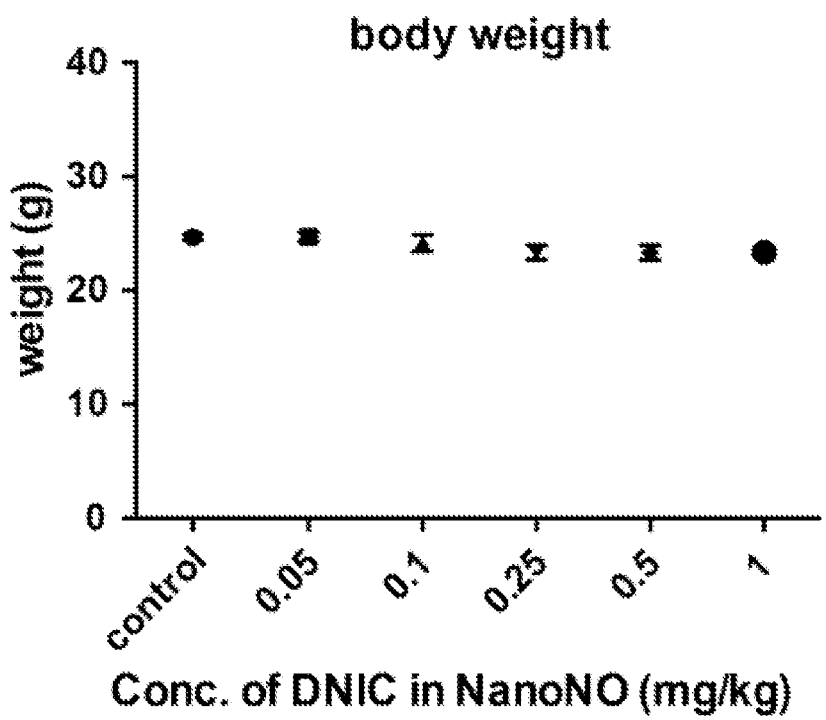
FIG. 4J is another data diagram of the effect of NanoNO on anticancer, in which ● represents control; ■ represents the concentration of DNIC in NanoNO is 0.05 mg/kg; ▲ represents the concentration of DNIC in NanoNO is 0.1 mg/kg; ▼ represents the concentration of DNIC in NanoNO is 0.25 mg/kg; ◆ represents the concentration of DNIC in NanoNO is 0.5 mg/kg; ● represents the concentration of DNIC in NanoNO is 1 mg/kg.

FIG. 4J shows in vivo administration of NanoNO did not show systemic toxicity. There was no significant change in the body weight of the mice in all NanoNO-treated groups. The body weight was measured 24 days post-implantation in the presence or absence of treatment with NanoNO with different doses (control, n=14 mice; 0.05, 0.1, 0.5 and 1 mg/kg NanoNO, n=7 mice; 0.25 mg/kg NanoNO, n=5 mice). Data are shown as the mean value± the s.e.m.

Table 6 shows toxicity profile of NanoNO. Measurement of hepatic enzyme levels in the serum of mice left untreated (control) or treated with 1 mg/kg NanoNO in healthy C3H mice. Serum samples were taken 24 hours after treatment (n=6 mice). Data are shown as the mean value± the SD. Abbreviations: ALT, alanine aminotransferase; AST, aspartate aminotransferase; ALP, alkaline phosphatase; γ-GT, gamma glutamyl transpeptidase.

TABLE 6

|  | Control | NanoNO |
| --- | --- | --- |
| AST (U/L) | 72.1 ± 5.4 | 69.7 ± 9.9 |
| ALT (U/L) | 28.7 ± 1.4 | 28.8 ± 1.9 |
| ALP (U/L) | 530.7 ± 15.4 | 451.5 ± 25.1 |
| γ-GT | 0.33 ± 0.07 | 0.60 ± 0.10 |

TABLE 7

|  | 1 ft after treatment | | 24 h after treatment | |
| --- | --- | --- | --- | --- |
| Treatment | Systolic (mmHg) | Diastolic (mmHg) | Systolic (mmHg) | Diastolic (mmHg) |
| Control | 104.6 ± 8.0 | 57.1 ± 7.2 | 110.7 ± 3.1 | 64.2 ± 8.7 |
| Free DNIC | 102.4 ± 17.4 | 62.9 ± 24.5 | 99.5 ± 11.8 | 55.7 ± 13.3 |
| NanoNO | 104.3 ± 6.2 | 60.2 ± 2.9 | 106.9 ± 11.34 | 54.9 ± 5.3 |

Table 7 shows blood pressure recording at 1 hour and 24 hours after treatment with the PBS control, free DNIC and low-dose NanoNO (0.1 mg/kg) in healthy C3H mice. The systolic pressure and diastolic pressure in healthy C3H mice were measured by Visitech Systems after different treatments (n=4 mice). All data are shown as the mean value± the SD.

The results of this example indicated that NanoNO displayed anti-cancer effects in a dose-dependent manner. NanoNO was well-tolerated in animal safety studies, with no weight loss, no change in blood pressure and hepatic enzyme levels comparable to those of untreated mice (FIG. 14J and Table 7).

Example 5

Evaluation of Effect of Tumor Vessel Normalization by NanoNO

The tumor necrosis factor-related apoptosis-inducing ligand (TRAIL) treatment process used in the following experiments was as follows. A $His_6$-tagged human TRAIL (aa95-281) expression plasmid (pQE-hTR) was purchased from Addgene (Plasmid #21811; Cambridge, Mass., USA). For expression of $His_6$-TRAIL, this plasmid was transformed into BL21 (DE3) bacteria and purified by affinity chromatography on Ni-NTA agarose beads.

Mice with orthotopic HCC were injected with TRAIL (2.5, 5 or 20 mg/kg/dose, ten doses, five doses per week) in combination with low-dose NanoNO (0.1 mg/kg). Two weeks after the first treatment, mice were sacrificed for further analysis.

The procedure of doxorubicin (DOX) perfusion and treatment was as follows. Ten days after the implantation of HCC cells, mice were treated with NanoNO (0.1 mg/kg/dose, six doses, three doses per week) intravenously. After 2 weeks of treatment, mice were injected with DOX (8 mg/kg) intravenously. One hour after injection, tumor tissues were embedded in Tissue-Tek (OCT compound) and frozen in liquid nitrogen. Tumor tissue was sectioned (10 μm thick) onto slides and counterstained with DAPI (Vector Laboratories, Burlingame, Calif.). DOX perfusion was imaged by using a confocal laser scanning microscope (LSM780, Zeiss, Germany). Images are representative sections from three mice per group.

To evaluate the therapeutic effect of combination therapy, DOX (1 or 4 mg/kg) with or without low-dose NanoNO (0.1 mg/kg) was intravenously administered to mice with orthotopic HCC beginning 10 days after the implantation. The tumor volume was evaluated after 2 weeks of treatment.

The procedure of assessment of apoptosis by TUNEL staining was as follows. Frozen tumor sections were stained by using a TACS™ TdT Kit (R&D Systems, Minneapolis, Minn.) according to the manufacturer's recommendations. The apoptotic cells were counted in randomly selected visual fields.

The procedure of intravital microscopy was as follows. Following intravenous injection of BSA-FITC (40 mg/kg), multiphoton imaging was carried out on Zeiss LSM 780 microscope with a 10× Achroplan IR lens (NA=0.4). Two-photon excitation with a Ti-sapphire laser locked at 920 nm and emitted photons within 500-600 nm were collected with a high-sensitivity 38-channel Quasar detector in LSM 780. Imaging frames of 1024×1024 pixels in LSM 780 were acquired at a speed of 1 frame per second every 5 min for a total of 30 min. Images are representative sections from three mice per group.

The procedure of immunostaining was as follows. Tumor tissues were embedded in Tissue-Tek (OCT compound) and kept frozen at −80° C. Then, tissues were sectioned (10 μm thick) and fixed in acetone at −20° C. for 10 minutes and washed with PBS. Then, the sections were blocked with 5% bovine serum albumin solution for an hour at room temperature and incubated with primary antibodies against CD31 (ab28364, Abcam, Mass., USA), granzymeB (ab4059, Abcam, Mass., USA) or PD-L1 (Clone 10F9G2, Biolegend, Calif., USA), NG2 (clone 132.38, Millipore, Calif., USA) at 4° C. overnight. Sections were washed with PBS and incubated with Alexa Fluor® 488 or Alexa Fluor© 647 anti-rabbit IgG secondary antibodies (Life Technologies, Grand Island, N.Y.) for an hour at room temperature. The sections were washed by PBS and counterstained with DAPI (Vector Laboratories, Burlingame, Calif.). All the sections were imaged by using a confocal laser scanning microscope (LSM780, Zeiss, Germany).

For analysis of tumor hypoxia, pimonidazole (Hypoxyprobe, Hypoxyprobe Inc., 60 mg/kg) was injected i.v. an hour before the animals were sacrificed. Hypoxia was assessed in frozen tissues sections by immunostaining of pimonidazole using an anti-Hypoxyprobe-FITC-labelled antibody. All sections were imaged by using a confocal laser scanning microscope (LSM780, Zeiss, Germany). Images are representative sections from four mice per group.

For analysis of functional blood vessels, FITC-labeled *Lycopersicon esculentum* lectin (100 μL in PBS, Vector Laboratories, Burlingame, Calif.) was injected i.v. 5 minutes before the animals were sacrificed. Tumor tissues were embedded in Tissue-Tek (OCT compound) and frozen in liquid nitrogen immediately.

The procedure of distribution of NO in the tumor area was as follows. C3H/HeNCrNarl male mice with orthotopic implants of HCA-1 cells were injected with free DNIC and NanoNO (10 mg/kg) intravenously. Four hours after administration, mice were sacrificed. Tumor tissues were embedded in Tissue-Tek (OCT compound) and immediately frozen in liquid nitrogen. Tumor tissue was sectioned (10 μm thick) onto slides. The slide was washed with PBS and incubated with 100 μM DAR-1 (Sigma, USA) at 37° C. for an hour. The sections were washed with PBS and counterstained with DAPI (Vector Laboratories, Burlingame, Calif.). All the sections were imaged by using a confocal laser scanning microscope (LSM780, Zeiss, Germany). Images are representative sections from four mice per group.

NO acts as a crucial modulator in regulating angiogenesis and maintaining the vasculature function in TME. To test the direct effect of NO on angiogenesis and vessel maturation, the inventors explored the expression profile of seven angiogenesis-related genes in HUVECs after treatment with DNIC in the free form. The inventors found that 3 pro-angiogenic genes (VEGF, ANGPT2, and EGF) were down-regulated in HUVECs, whereas 2 vessel maturation-related genes (S1PR1 and ANGPT1) were significantly upregulated after treatment with the NO donor DNIC (FIG. 5A).

Figure 5A:
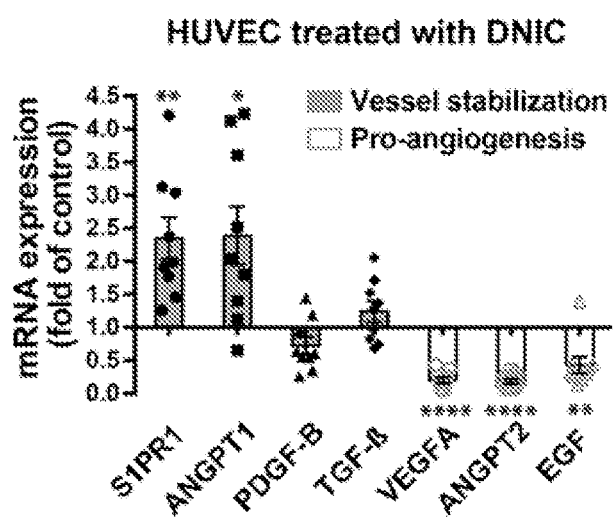
FIG. 5A is a data diagram of normalized tumor blood vessels in HCC by low-dose NanoNO.

FIG. 5A is a data diagram of normalized tumor blood vessels in HCC by low-dose NanoNO. Expression of the pro-angiogenic and vessel stabilizing factors in HUVECs 24 h after treatment with DNIC (1 μM) measured by RT-qPCR. The results are expressed as the fold change relative to the untreated control group (n=9 biologically independent samples). Data are pooled from three independent experiments. *P=0.0314, P=0.0012 and **P=0.0001. These results suggest that exposure to the DNIC may directly reprogram the gene expression profile of endothelial cells, shifting from a pro-angiogenic phenotype to a vascular-stabilizing signature in tumors.

In addition to the direct effect of NO on angiogenesis and vessel stabilization, perivascular NO gradients are known to normalize the distorted tumor blood vessel architecture and function. Therefore, the inventors evaluated the effects of NanoNO on the mean vessel density (MVD) and vessel normalization in both orthotopic murine (HCA-1) and human (JHH-7) HCC models.

Figure 5B:
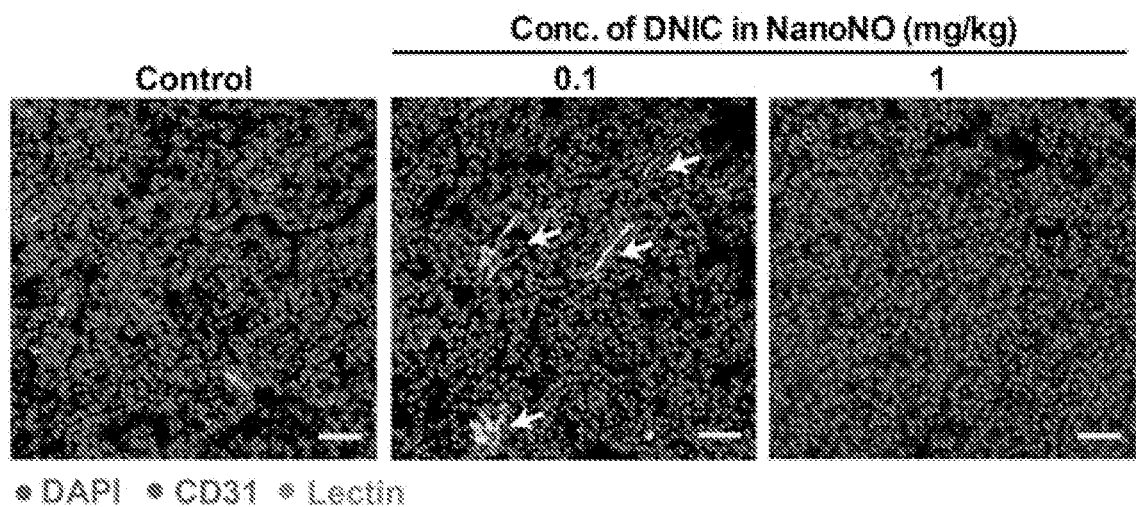
FIG. 5B is a staining diagram of the effect of NanoNO on the normalization of tumor blood vessels.

FIG. 5B shows tumor vessel perfusion in HCC tumors after treatment with high-dose (1 mg/kg) or low-dose (0.1 mg/kg) NanoNO. Ten days after the implantation of HCA-1 HCC cells, mice were treated with NanoNO (0.1 or 1 mg/kg) on days 10, 12, 14, 17, 19 and 21, and tumors were analysed on day 24. CD31-positive endothelial cells, red; FITC-lectin-perfused vessels, green. Scale bar, 50 μm. The experiments were repeated twice independently.

Figure 5C:
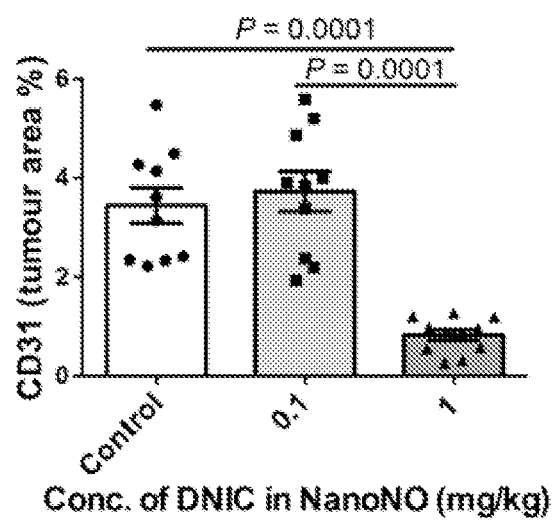
FIG. 5C is a data diagram of the effect of NanoNO on the normalization of tumor blood vessels.

FIG. 5C shows quantification of mean vessel density (MVD) in HCC tumors 24 days after implantation in mice treated or untreated with NanoNO. MVD was determined by CD31 staining and is represented as percentage of the total tumor area (n=10 section images from four mice).

Figure 5D:
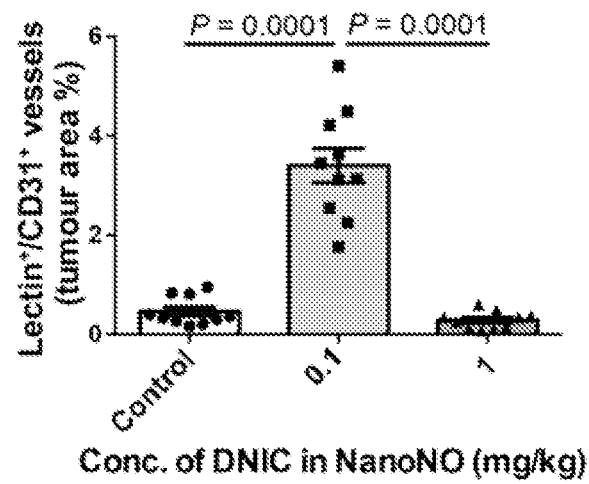
FIG. 5D is another data diagram of the effect of NanoNO on the normalization of tumor blood vessels.

FIG. 5D shows quantification of perfused functional tumor vessels in HCC tumors from NanoNO-treated or untreated mice determined by CD31$^+$lectin$^+$ staining and represented as a percentage of the total tumor area (n=10 section images from four mice).

Figure 5E:
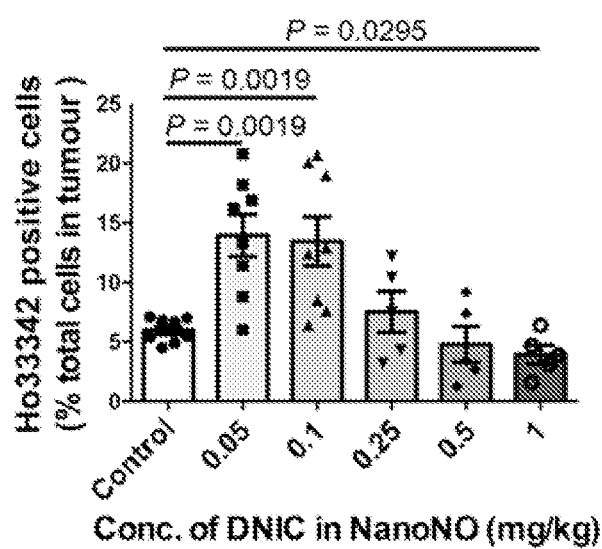
FIG. 5E is another data diagram of the effect of NanoNO on the normalization of tumor blood vessels.

FIG. 5E shows the percentage of Hoechst 33342-positive cells in HCC after treatment with NanoNO at different doses. Mice were injected intravenously with 200 μg Hoechst 33342 before tumor harvest on day 24 (control, 0.05 and 0.1 mg/kg NanoNO, n=8 mice; 0.25, 0.5 and 1 mg/kg NanoNO, n=5 mice).

Treatment with high doses of NanoNO (DNIC: 1 mg/kg) significantly decreased the MVD in HCC tumors and, thus, reduced tumor perfusion, indicating that the sufficient delivery of NO exerts anti-angiogenic activity (FIGS. 5B-5E and 4Ia-4If). Although the low-dose NanoNO treatment (DNIC: 0.1 mg/kg) did not change the MVD in tumors, it significantly increased tumor perfusion (Hoechst 33342$^+$ area) and functional perfused vessels (Lectin$^+$CD31$^+$ area), which were distributed more evenly in tumors compared with the high-dose NanoNO treatment and control groups (FIGS. 5D and 5E).

Figure 5F:
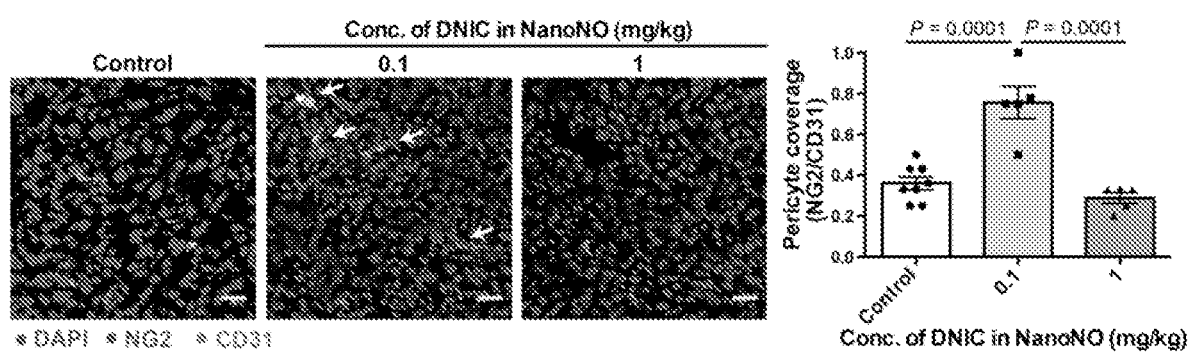
FIG. 5F is a staining diagram of the effect of NanoNO on the normalization of tumor blood vessels.

FIG. 5F shows quantification of pericyte coverage (fraction of area covered) in HCC after treatment, with a high-dose (1 mg/kg) or low-dose (0.1 mg/kg) of NanoNO. CD31-positive endothelial cells are stained green, and NG2-positive pericytes are stained red (control, n=8 section images from four mice; NanoNO treatment, n=5 section images from three mice). Scale bar, 20 μm.

Figure 5G:
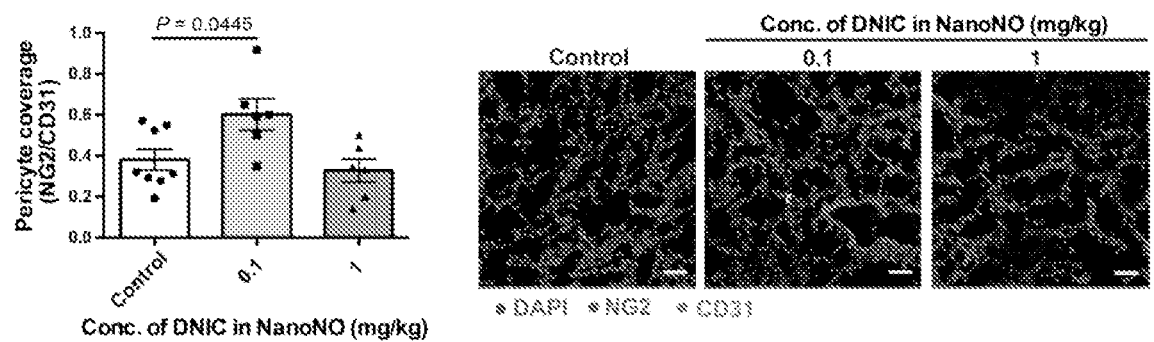
FIG. 5Ga-5Gc show that low-dose NanoNO can normalize tumor blood vessels in the human HCC (JHH-7) model.
Figure 5G:
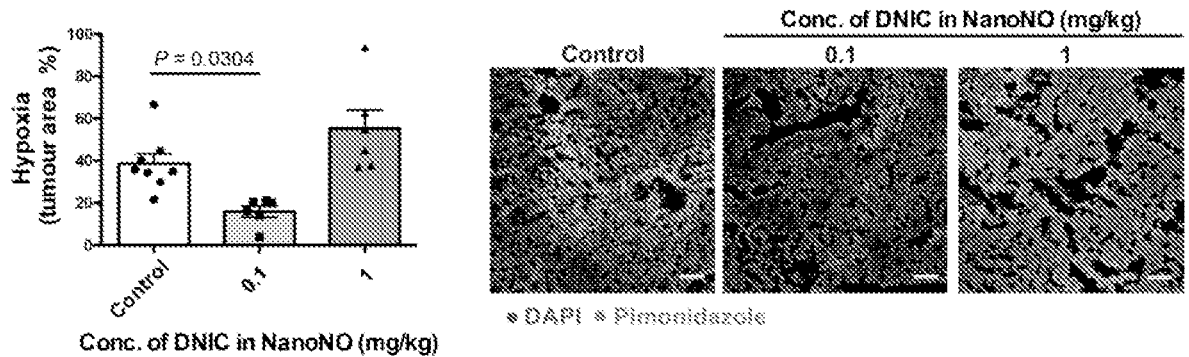
Figure 5G:
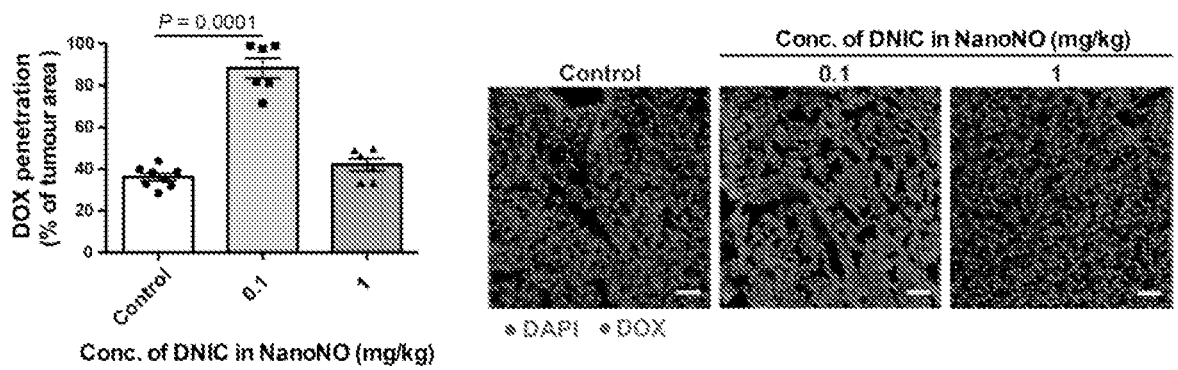

FIGS. 5Ga-5Gc show low-dose NanoNO normalizes the tumor vasculature in the human HCC (JHH-7) model. FIG. 5Ga shows quantification of pericyte coverage (fraction of area covered) in JHH-7 tumors after treatment, with a high dose (1 mg/kg) or low dose (0.1 mg/kg) of NanoNO. CD31-positive endothelial cells, green; NG2-positive pericytes, red. FIG. 5Gb shows the proportion of pimonidazole-positive areas as a marker for hypoxia in HCC after treatment with a high dose (1 mg/kg) or low dose (0.1 mg/kg) of NanoNO. FIG. 5Gc shows perfusion of DOX in tumors monitored by confocal microscopy one hour after injection of DOX (control, n=8 section images from four mice; NanoNO, n=6 section images from three mice). Scale bar, 50 μm. All data are shown as the mean value± the s.e.m. Analysis was performed using an ordinary one-way ANOVA with Tukey's multiple comparison test.

Figure 5H:
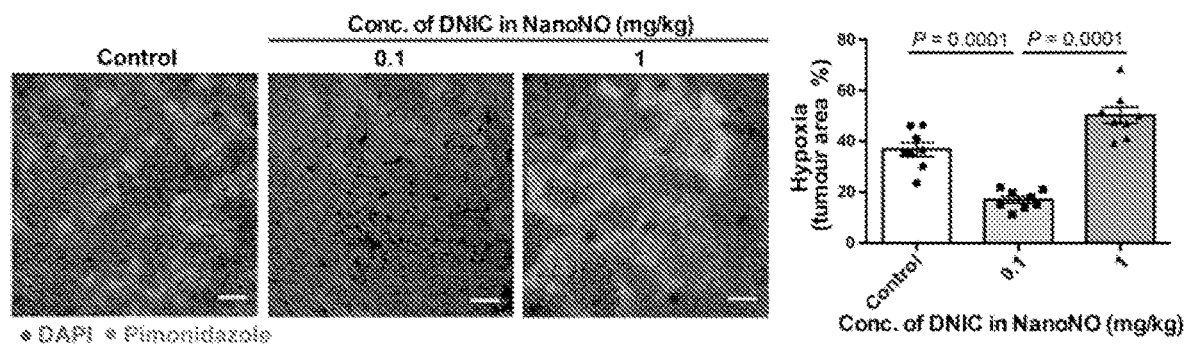
FIG. 5H is a staining diagram of the effect of NanoNO on the normalization of tumor blood vessels.

FIG. 5H shows the proportion of pimonidazole-positive areas as a marker for hypoxia in HCC after treatment with a high-dose (1 mg/kg) or low-dose (0.1 mg/kg) of NanoNO (n=8 section images from four mice). Scale bar, 100 μm. Data are pooled from two independent experiments. All data are shown as the mean value± the s.e.m.

In addition, costaining with the vessel marker CD31 and pericyte marker NG2 also revealed that low-dose NanoNO enhanced the pericyte coverage of tumor vessels compared with high-dose NanoNO treatment and control (FIGS. 5F, 4Ia-4If and 5Ga-5Gc), indicating that the tumor vasculature is more mature after treatment with low-dose NanoNO. Consequently, low-dose NanoNO treatment significantly reduced the hypoxic tumor area, as measured by pimonidazole, compared with the high-dose NanoNO treatment and control (FIGS. 5H, 4Ia-4If and 5Ga-5Gc). In summary, although treatment with NanoNO at low doses did not have anti-angiogenic and anti-cancer properties, in contrast to high-dose NanoNO treatment, it normalized tumor blood vessels and improved blood vessel function and perfusion in HCC tumors.

Figure 5I:
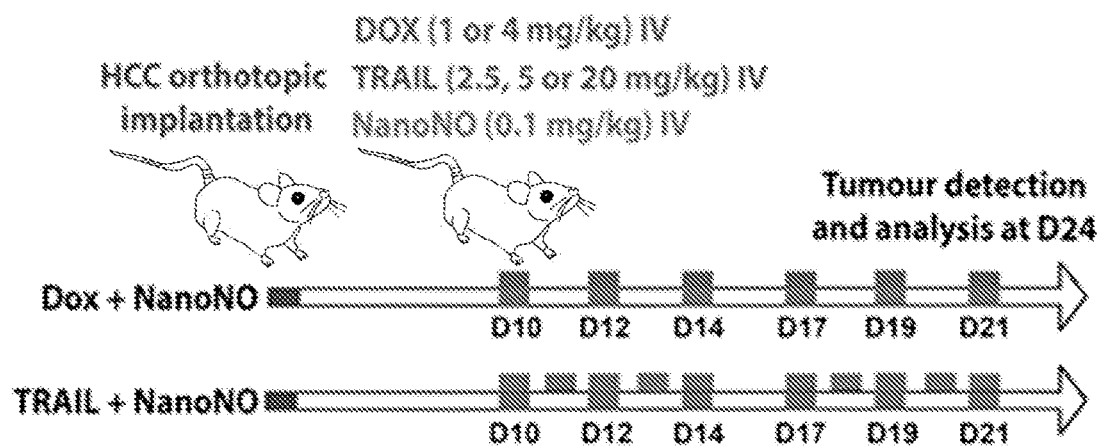
FIG. 5I is a treatment schedule for low-dose NanoNO to enhance drug delivery efficiency and enhance anti-cancer effect.

FIG. 5I is a treatment protocol showing low-dose NanoNO improves drug delivery efficiency and enhances anti-cancer efficacy. The procedure was as follows. Ten days after the implantation of HCC cells, mice were intravenously treated with doxorubicin (DOX) (4 mg/kg for the HCA-1 HCC model and 1 mg/kg for the JHH-7 HCC model) six times (at 2- to 3-day intervals) or recombinant tumor necrosis factor-related apoptosis-inducing ligand (TRAIL) ten times (at 1- to 2-day intervals). For the combination groups, mice treated with DOX or recombinant TRAIL protein, as shown above, received intravenous low-dose NanoNO on days 10, 12, 14, 17, 19 and 21. Tumors were analysed on day 24 of postimplantation.

Figure 5J:
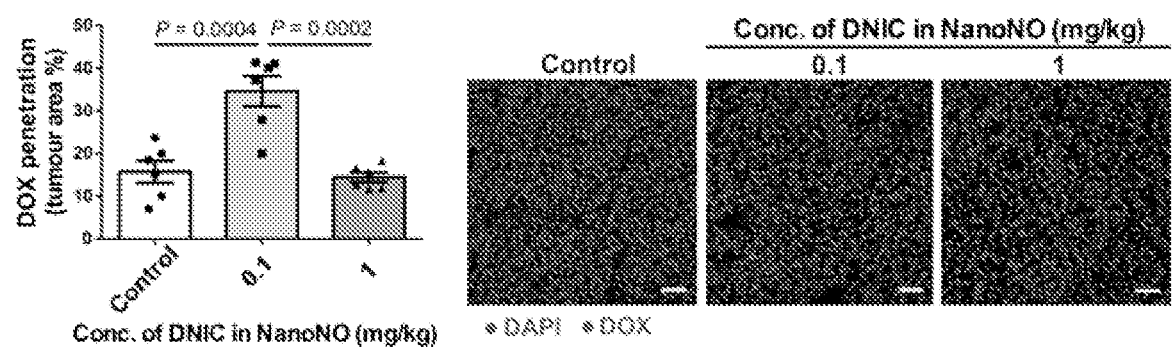
FIG. 5J is a data diagram of low-dose NanoNO on enhancing drug delivery efficiency and enhancing anti-cancer effect.

FIG. 5J is a data diagram of low-dose NanoNO on enhancing drug delivery efficiency and enhancing anti-cancer effect. Perfusion of DOX in tumors monitored by confocal microscopy (n=6 section images from three mice). Representative images of DOX perfusion in tumors one hour after injection of DOX are shown from two independent experiments. Scale bar, 50 μm.

Figure 5K:
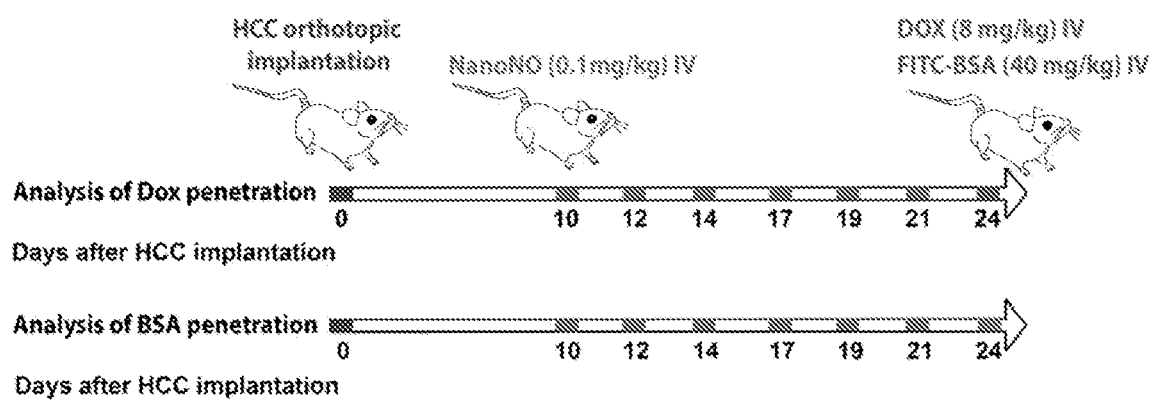
FIG. 5K is a treatment schedule for analysis of DOX and BSA tumor penetration.

FIG. 5K is a treatment schedule for analysis of DOX and BSA tumor penetration. C3H/HeNCrNarl male mice with orthotopic implants of HCA-1 cells were intravenously injected with NanoNO (0.1 mg/kg/dose, six doses, three doses per week). After treatment, mice were intravenously injected with DOX (8 mg/kg). One hour after injection, tumor tissues were collected and embedded. DOX perfusion was imaged and quantified with a Zeiss LSM 780 confocal microscope. For evaluation of BSA penetration, following intravenous injection of BSA-FITC (40 mg/kg), multiphoton imaging was carried out on a Zeiss LSM 780 microscope.

Figure 5L:
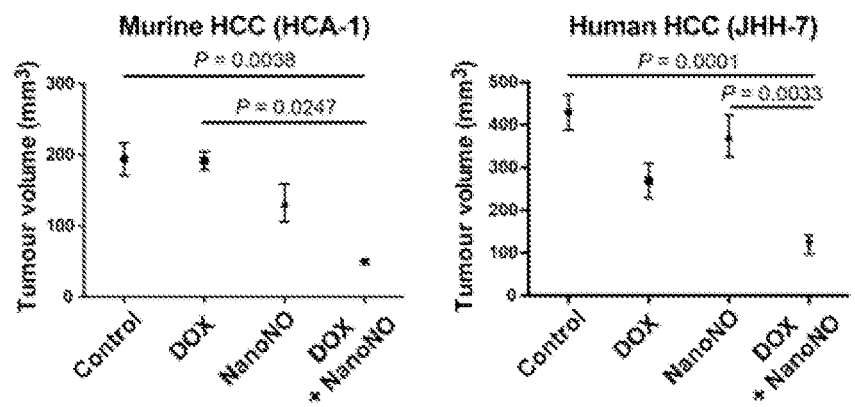
FIG. 5L shows volumes of orthotopic HCC tumors 24 days postimplantation in treated and untreated (control) mice.

FIG. 5L shows volumes of orthotopic HCC tumors 24 days postimplantation in treated and untreated (control) mice, as described in FIG. 5I (control, n=15 mice; NanoNO alone, n=10 mice; DOX alone and combination group, n=5 mice).

The abnormal tumor vessels in the TME negatively affect drug delivery and penetration and, hence, cancer therapy efficacy. Therefore, the inventors assessed the manner in which vascular normalization triggered by low-dose NanoNO treatment affects drug delivery. The inventors studied the tumor penetration and anti-cancer efficacy of a small molecule chemotherapeutic (Doxorubicin, DOX) and a macromolecular protein-based therapeutic agent (tumor necrosis, factor-related, apoptosis-inducing ligand; TRAIL) in the orthotopic HCC models in the presence or absence of high-dose or low-dose NanoNO (FIG. 5I). Low-dose NanoNO treatment led to a 2.5-fold increase in DOX penetration into orthotopic HCC tumors, whereas no improvement was observed with high-dose NanoNO treatment (FIGS. 5J, 5Ga-5Gc and 5K), which is consistent with the differential dose effect of NanoNO on vascular normalization. The enhanced DOX penetration observed with low-dose NanoNO treatment resulted in a significant reduction in tumor growth compared to treatment with DOX alone (FIG. 5L).

Figure 5M:
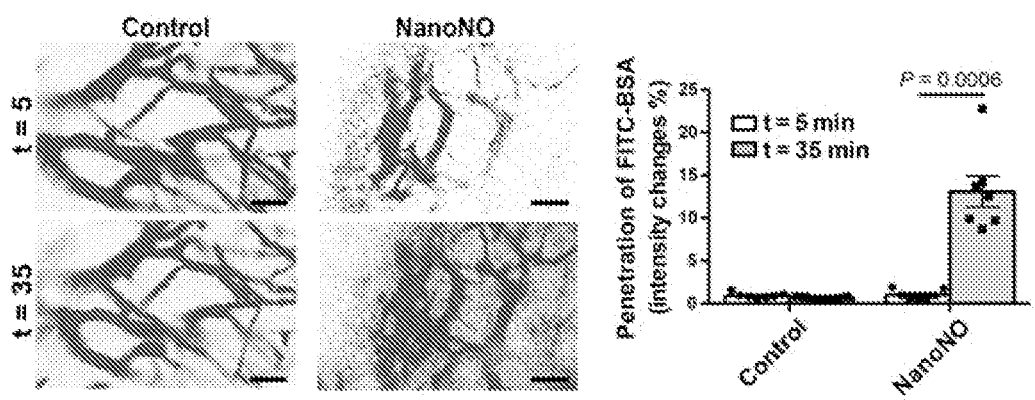
FIG. 5M shows penetration of FITC-BSA in tumors in response to vessel normalizing therapy, with a low-dose of NanoNO (0.1 mg/kg).

FIG. 5M shows penetration of FITC-BSA in tumors in response to vessel normalizing therapy, with a low-dose of NanoNO (0.1 mg/kg), monitored by multiphoton imaging (n=7) for t=5 (5 minutes) and t=35 (35 minutes) after FITC-BSA injection. Scale bar, 100 μm. Experiments were repeated three times with similar results.

Figure 5N:
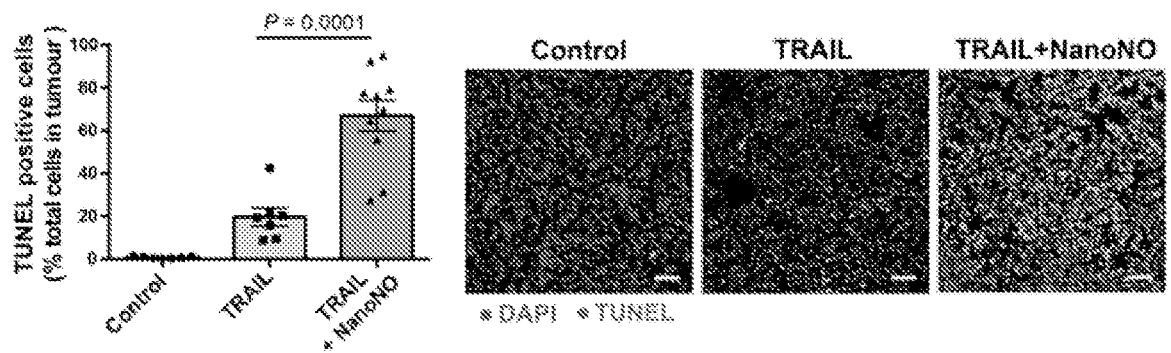
FIG. 5N shows TRAIL therapy in combination with low-dose NanoNO significantly increased the induction of apoptosis in tumors.

FIG. 5N shows TRAIL therapy in combination with low-dose NanoNO significantly increased the induction of apoptosis in tumors (control and TRAIL alone, n=7 section images from three mice; combination group, n=10 section images from four mice). Data are pooled from two independent experiments. Representative immunofluorescence images of TUNEL staining at 24 days postimplantation of orthotopic HCA-1 tumors after TRAIL treatment. Scale bar, 50 μm.

Figure 5O:
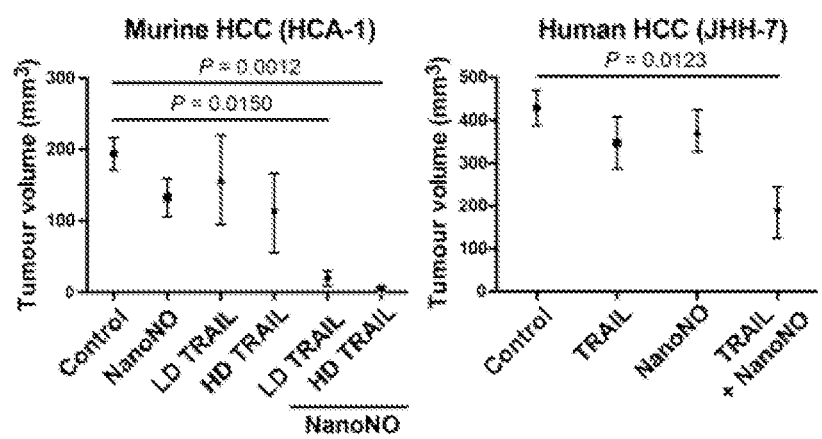
FIG. 5O shows volumes of orthotopic HCC tumors when combined with low-dose NanoNO (0.1 mg/kg) and recombinant TRAIL protein (LD: 5 mg/kg or HD: 20 mg/kg for HCA-1 HCC model).

FIG. 5O shows volumes of orthotopic HCC tumors in response to treatment with low-dose NanoNO (0.1 mg/kg) in combination with recombinant TRAIL protein (LD: 5 mg/kg or HD: 20 mg/kg for HCA-1 HCC model; 2.5 mg/kg for JHH-7 HCC model; control, n=15 mice; NanoNO alone, n=10 mice; TRAIL alone, n=5 mice; combination of TRAIL LD and NanoNO n=4 mice; combination of TRAIL HD and NanoNO, n=6 mice).

The inventors used intravital multiphoton microscopy and fluorescein isothiocyanate labelled bovine serum albumin (FITC-labeled BSA) as a probe to model protein-based macromolecular drugs (FIG. 5K). Treatment with low-dose NanoNO led to a 12-fold increase in the penetration of FITC-BSA into HCC through functional vessels compared with the control group 35 minutes after FITC-BSA injection (FIG. 5M). Penetration of the protein-based therapeutic TRAIL, which efficiently triggers cell death in cancer cells, was assessed in the presence or absence of low-dose NanoNO in mice bearing HCC. The inventors found that the TRAIL treatment, in combination with low-dose NanoNO, significantly increased the number of apoptotic cells in orthotopic HCA-1 tumors compared to the treatment with only TRAIL (FIG. 5N). The increased tumor apoptosis observed with the combined treatment led to significant tumor growth inhibition in both orthotopic murine (HCA-1) and human (JHH-7) HCC models (FIG. 5O).

Figure 5P:
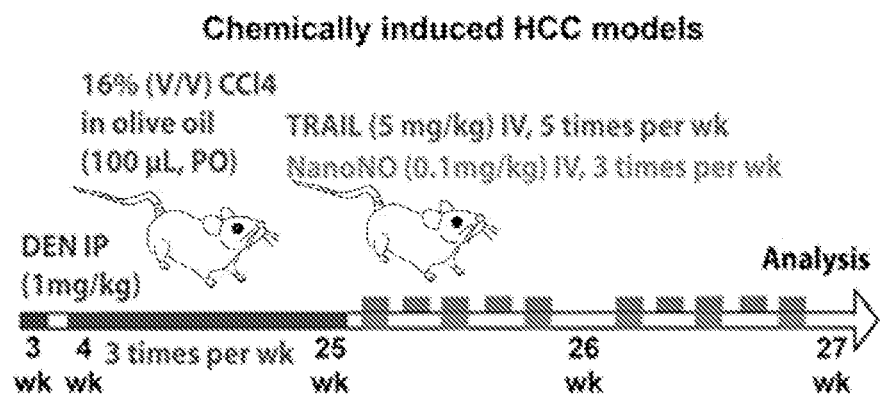
FIG. 5P shows a treatment protocol for the $CCl_4$-induced HCC model.

The inventors further evaluated the effect of NanoNO in mice with N-nitrosodiethylamine (DEN) and $CCl_4$-induced liver fibrosis and inflammation-associated HCC (FIG. 5P). The procedure of DEN and $CCl_4$-induced murine HCC model was as follows. For chemical induction of HCC, C3H/HeNCrNarl male mice (3-4 weeks) were treated with N-nitrosodiethylamine (DEN) (i.p. injection of 1 mg/kg). Then, the mice were treated with 16% (V/V) carbon tetrachloride ($CCl_4$) in olive oil (0.1 mL/mouse) 3 times per week for 21 continuous weeks. For evaluation of the effect of NanoNO, NanoNO (DNIC: 0.1 mg/kg, three doses per week) or TRAIL (5 mg/kg, five doses per week) was intravenously administered to mice following $CCl_4$ treatment. The tumor nodules in the livers were collected and analysed after 2 weeks of treatment.

Figure 5Q:
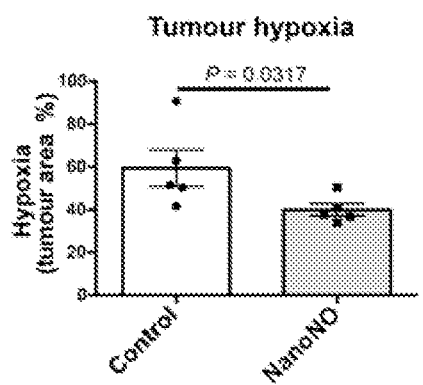
FIG. 5Q shows that the tumor hypoxic area indicated by pimonidazole-positive staining in $CCl_4$-induced HCC after treatment with low-dose NanoNO.
Figure 5R:
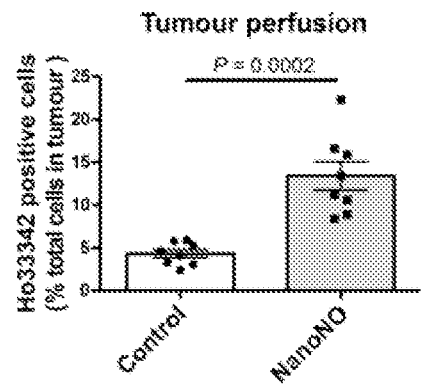
FIG. 5R shows the percentage of Hoechst 33342-positive cells in HCC after treatment with low-dose NanoNO.
Figure 5S:
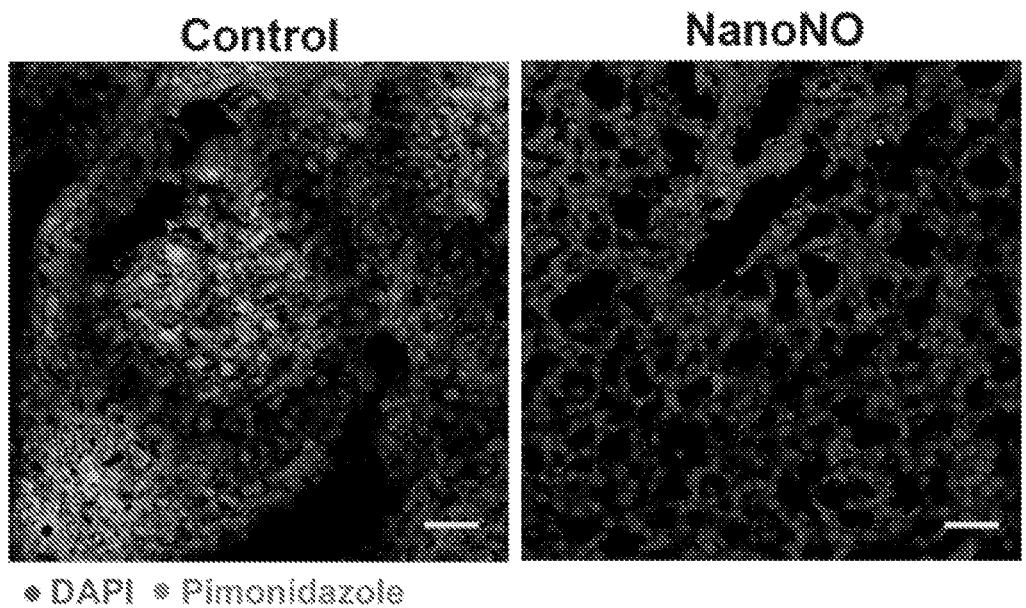
FIG. 5S shows low-dose NanoNO reduces tumor hypoxia in a $CCl_4$-induced spontaneous HCC model.
Figure 5T:
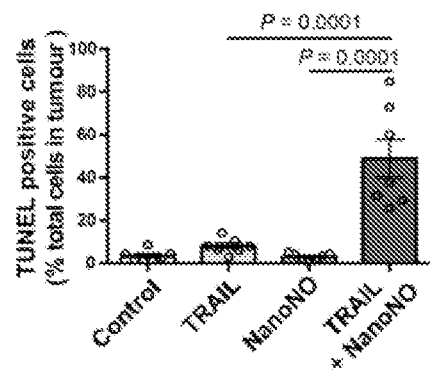
FIG. 5T shows TRAIL therapy in combination with low-dose NanoNO increased the induction of apoptosis in $CCl_4$-induced HCC tumors.

FIG. 5P shows a treatment protocol for the $CCl_4$-induced HCC model. FIG. 5Q shows that the tumor hypoxic area indicated by pimonidazole-positive staining in $CCl_4$-induced HCC after treatment with low-dose NanoNO (n=5 mice). FIG. 5R shows the percentage of Hoechst 33342-positive cells in HCC after treatment with low-dose NanoNO, as measured by flow cytometry (n=8 mice). FIG. 5S shows low-dose NanoNO reduces tumor hypoxia in a $CCl_4$-induced spontaneous HCC model. The proportion of pimonidazole-positive areas as a marker for hypoxia in HCC after treatment with low-dose (0.1 mg/kg) NanoNO monitored by confocal microscopy. The experiment was performed once. Scale bar, 50 μm. FIG. 5T shows TRAIL therapy in combination with low-dose NanoNO increased the induction of apoptosis in $CCl_4$-induced HCC tumors (n=7 section images from three mice). All data are shown as the mean value± the s.e.m.

The chemically induced HCC model mimics the injury-fibrosis-HCC sequence found in humans. Consistently, treatment of low-dose NanoNO decreased tumor hypoxia and increased tumor perfusion (Hoechst 33342$^+$ area) in $CCl_4$-induced HCC (FIGS. 5Q, 5R and 5S). The combination treatment with TRAIL therapy and low-dose NanoNO synergistically induced apoptosis in $CCl_4$-induced HCC (FIG. 5T). Taken together, the inventors demonstrated that the combination treatment with TRAIL therapy and low-dose NanoNO synergistically achieved anti-cancer efficacy through vascular normalization and increased penetration of therapeutic proteins.

Example 6

Reprogramming of Tumor Microenvironment by NanoNO

The structurally and functionally aberrant tumor vasculature leads to a highly heterogeneous and hypoxic TME that can polarize tumor-associated macrophages (TAMs) into an immune-suppressive M2-like phenotype and impede tumor infiltration of T cells, resulting in suppression of the anti-tumor immune response. Because low-dose NanoNO treatment leads to vascular normalization, the inventors examined whether it also altered the TAM M1/M2 polarization status and T cell infiltration in HCC.

The procedure of flow cytometry analysis and cell sorting was as follows. C3H/HeNCrNarl male mice with orthotopic implants of HCA-1 cells were perfused through intracardiac injection of PBS and sacrificed. Tumor tissues were digested at 37° C. for 1 h with collagenase type 1A (1.5 mg/mL) and hyaluronidase (1.5 mg/mL) in DMEM medium. The cell suspensions were stained for antibodies. The following antibodies were used for the flow cytometry analysis: CD45-FITC (30-F11), CD3e-APC (145-2C11), CD8-PE-Cy7(53-6.7), CD4-PE (RM4-5), CD16/CD32 BD Fc Block (2.4G2), 7-AAD from BD Biosciences, Calif., USA; Granzyme B-FITC (GB11), CD86-APC-Cy7 (GL-1), CD206-APC (C068C2) from Biolegend, Calif., USA; F4/80-PE (BM8) from eBioscience, Calif., USA. Flow cytometry data were obtained from a BD FACSAria III flow cytometer (Becton Dickinson, Calif., USA) and analysed with FACSDiva™ software.

To detect Granzyme B in CD8 T cells, the cell suspensions were fixed with 4% paraformaldehyde solution, permeabilized in Cytofix/Cytoperm solution (BD Biosciences, Calif., USA) and stained with an intracellular Granzyme B-FITC antibody (BioLegend, Calif., USA) according to the manufacturer's instructions.

The tumor-associated macrophages were isolated through immunomagnetic separation using MS columns and anti-mouse CD11b-conjugated magnetic beads according to the manufacturer's instructions (Miltenyi Biotec, Germany), after which they were stained for CD45-FITC (30-F11) (BD Biosciences, Calif., USA), F4/80-PE (BM8) (eBioscience, Calif., USA) and 7-AAD. The 7-AAD$^-$/CD45$^+$/F4/80$^+$ cells were sorted by a BD FACSAria III flow cytometer (Becton Dickinson, Calif., USA).

Figure 6A:
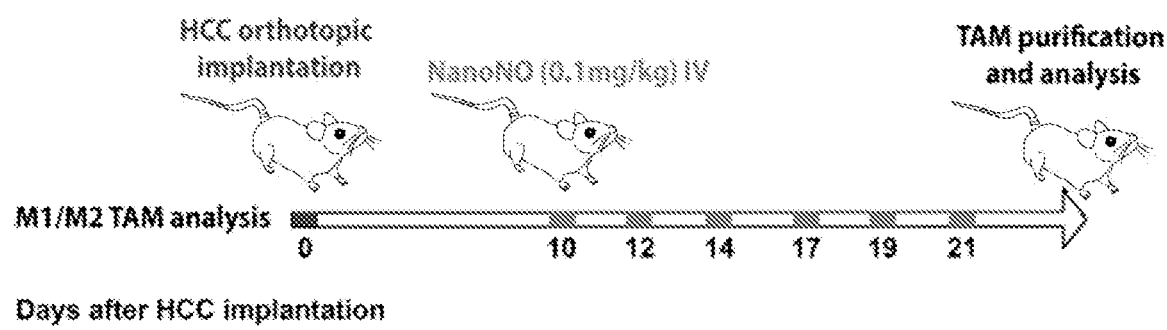
FIG. 6A shows treatment schedule for analysis of the TAM profile.

FIG. 6A shows treatment schedule for analysis of the TAM profile. C3H/HeNCrNarl male mice with orthotopic implants of HCA-1 cells were intravenously injected with NanoNO (0.1 mg/kg/dose, six doses, three doses per week). After treatment, TAMs were collected and enriched by CD11b-microbeads and separated by flow sorting. Gene transcription in different TAM populations was analyzed by quantitative real-time PCR.

Figure 6B:
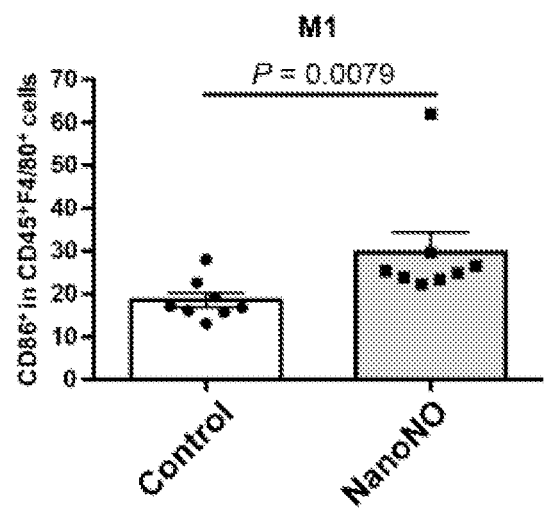
FIGS. 6Ba-6Bd show low-dose NanoNO reprograms immunosuppressive TAMs and increases tumor-infiltrating T cells in a $CCl_4$-induced HCC model.
Figure 6B:
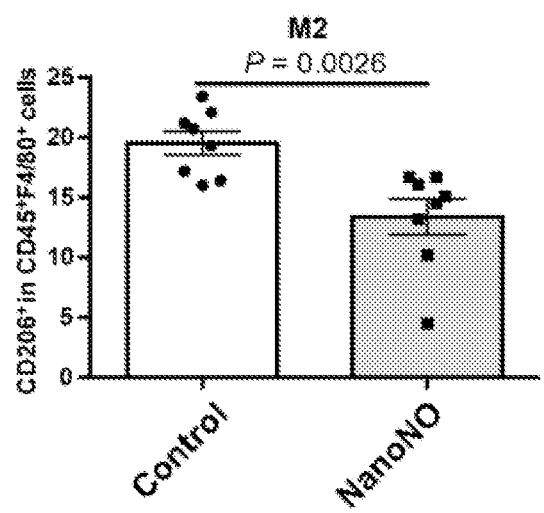
Figure 6B:
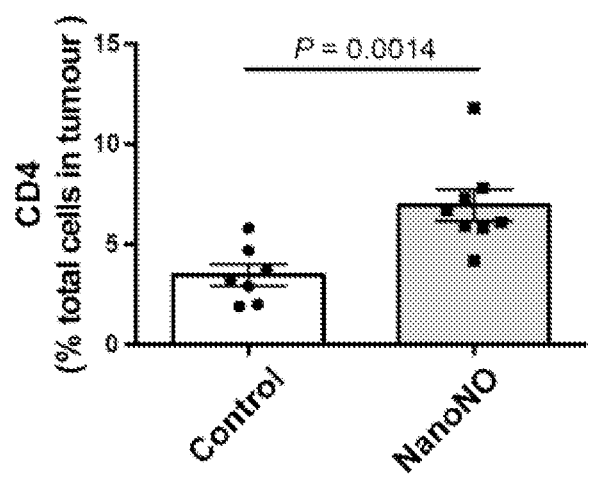
Figure 6B:
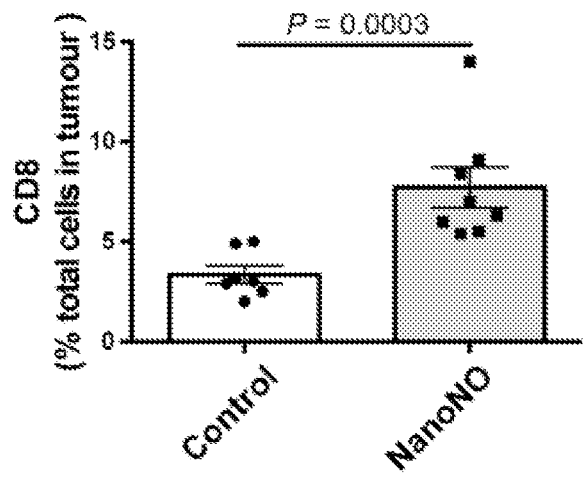

FIGS. 6Ba-6Bd show low-dose NanoNO reprograms immunosuppressive TAMs and increases tumor-infiltrating T cells in a CCl$_4$-induced HCC model. In FIGS. 6Ba-6Bb, low-dose NanoNO increased M1-like macrophages (F4/80$^+$ CD86$^+$) (FIG. 6Ba) and reduced M2-like macrophages (F4/80$^+$CD206$^+$) (FIG. 6Bb) in CCl$_4$-induced HCC, as measured by flow cytometry (n=8 mice). In FIGS. 6Bc-6Bd, low-dose NanoNO increased CD4 (FIG. 6Bc) and CD8 (FIG. 6Bd) T cells in CCl$_4$-induced HCC, as measured by flow cytometry (control, n=7 mice; NanoNO, n=8 mice). All data are shown as the mean value± the s.e.m. Analysis was performed using two-tailed Mann-Whitney U test.

Table 8 shows low-dose NanoNO reprograms immunosuppressive TAMs towards an immunostimulatory phenotype, increases tumor-infiltrating T cells and achieves synergistic anti-cancer effects when combined with a vaccine in orthotopic HCC models. In HCA-1 orthotopic tumors, low-dose NanoNO (0.1 mg/kg) increased the expression of M1-like genes and decreased the expression of M2-like genes in TAMs (n=6 mice). TAMs were enriched using CD11b-microbeads and separated by flow sorting. #P=0.0569, P=0.0082, *P=0.0479, P=0.0072, *P=0.0001 compared to control.

TABLE 8

TAM polarization by LD NanoNO

| Gene expression | | Control | NanoNO |
|---|---|---|---|
| M1 type | CXCL-11 | 1.35 ± 0.53 | 1.97 ± 0.41 |
| | NOS2 | 1.09 ± 0.21 | 2.52 ± 0.35## |
| | IL-1b | 1.25 ± 0.35 | 0.64 ± 0.28 |
| | TNF-α | 1.07 ± 0.16 | 1.49 ± 0.37 |
| | CXCL-9 | 1.55 ± 0.96 | 1.50 ± 0.64 |
| M2 type | CCL-22 | 1.03 ± 0.34 | 0.43 ± 0.15 |
| | CCL-17 | 0.99 ± 0.27 | 0.22 ± 0.11# |
| | IL-10 | 1.20 ± 0.26 | 0.11 ± 0.04** |
| | MRC1 | 1.04 ± 0.21 | 0.01 ± 0.00*** |
| | Arg-1 | 1.13 ± 0.24 | 0.62 ± 0.05* |

Figure 6C:
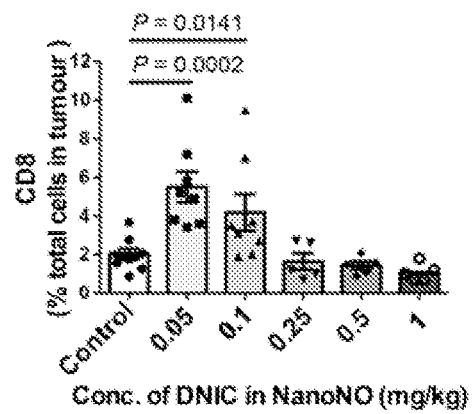
FIG. 6C shows low-dose NanoNO increased CD4 and CD8 T cells in tumors, as measured by flow cytometry.

FIG. 6C shows low-dose NanoNO increased the CD4 and CD8 T cells in tumors, as measured by flow cytometry (control, n=10 mice; 0.05 and 0.1 mg/kg NanoNO, n=8 mice; 0.25, 0.5 and 1 mg/kg NanoNO, n=5 mice).

Figure 6D:
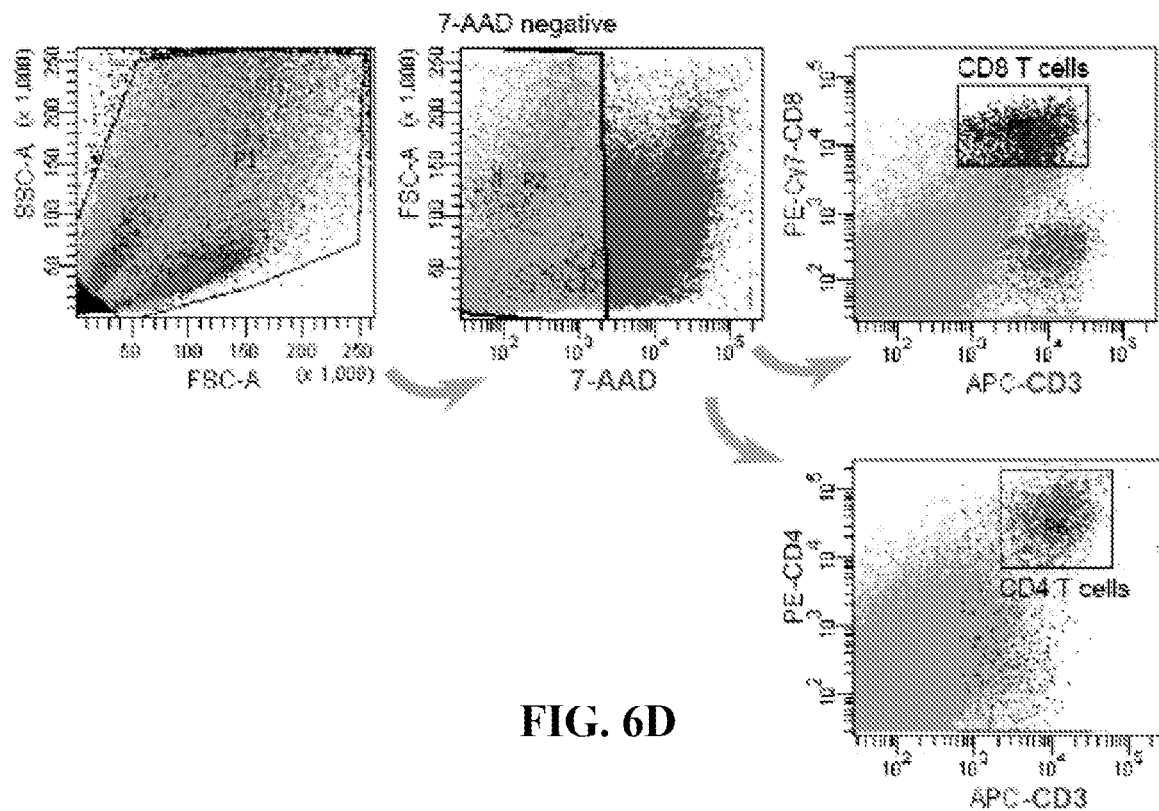
FIG. 6D shows gating strategy for flow cytometry to determine T cell subsets.

FIG. 6D shows gating strategy for flow cytometry to determine T cell subsets.

After treatment with low-dose NanoNO in the orthotopic HCA-1 HCC model, TAMs were enriched using CD11b-microbeads and separated by flow sorting (FIG. 6A). Although DNIC did not directly affect macrophage polarization in vitro (Table 9), low-dose NanoNO increased expression of the M1-type gene NOS2 and reduced expression of several M2-type genes (Ccl17, Il10, Mrc1, and Arg1) in TAMs in vivo. In CCl$_4$-induced HCC model, consistently, it increased M1-like macrophages (F4/80$^+$ CD86$^+$) and reduced M2-like macrophages (F4/80$^+$ CD206$^+$) in TME (FIGS. 6Ba-6Bd). The results suggest that low-dose NanoNO reprograms immunosuppressive TAMs towards an immunostimulatory phenotype through vessel normalization (FIGS. 6Ba-6Bd and Table 8). Moreover, treatment with NanoNO at low doses (DNIC: 0.05 and 0.1 mg/kg) significantly facilitated CD4$^+$ and CD8$^+$ T cell infiltration into HCC tumors in both orthotopic HCA-1 and CCl$_4$-induced HCC models compared with treatment with high doses of NanoNO or with the untreated group (FIGS. 6Ba-6Bd, 6C and 6D).

TABLE 9

Macrophage polarization after treartment of DNIC in vitro

| Gene expression | | Control | DNIC 0.5 μM | DNIC 1 μM |
|---|---|---|---|---|
| M1 type | CXCL-11 | 1.09 ± 0.22 | 2.02 ± 0.79* | 1.85 ± 0.72 |
| | iNOS | 1.15 ± 0.35 | 1.10 ± 0.35 | 0.93 ± 0.47 |
| | IL-1b | 1.00 ± 0.04 | 1.13 ± 0.07 | 1.21 ± 0.04 |
| | TNF-α | 1.00 ± 0.05 | 0.95 ± 0.08 | 0.94 ± 0.11 |
| | CXCL-9 | 1.02 ± 0.12 | 1.22 ± 0.17 | 1.22 ± 0.53 |
| | IL-6 | 1.04 ± 0.16 | 1.16 ± 0.03 | 1.27 ± 0.08 |
| M2 type | CCL-22 | 1.08 ± 0.26 | 0.96 ± 0.11 | 1.07 ± 0.22 |
| | CCL-17 | 1.01 ± 0.08 | 1.06 ± 0.13 | 1.19 ± 0.27 |
| | IL-10 | 1.03 ± 0.15 | 1,12 ± 0.16 | 1.22 ± 0.14 |
| | MRC1 | 1,00 ± 0.06 | 1.00 ± 0.17 | 1.19 ± 0.16 |
| | Arg-1 | 1.01 ± 0.07 | 1.08 ± 0.26 | 1.27 ± 0.28 |
| | PPARγ | 1.00 ± 0.03 | 0.92 ± 0.05 | 0.91 ± 0.13 |
| | TGF-β | 1.02 ± 0.11 | 1.11 ± 0.06 | 0.95 ± 0.03 |

The procedure of Western blot analysis was as follows. Cells or tissue were lysed in RIPA lysis buffer. Cell lysates were separated on a 10% acrylamide gel and transferred to a PVDF membrane. Membranes were blocked for 1 h in 5% skim milk and then incubated overnight with polyclonal antibodies against PD-L1 and R-actin (clone 122M4782, Cell Signaling, Danvers, Mass.).

The procedure of DNIC triggered activation of SP1 in HCA-1 HCC cells was as follows. HCA-1 cells expressing SP1 reporter (Qiagen, Germany) were established by transfection using Lipofectamine® 2000 (Thermo Fisher Scientific, USA). The cells were then treated with free-form DNIC. After 24 h incubated, the cells were lysed and luciferase signal was measured by microplate reader (Spark 10M, Tecan, Germany).

Figure 6E:
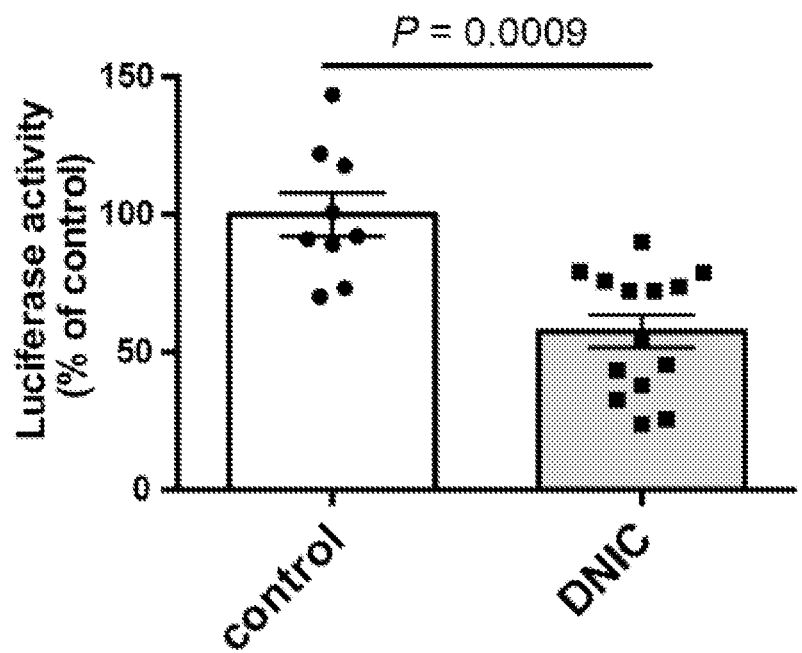
FIG. 6E shows DNIC triggered activation of SP1 in HCA-1 HCC cells.

FIG. 6E shows DNIC triggered activation of SP1 in HCA-1 HCC cells. SP-1 luciferase activity from HCA-1 cells transfected with an SP1 luciferase construct was significantly decreased after treatment with free-form DNIC (0.5 μM) (Control, n=9 biologically independent samples; DNIC, n=14 biologically independent samples). Data are pooled from two independent experiments. All data are shown as the mean value± the s.e.m. Analysis was performed using two-tailed Mann-Whitney U test.

Figure 6F:
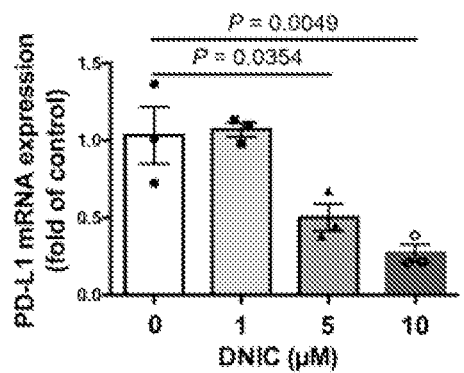
FIG. 6F is a data diagram showing reprogramming of tumor microenvironment by NanoNO.
Figure 6G:
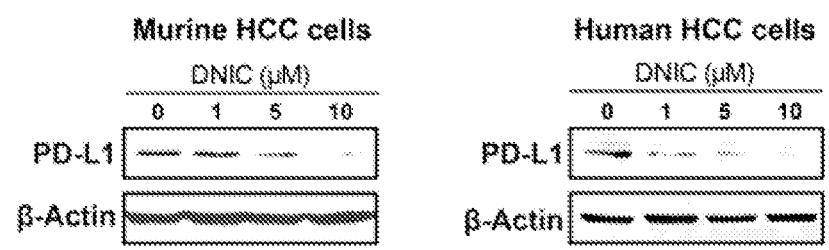
FIG. 6G is a Western blot staining diagram showing reprogramming of tumor microenvironment by NanoNO.

FIG. 6F is a data diagram showing reprogramming of tumor microenvironment by NanoNO. FIG. 6G is a Western blot staining diagram showing reprogramming of tumor microenvironment by NanoNO. PD-L1 mRNA and protein expression in HCA-1 cells was analysed by qRT-PCR (n=3 biologically independent samples) (FIG. 6F) and Western blot analysis (FIG. 6G) After treatment with free-form DNIC in vitro. The experiments were repeated twice independently.

Figure 6H:
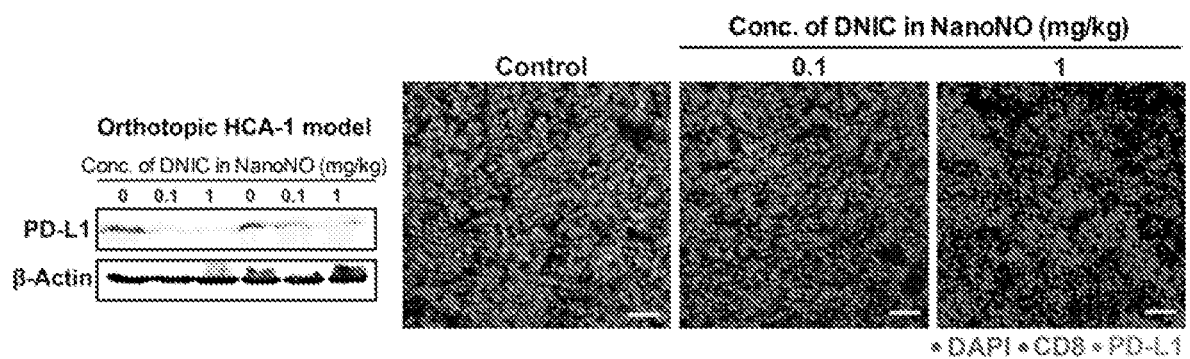
FIG. 6H is a Western blot staining diagram and immunofluorescence images showing reprogramming of tumor microenvironment by NanoNO.

FIG. 6H is a Western blot staining diagram and immunofluorescence images showing reprogramming of tumor microenvironment by NanoNO. Western blot analysis shows the reduced expression of PD-L1 in tumors after treatment with NanoNO. HCA-1 tumor-bearing mice were treated with NanoNO (0.1 or 1 mg/kg). Representative immunofluorescence images of HCA1 tumors 24 days postimplantation shown from two independent experiments. Scale bar, 50 μm. The experiments were repeated twice independently.

In addition to reduced T cell infiltration in tumors, the tumor-killing activity of the T cells is often impaired by immune checkpoint molecules. PD-L1, an immunosuppressive checkpoint ligand, is highly expressed in aggressive HCC and plays a crucial role in blocking the activation of cytotoxic $CD8^+$ T cells and suppressing T cell proliferation by interacting with its receptor PD-1 on T cells. The results indicated that DNIC decreased the activity of the Sp transcription factor that binds to the PD-L1 promoter and mediates PD-L1 expression (FIG. 6E). As expected, DNIC significantly reduced PD-L1 expression in both murine and human HCC cells in vitro in a dose-dependent manner (FIGS. 6F and 6G). Although both high- and low-dose NanoNO suppressed PD-L1 expression in HCC tumors in vivo, an increased number of tumor-infiltrating T cells was only observed following low-dose NanoNO-induced vessel normalization (FIG. 6H). Collectively, these data demonstrated that low-dose NanoNO can directly (e.g., by suppressing PD-L1 expression) and indirectly (e.g., by vessel normalization and TAM polarization) trigger a shift in immunosuppressive TME towards anti-cancer immunity.

Figure 6I:
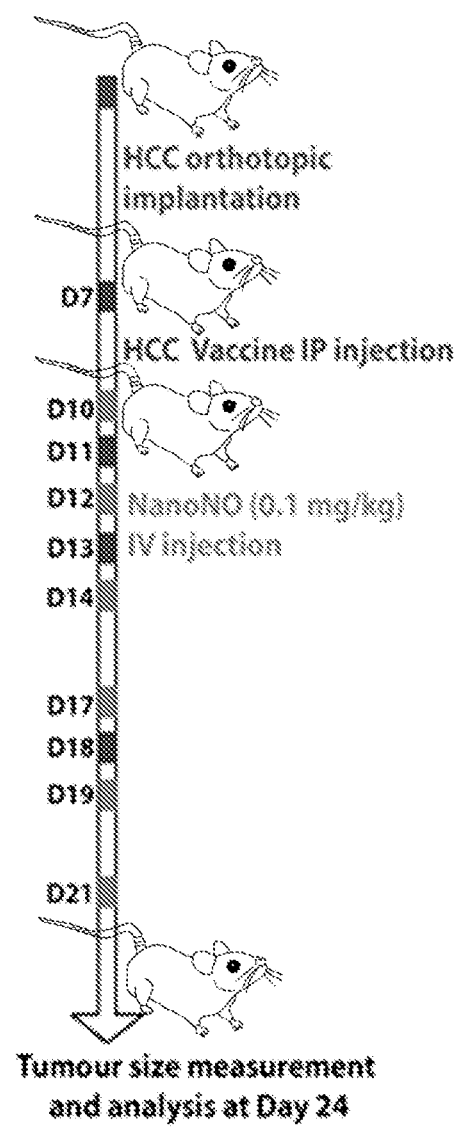
FIG. 6I is treatment protocol of reprogramming of tumor microenvironment by NanoNO.

FIG. 6I is treatment protocol of reprogramming of tumor microenvironment by NanoNO. Treatment protocol was as follows. Seven days after the implantation of HCA-1 cells, mice were injected intraperitoneally four times (at 2-to 3-day intervals) with $5 \times 10^6$ mitomycin C-treated cGM-CSF-overexpressing HCA-1 cells. For the combination groups, mice treated with cGM-CSF-secreting cancer cell vaccines, as above, received intravenous low-dose NanoNO on days 10, 12, 14, 17, 19 and 21.

Figure 6J:
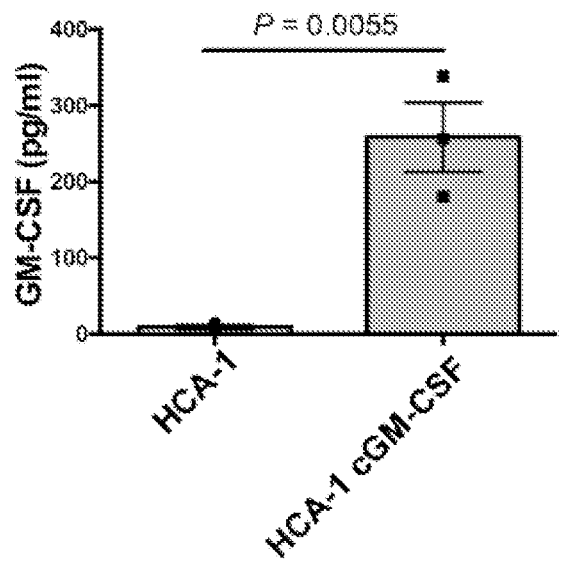
FIGS. 6Ja and 6Jb show generation and functional analysis of cGM-CSF modified whole-cell cancer vaccines.
Figure 6J:
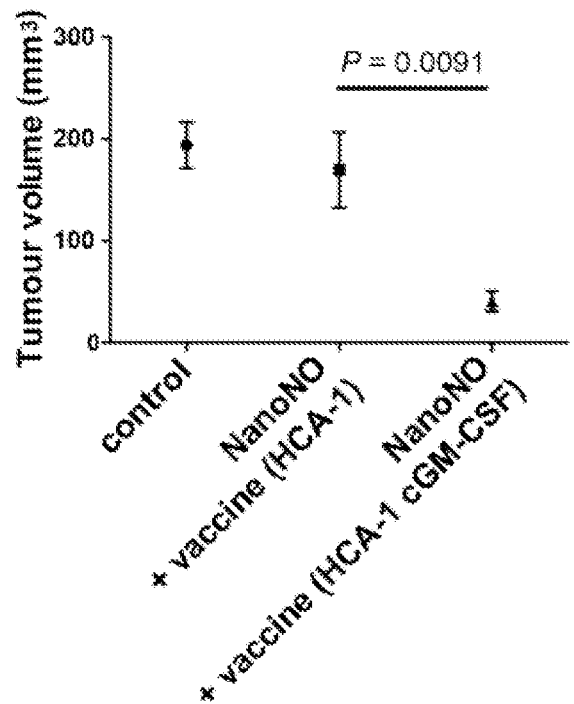

FIGS. 6Ja and 6Jb show generation and functional analysis of cGM-CSF modified whole-cell cancer vaccines. a, Enhanced production of GM-CSF by HCA-1 cells transfected with Lipofectamine 2000. The stable HCA-1 cGM-CSF clones with the highest GM-CSF expression were selected and cultured in 6-cm dishes at a concentration of $2.5 \times 10^5$ cells per well for 24 hours. GM-CSF production was then determined with an ELISA (n=3 biologically independent samples). b, The combination of low-dose NanoNO and vaccine treatment reduced tumor sizes. Seven days after implantation of HCA-1 cells, mice were injected intraperitoneally four times (at 2- to 3-day intervals) with $5 \times 10^6$ mitomycin C-treated HCA-1 cells with or without overexpression of cGM-CSF. For the combination treatment, mice treated with cancer cell vaccines as above received intravenous low-dose NanoNO on days 10, 12, 14, 17, 19 and 21 (control, n=15 mice; combination of HCA-1 vaccine and NanoNO, n=6 mice; combination of cGM-CSF HCA-1 vaccine and NanoNO, n=9 mice). All data are shown as the mean value± the s.e.m.

Figure 6K:
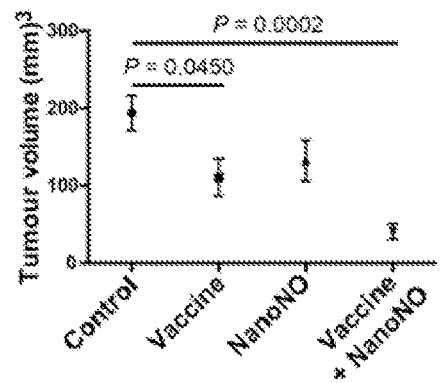
FIG. 6K shows the combination of low-dose NanoNO and vaccine treatment significantly reduced tumor sizes.
Figure 6L:
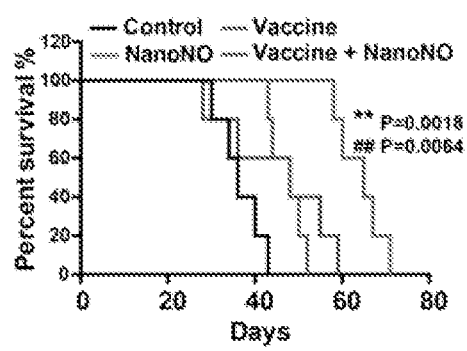
FIG. 6L shows the combination of low-dose NanoNO and vaccine treatment increased the overall survival in an orthotopic HCC model.

FIGS. 6K and 6L show the combination of low-dose NanoNO and vaccine treatment significantly reduced tumor sizes (control, n=15 mice; NanoNO alone, n=10 mice; vaccine alone, n=11 mice; combination group, n=9 mice) (FIG. 6K) and increased the overall survival (n=5 mice) (FIG. 6L) in an orthotopic HCC model. **P=0.0018 compared to NanoNO alone and ##P=0.0064 compared to the vaccine alone.

Figure 6M:
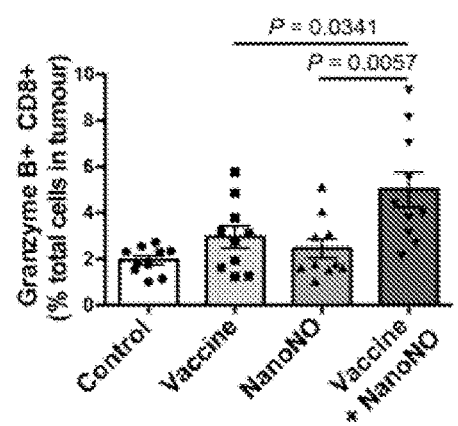
FIG. 6M shows the percentage of granzyme B-positive CD8 T cells in HCA-1 tumors was detected 24 days post-implantation in the presence or absence of treatment with NanoNO and/or the HCC vaccine by flow cytometry (n=10 mice).
Figure 6N:
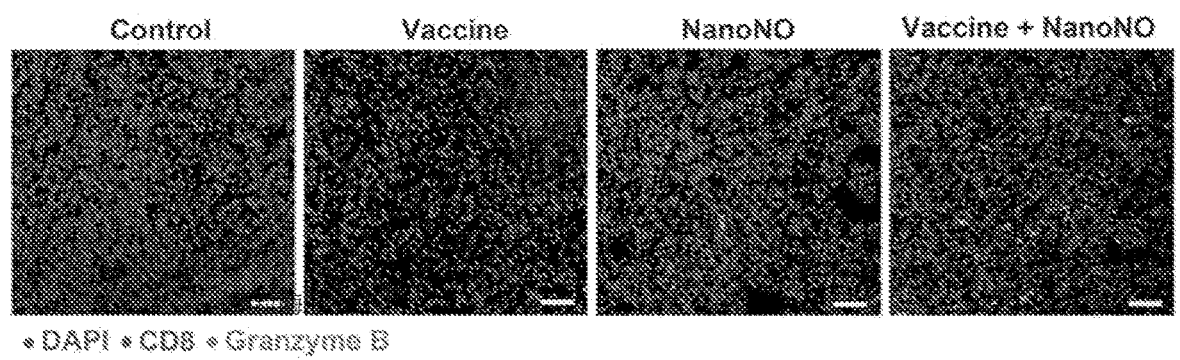
FIG. 6N shows the percentage of granzyme B-positive CD8 T cells in HCA-1 tumors was detected 24 days post-implantation in the presence or absence of treatment with NanoNO and/or the HCC vaccine by immunofluorescence staining.

FIGS. 6M and 6N show the percentage of granzyme B-positive CD8 T cells in HCA-1 tumors was detected 24 days postimplantation in the presence or absence of treatment with NanoNO and/or the HCC vaccine by flow cytometry (n=10 mice) (FIG. 6M) and by immunofluorescence staining (FIG. 6N). Representative immunofluorescence images of HCA-1 tumors are shown from two independent experiments (DAPI, blue; granzyme B, green; $CD8^+$ T cells, red). All data are shown as the mean value± the s.e.m.

The procedure of whole-dell vaccine therapy was as follows. Stable HCA-1 cells expressing encoding codon-optimized GM-CSF (cGM-CSF) were established by transfection using Lipofectamine® 2000 (Thermo Fisher Scientific, USA) and G418 (300 μg/mL) selection. Cells were detached by EDTA, resuspended in PBS ($10^7$ cells/mL) and incubated with mitomycin C (50 μg/mL) for 1 h at 37° C. In the HCC tumor model, 7 days after tumor implantation, mice were injected intraperitoneally four times (at 2- to 3-day intervals) with $5 \times 10^6$ mitomycin C-treated cells. On the $10^{th}$ day after implantation, tumor-bearing C3H/HeNCr-Narl male mice were injected intravenously six times (three times per week) with NanoNO (DNIC: 0.1 mg/kg). Two weeks after the first NanoNO treatment, mice were sacrificed for analysis.

Finally, the inventors examined whether treatment with low-dose NanoNO could enhance the anti-cancer efficacy of an HCC vaccine therapy (FIG. 6I). In particular, the inventors used an immunostimulating whole-cell HCC vaccine consisting of modified HCA-1 cells transfected with codon-optimized GM-CSF (cGM-CSF), which significantly increased GM-CSF expression levels (FIGS. 6Ja and 6Jb). GM-CSF is widely used as an adjuvant to increase the immune response in immunotherapy protocols by promoting dendritic cell recruitment and maturation. GM-CSF-secreting tumor vaccines were reported to stimulate potent, specific, and long-lasting antitumor effects. The combination of low-dose NanoNO and HCC vaccine treatment (mitomycin-C treated cGM-CSF-transduced HCA-1 cells) significantly reduced tumor progression and increased the overall survival in the orthotopic HCC model compared with low-dose NanoNO mono-therapy or vaccination alone (FIGS. 6K and 6L). Moreover, the combined treatment significantly increased cytotoxic T cell activation in HCC, as measured by the granzyme B expression in the CD8+ T cells (FIGS. 6M and 6N). These data indicate that low-dose NanoNO treatment augments the anti-tumor effect of an HCC vaccine therapy.

Example 7

Evaluation of Effect on Suppression of Distant Metastasis by NanoNO

Normalizing tumor vessels in primary tumors is known to impair distal metastasis; however, the effect of vessel normalization in metastatic lesions remains largely unexplored. In addition, the role of NO in metastasis development is not clear. Therefore, the inventors first assessed the direct impact of DNIC on the metastatic potential of HCC cells in vitro.

The procedure of construction of pLenti DEST CMV Puro (w118-1)-GpNLuc Plasmid was as follows. GpNLuc was PCR amplified by Q5® High-Fidelity DNA polymerase (New England Biolabs) from pRetroX-Tight-MCS_PGK-GpNLuc (a gift from Antonio Amelio; Addgene plasmid #70185) with a forward primer (5'-AAAAAAGCAGG-CTCGAGCCACCATGGTGAGCAAGGGC-3')(SEQ ID NO: 87) and a reverse primer (5'-AGAAAGCTGGGT-CTAGAATTACGCCAGAATGCGT-3')(SEQ ID NO: 88). Gel purified GpNLuc insert and pENTR-Luc (w158-1) (a gift from Eric Campeau & Paul Kaufman; Addgene plasmid #17473) were digested by NcoI and XbaI, and ligated with Quick Ligation™ kit (New England Biolabs) to generate pENTR-GpNLuc. pLenti DEST CMV Puro (w118-1)-GpNLuc was created by Gateway® LR cloning (ThermoFisher Scientific) with pLenti DEST CMV Puro (w118-1) (a gift from Eric Campeau & Paul Kaufman; Addgene plasmid #17452) and pENTR-GpNLuc plasmids.

The procedure of Lentivirus production of GpNluc was as follows. HEK293T cells were co-transfected with psPAX2 (a gift from Didier Trono; Addgene plasmid #12260), pMD2.G (a gift from Didier Trono; Addgene plasmid #12259), and pLenti DEST CMV Puro (w118-1)-GpNLuc by PEI (Alfa Aesar; 1 mg/mL polyethylenimine, linear, MW 25,000) transfection. The medium was replaced with DMEM+GlutaMAX supplemented with 10% FBS at 18 h post-transfection followed by viral medium harvest and medium replacement at 48 and 72 h post-transfection. Pooled viral media was centrifuged at 500×g for 10 min at 4° C. to collect viral supernatant.

The procedure of generation of stable HCA-1-GpNLuc cells was as follows. $5 \times 10^4$ HCA-1 cells were resuspended in 1 mL DMEM+GlutaMAX™ supplemented with 10% FBS and 10 μg/mL polybrene (Merck), added to a 6-well plate containing 500 μL of GpNLuc lentivirus, and cultured at 37° C. with 5% $CO_2$ in a humidified incubator. At 72 h post-transduction, the transduced HCA-1 cells were sequentially expanded in a 6-, 10- and 15-cm dish for subsequent fluorescence activated cell sorting (FACS) to isolate GFP-positive HCA1-A cells stably expressing the GpNLuc imaging reporter.

The procedure of experimental metastasis assay was as follows. HCA-1-GPNLuc cells were ($2.5 \times 10^6$ cells/mL) injected into the lateral tail vein. NanoNO (DNIC: 0.1 mg/kg, three doses per week), TRAIL (5 mg/kg, five doses per week) or Dox (4 mg/kg, three dose per week) was intravenously administered to mice beginning 7 days after the injection of HCA-1-GPNLuc cells. The metastatic burdens were quantified by measuring the luciferase activity 19 days after the injection of HCA-1-GPNLuc cells. Lung tissues were collected and homogenized in lysis buffer (10 mM Tris-HCl, 1% Triton X-100, 0.1% SDS, 0.1% SDC and 140 mM NaCl). Luciferase substrate was added to tissue lysates and measured by a microplate reader (Spark 10M, Tecan, Germany).

The procedure of transwell invasion assay was as follows. Cell invasion was examined using a QCM ECMatrix 24-well Cell Invasion Assay (EMD Millipore, USA). HCA-1 cells were seeded in the top chamber without serum. DMEM-H containing 10% FBS was added to the lower chamber. Following incubation for 72 h, the cells on the lower surface were fixed with 4% paraformaldehyde (PFA, in PBS). The chambers were rinsed in PBS and stained with 1% crystal violet (in 90% ethanol) for 30 min. For each experimental condition, 10 image fields were photographed by microscopy (IX83, Olympus, Japan) and quantified.

Figure 7A:
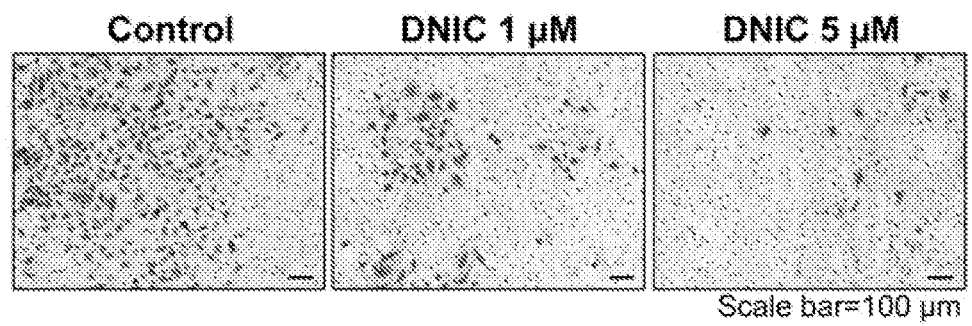
FIG. 7A shows free-form DNIC modulates the TME in metastatic lesions and suppresses metastatic progression of HCC.
Figure 7B:
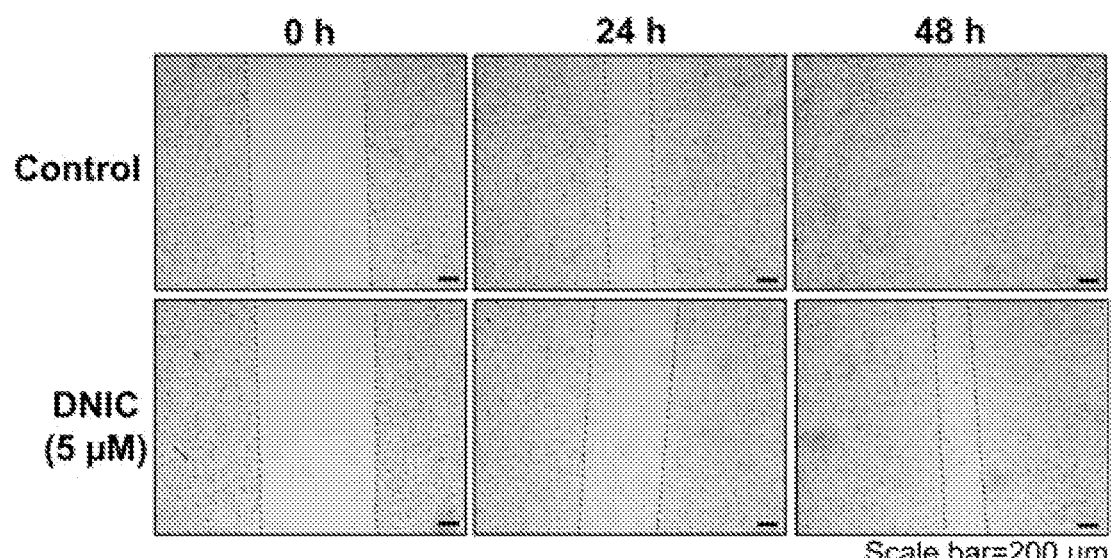
FIG. 7B shows free-form DNIC modulates the TME in metastatic lesions and suppresses metastatic progression of HCC.

FIGS. 7A and 7B show free-form DNIC modulates the TME in metastatic lesions and suppresses metastatic progression of HCC. 7A-7B, Invasion (7A) and wound healing assays (7B) of HCA-1 cells were performed 72 h after treatment with free DNIC at different doses. The experiments were repeated twice independently.

Figure 7C:
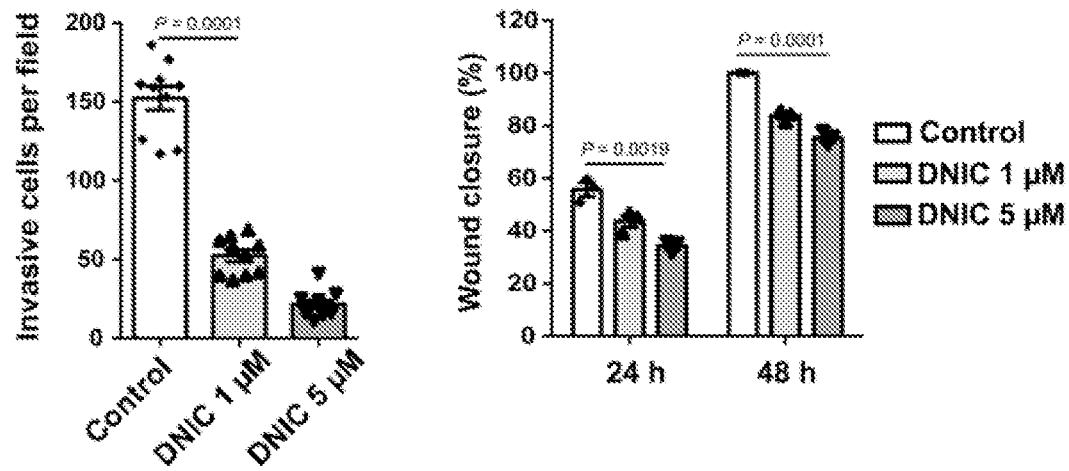
FIG. 7C shows images from invasion (n=10 biologically independent samples) and wound healing assays (n=3 biologically independent samples) were quantified with ImageJ.

FIG. 7C shows images from invasion (n=10 biologically independent samples) and wound healing assays (n=3 biologically independent samples) were quantified with ImageJ.

Figure 7D:
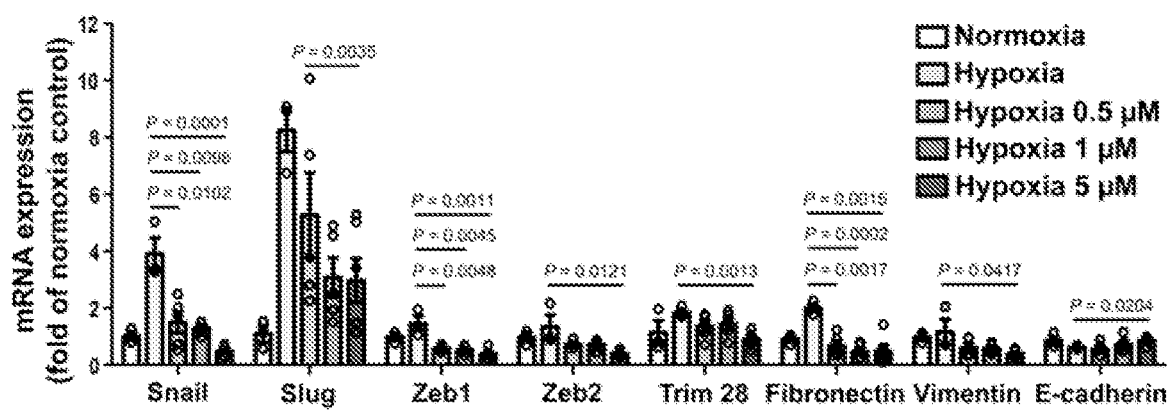
FIG. 7D shows DNIC reverses the EMT phenotype of HCA-1 cells under hypoxic conditions (1% oxygen).

FIG. 7D shows DNIC reverses the EMT phenotype of HCA-1 cells under hypoxic conditions (1% oxygen). The mRNA level was determined by qRT-PCR 24 h after treatment with free DNIC at different doses (control and hypoxia, n=3; 0.5 and 1 μM DNIC, n=5; 5 μM DNIC, n=6 biologically independent samples).

Figure 7E:
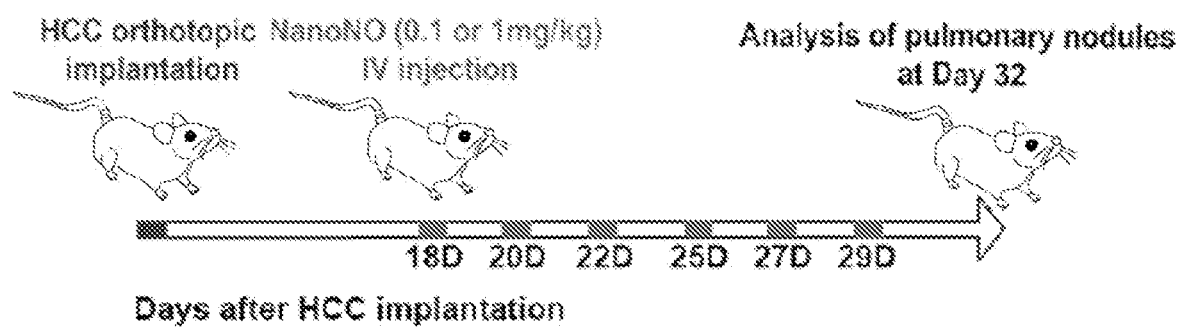
FIG. 7E shows treatment schedule for spontaneously occurring lung metastasis models.

FIG. 7E shows treatment schedule for spontaneously occurring lung metastasis models. C3H/HeNCrNarl male mice with orthotopic implants of HCA-1 cells were intravenously injected with NanoNO (0.1 or 1 mg/kg/dose, six doses, three doses per week). The lung nodules were collected for further analysis after 2 weeks of treatment.

Figure 7F:
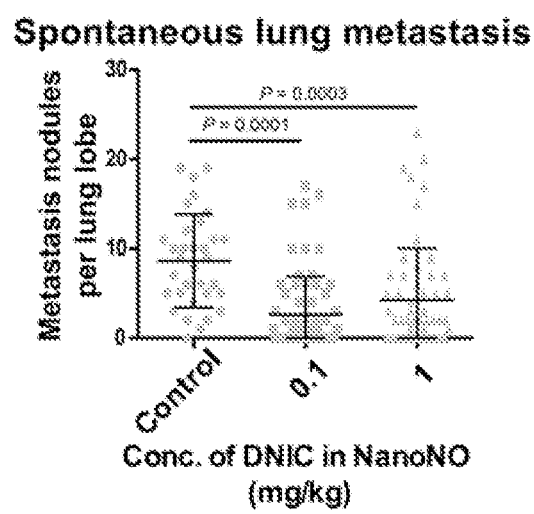
FIGS. 7Fa-7Fb show the number of spontaneously occurring lung metastatic nodules in orthotopic HCA-1 HCC models was reduced in mice treated with NanoNO.
Figure 7F:
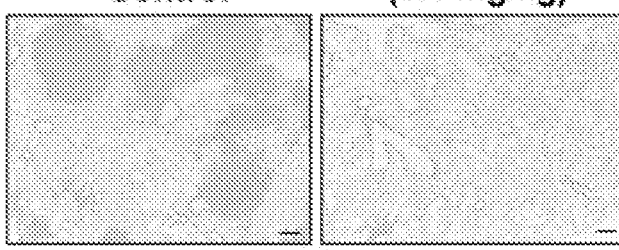

FIGS. 7Fa and 7Fb show the number of spontaneously occurring lung metastatic nodules in orthotopic HCA-1 HCC models was reduced in mice treated with NanoNO (control, n=33 lung lobes from 11 mice; low dose NanoNO, n=69 lung lobes from 23 mice; high dose NanoNO, n=57 lung lobes from 19 mice). H&E staining images showing metastatic tumor nodules in the lung. Scale bar, 200 μm. Data are the mean values± the s.e.m.

Figure 7G:
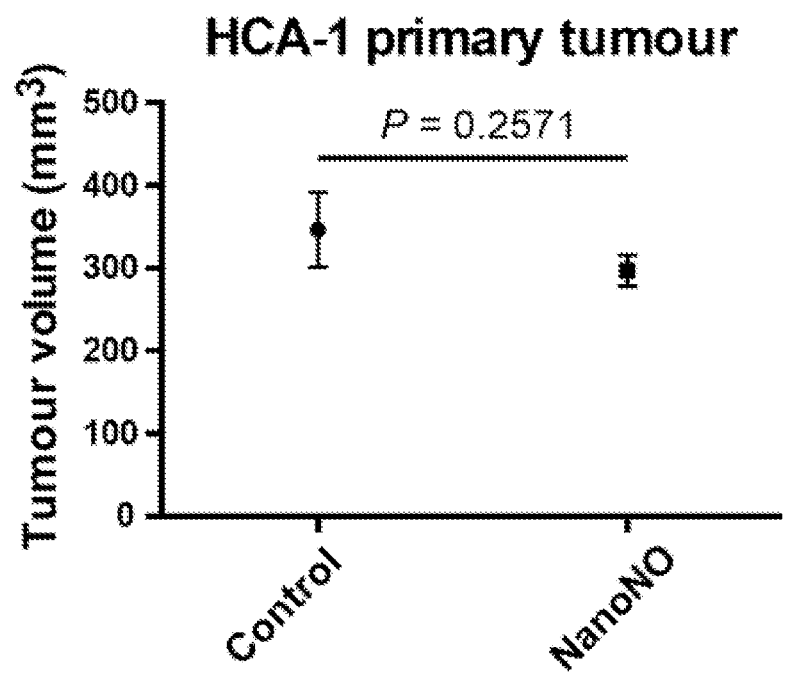
FIG. 7G shows treatment with a low dose of NanoNO did not affect primary tumor sizes compared with that of the untreated control in the orthotopic HCA-1 HCC model.

FIG. 7G shows treatment with a low dose of NanoNO did not affect primary tumor sizes compared with that of the untreated control in the orthotopic HCA-1 HCC model.

Figure 7H:
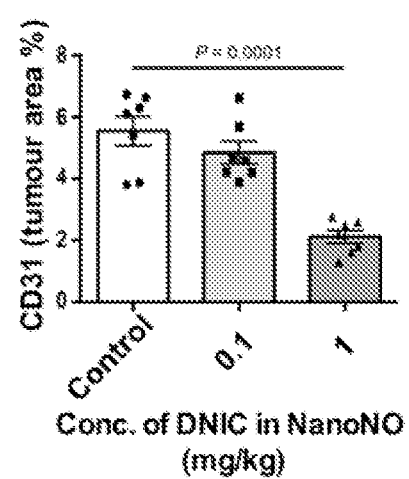
FIGS. 7Ha-7Hc show quantification of changes in the TME in spontaneously occurring metastatic lung nodules after treatment with NanoNO.
Figure 7H:
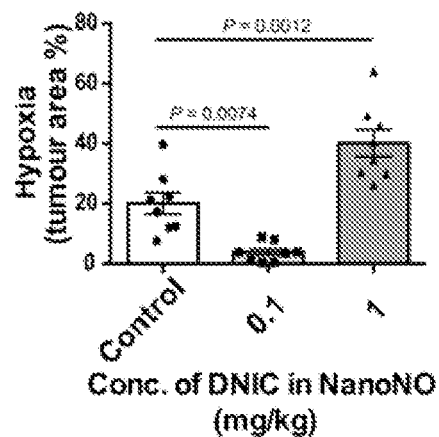
Figure 7H:
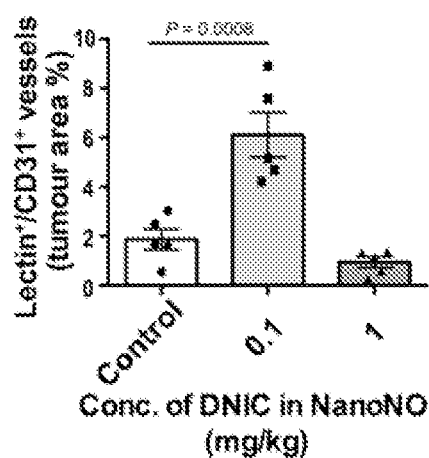

FIGS. 7Ha-7Hc show quantification of changes in the TME, including mean vessel density (CD31+/DAPI, n=7 section images from three mice), tumor hypoxia (pimonidazole+/DAPI, n=8 section images from four mice) and perfused functional vessels (CD31+lectin+/DAPI, n=5 section images from three mice), in spontaneously occurring metastatic lung nodules after treatment with NanoNO.

Figure 7I:
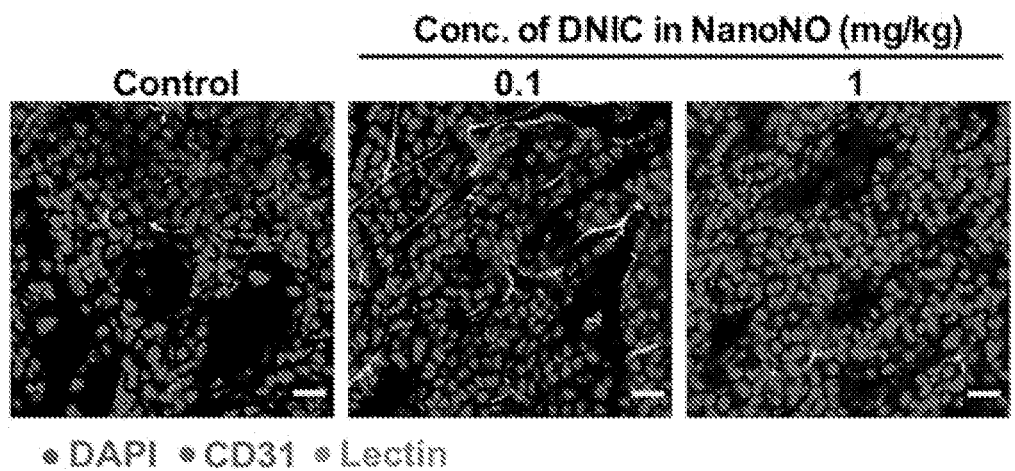
FIG. 7I shows representative immunofluorescence images of functional vessels indicated by $CD31^+lectin^+$ staining in lung metastatic nodules.

FIG. 7I shows representative immunofluorescence images of functional vessels indicated by CD31+lectin+ staining in lung metastatic nodules are shown. Scale bar, 50 μm. The experiments were repeated twice independently.

Figure 7J:
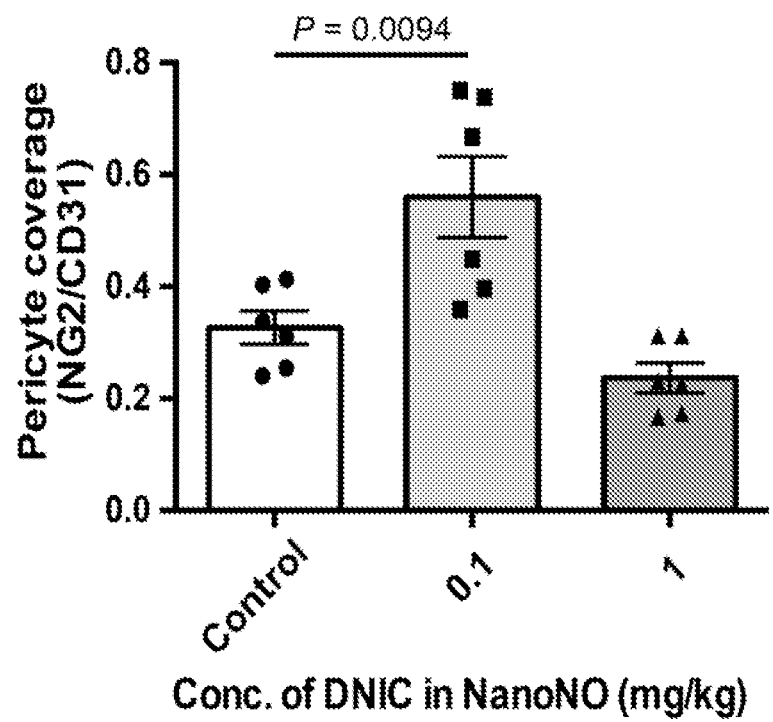
FIG. 7J shows quantification of changes in functional vessels with pericyte coverage (NG2/CD31) in spontaneously occurring metastatic lung nodules after treatment with high-dose (1 mg/kg) or low-dose (0.1 mg/kg) NanoNO.

FIG. 7J shows quantification of changes in functional vessels with pericyte coverage (NG2/CD31) in spontaneously occurring metastatic lung nodules after treatment with high-dose (1 mg/kg) or low-dose (0.1 mg/kg) NanoNO.

Figure 7K:
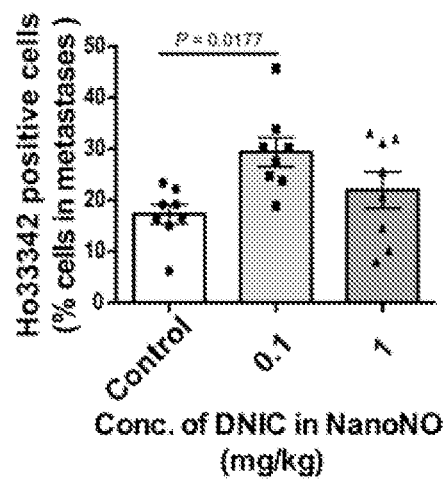
FIG. 7K shows the percentage of Hoechst 33342-positive cells (n=8 mice) in spontaneously occurring metastatic lung nodules after treatment with NanoNO.
Figure 7L:
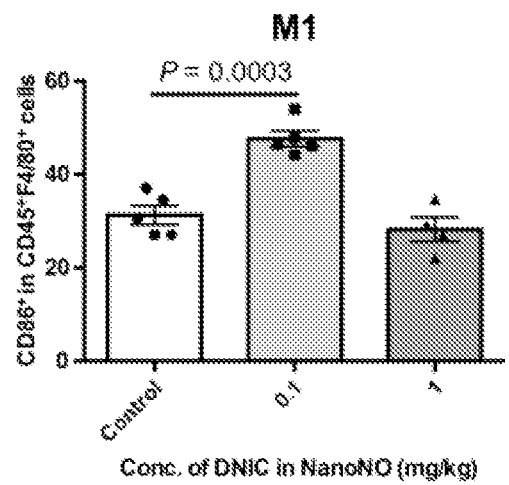
FIGS. 7La and 7Lb show low-dose NanoNO reprograms immunosuppressive TAMs in spontaneously occurring metastatic lung nodules.
Figure 7L:
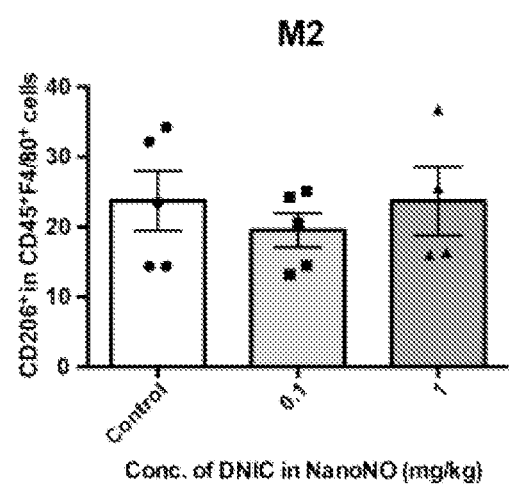
Figure 7M:
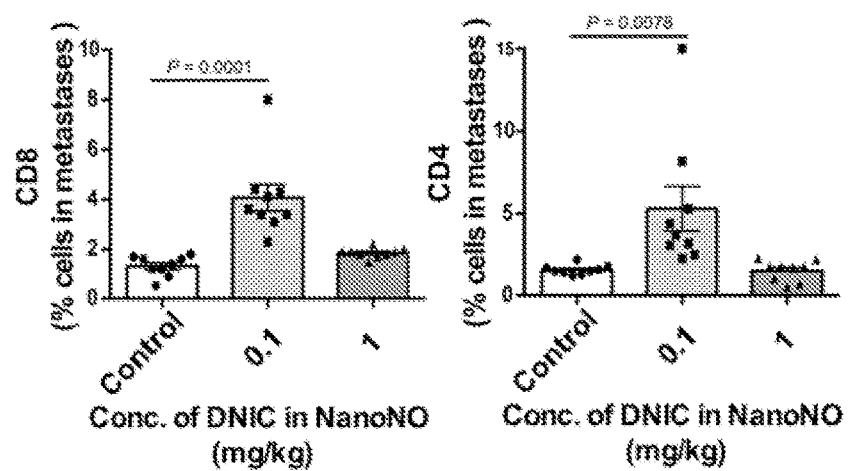
FIG. 7M shows infiltration of the CD4 and CD8 T cells in spontaneously occurring metastatic lung nodules after treatment with NanoNO.

FIGS. 7K and 7M show the percentage of Hoechst 33342-positive cells (n=8 mice) (FIG. 7K) and infiltration of the CD4 and CD8 T cells (n=9 mice) (FIG. 7M) in spontaneously occurring metastatic lung nodules after treatment with NanoNO, as measured by flow cytometry.

FIGS. 7La and 7Lb show low-dose NanoNO reprograms immunosuppressive TAMs in spontaneously occurring metastatic lung nodules. 7La-7Lb, Low-dose NanoNO increased M1-like macrophages (F4/80$^+$CD86$^+$) (FIG. 7La) and reduced M2-like macrophages (F4/80$^+$CD206$^+$) (FIG. 7Lb) in spontaneously occurring metastatic lung nodules of mice bearing orthotopic HCA-1 tumors, as measured by flow cytometry (control and 0.1 mg/kg NanoNO, n=5 mice; 1 mg/kg NanoNO, n=4 mice).

Treatment with DNIC significantly inhibited the migration and invasion of HCA-1 cells (FIGS. 7A-7C). Moreover, DNIC prevented the increase in epithelial-mesenchymal transition (EMT) markers and the reduction of E-cadherin expression in a dose-dependent manner in HCA-1 cells cultured in hypoxic conditions (FIG. 7D). The inventors further examined the effect of DNIC delivered by NanoNO on the progression of lung metastasis in mice bearing orthotopic HCA-1 tumors. The treatment began on day 18 after tumor inoculation to mimic the treatment procedure for advanced-stage HCC (FIG. 7E). NanoNO at a low dose (0.1 mg/kg) significantly suppressed the development of lung metastasis (FIGS. 7Fa and 7Fb) without affecting the primary HCC tumor burden (FIG. 7G). NanoNO mediates metastasis suppression possibly through inhibiting EMT in HCC cells and reprogramming the prometastatic TME.

Consistent with the antiangiogenic effect of NanoNO on primary HCC, a decrease in tumor MVD and an increase in tumor hypoxia were observed following high doses of NanoNO (1 mg/kg) in lung metastases (FIGS. 7Ha-7Hc). In contrast, treatment with low-dose NanoNO normalized tumor vessels, as indicated by the increased functional vessels (Lectin$^+$ CD31$^+$ and NG2$^+$ CD31$^+$ vessels) (FIGS. 7Ha-7Hc, 7I and 7J) and tumor perfusion (Hoechst 33342$^+$ area) (FIG. 7K), and reprogrammed the tumor immune microenvironment by polarizing TAMs towards an immune stimulatory phenotype (FIGS. 7La and 7Lb) and increasing T cell infiltration in lung metastases (FIG. 7M).

Figure 7N:
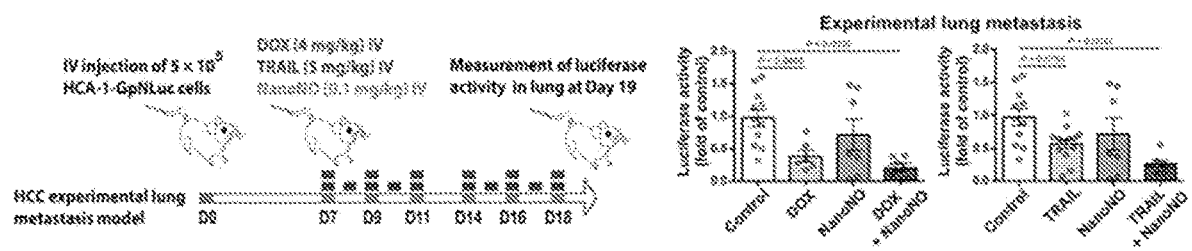
FIG. 7N shows treatment protocol and treatment effect of the experimental lung metastasis model.

FIG. 7N shows treatment protocol and treatment effect of the experimental lung metastasis model. Seven days after the IV injection of HCA-1-GpNLuc cells (5.0×10$^5$ cells in 200 μL PBS), mice were treated with doxorubicin (DOX) (4 mg/kg, IV) six times (at 2- to 3-day intervals) or recombinant tumor necrosis factor-related apoptosis-inducing ligand (TRAIL, 5 mg/kg, IV) ten times (at 1- to 2-d intervals). For the combination groups, mice received low-dose NanoNO (0.1 mg/kg, IV) on days 7, 9, 11, 14, 16 and 18. The experimental pulmonary metastatic burdens were analysed and quantified by measuring the luciferase activity of HCA-1-GpNLuc cells on day 19 (control, n=11 mice; TRAIL, n=13 mice; DOX, n=6 mice; NanoNO and combination group, n=7 mice). All data are shown as the mean value± the s.e.m.

Finally, the inventors examined whether normalizing the TME in metastatic HCC with low-dose NanoNO exhibited synergistic effects on suppression of metastasis growth when combined with chemotherapeutic (DOX) and macromolecular TRAIL therapies in an experimental lung metastasis model that was used to assess the direct effect of therapeutic agents on metastasis growth (FIG. 7N). The HCA-1-GpNLuc HCC experimental lung metastasis model was established by intravenous injection of 5×10$^5$ HCA-1-GpNLuc cells, and the treatment began on day 7 after tumor cell injection. Low-dose NanoNO in combination with DOX or TRAIL therapy synergistically suppressed metastasis growth in the experimental lung metastasis model (FIG. 7N).

In summary, the nanoparticles of the present invention (i.e., NanoNO) have the effect on good biocompatibility and stability, no damage to normal tissues, treating cancer (e.g., hepatocellular carcinoma, HCC), enhancing effect of the liver cancer drug, enhancing effect of the liver cancer vaccine, and alleviation of tumor hypoxia. In addition, the nanoparticle of the present invention (i.e., NanoNO) greatly improves the rapid half-life of a nitric oxide donor in organisms, and can continuously release nitric oxide for a long time. The nanoparticle of the present invention (i.e., NanoNO) can be used as anti-cancer therapeutic agents, and is useful for suppressing tumors. The outstanding effects make it an adjuvant for cancer, improve the tumor microenvironment, and can greatly increase the efficacy of chemotherapy, immunotherapy and large molecular protein therapy. The nanoparticle of the present invention (i.e., NanoNO) can also be loaded with different chemotherapeutics at the same time for common delivery.

Although the present invention has been described with reference to the preferred embodiments, it will be apparent to those skilled in the art that a variety of modifications and changes in form and detail may be made without departing from the scope of the present invention defined by the appended claims.

What is claimed is:

1. A nanoparticle, comprising:
   a core comprising at least one nitric oxide donor, and the core is encapsulated in a polymer and a lipid through an oil-in-water single emulsion to form the nanoparticle;
   wherein the at least one nitric oxide donor is a dinitrosyl iron complex (DNIC);
   wherein the polymer is poly D,L-lactide-co-glycolic acid (PLGA);
   wherein the lipid is 1,2-distearoyl-sn-glycero-3-phosphoethanolamine-N-[methoxy(polyethylene glycol)-2000] (DSPE-PEG2000);
   wherein the nanoparticle has an effective amount ranging from 0.5-1 mg/kg;
   wherein the nanoparticle has a polydispersity index (PDI) ranging from 0.116-0.176
   wherein the nanoparticle has a zeta potential ranging from −20 to −26 mV; and
   wherein the nanoparticle has an encapsulation efficiency ranging from 75-85%.

2. The nanoparticle according to claim 1 has a particle diameter ranging from 107 nm to 131 nm.

3. A method for preparing a nanoparticle of claim 1, comprising the steps of:
   (a) dissolving a core, a polymer and a lipid in an organic phase;
   (b) adding the organic phase to deionized water and performing ultrasonication, and then obtaining an emulsion through an oil-in-water single emulsion; and
   (c) subjecting the emulsion to a centrifugation and collecting a precipitate, followed by suspending the precipitate in a buffer to obtain the nanoparticle;
   wherein the core comprises at least one nitric oxide donor, and the core is encapsulated in the polymer and the lipid through the oil-in-water single emulsion.

4. The method according to claim 3, wherein the nanoparticle has a particle diameter ranging from 107 nm to 131 nm.

5. The method according to claim 3, wherein the at least one nitric oxide donor is a dinitrosyl iron complex (DNIC).

6. The method according to claim 3, wherein the polymer is poly D,L-lactide-co-glycolic acid (PLGA).

7. The method according to claim 3, wherein the stabilizer is 1,2-distearoyl-sn-glycero-3-phosphoethanolamine-N-[methoxy(polyethylene glycol)-2000] (DSPE-PEG2000).

8. A method for treating cancer, comprising:
   administering to a subject in need thereof a pharmaceutical composition comprising an effective amount of the nanoparticle according to claim 1; wherein the effective amount of the nanoparticle ranges from 0.5-1 mg/kg.

9. The method according to claim 8, wherein the cancer is a hepatocellular carcinoma (HCC).

10. The method according to claim 8, wherein the nanoparticle continuously releases nitric oxide.

11. A method for enhancing effect of a liver cancer drug, comprising administering to a subject in need thereof an agonist comprising an effective amount of the nanoparticle according to claim 1.

12. The method according to claim 11, wherein the liver cancer drug is doxorubicin or a tumor necrosis factor-related apoptosis-inducing ligand (TRAIL).

13. A method for ameliorating tumor hypoxia, comprising administering to a subject in need thereof a pharmaceutical composition comprising an effective amount of the nanoparticle according to claim 1.

14. A method for enhancing effect of a liver cancer vaccine, comprising administering to a subject in need thereof an agonist comprising an effective amount of the nanoparticle according to claim 1.

* * * * *